United States Patent [19]
White et al.

[11] Patent Number: 5,858,701
[45] Date of Patent: Jan. 12, 1999

[54] DNA ENCODING AN INSULIN RECEPTOR SUBSTRATE

[75] Inventors: Morris F. White, West Roxbury; Xiao Jian Sun, Boston, both of Mass.; Jacalyn H. Pierce, Potomac, Md.

[73] Assignee: Joslin Diabetes Center, Inc., Boston, Mass.

[21] Appl. No.: 317,310

[22] Filed: Oct. 3, 1994

[51] Int. Cl.⁶ .......................... C12N 15/12; C12N 15/63; C12N 15/85
[52] U.S. Cl. ............... 435/69.1; 435/325; 435/252.3; 435/320.1; 536/23.5
[58] Field of Search ................ 435/69.1, 252.3, 435/320.1, 325; 536/23.1, 23.5; 935/23, 19, 70

[56] References Cited

U.S. PATENT DOCUMENTS 5,260,200  11/1993  Kahn et al. .......................... 435/68.1

OTHER PUBLICATIONS

Rudinger, In "Peptide Hormones" (Jun. 1976) ed. J.A. Parsons, University Park Press, Baltimore, pp. 1–7.
Keegan, A.D. et al, (1994) "An IL–4 Receptor Region Containing an Insulin Receptor Motif is Important for IL–4–mediated IRS–1 Phosphorylation and Cell Growth", *Cell*, vol. 76, pp. 811–820.
Araki, E., et al, (1994) "Cloning of the Mouse Insulin Receptor Substrate–1 (IRS–1) Gene and Complete Sequence of Mouse IRS–1", *Biochim. Biophys. Acta*, vol. 1221, pp. 353–356.
Araki, E. et al, (1994) "Alternative Pathway of Insulin Signaling in Mice with Targeted Disruption of the IRS–1 Gene", *Nature*, vol. 372, No. 6572, pp. 186–190.
Myers, M.G., et al, (1994) "The IRS–1 signaling system", *Trends in Biochem Sci.*, vol. 19, pp. 289–293.
Wang, L.M., et al, (1993) "IRS–1: Essential for Insulin and IL–4–stimulated Mitogenesis in Hematopoietic Cells", *Science*, vol. 261, pp. 1591–1594.
Taniguchi, T and Minami, Y., (1993) "The IL–2/II–2 Receptor System: A Current Overview", *Cell*, vol. 73, pp. 5–8.
Koettnitz, K. and Kalthoff, F.S. (1993) "Human Interleukin–4 Receptor Signaling Requires Sequences Contained Within Two Cytoplasmic Regions", *Eur. J. Immunol.*, vol. 23, pp. 988–991.
Wang, L.M., et al, (1993) "Common Elements in IL–4 and Insulin Signaling Pathways in Factor Dependent Hematopoietic Cells", *Proceedings of the National Academy of Sciences*, vol. 90, pp. 4032–4036.
Araki, E., et al, (1993) "Human Skeletal Muscle Insulin Receptor Substrate–1: Characterization of the cDNA, Gene and Chromosomal Localization", *Diabetes*, vol. 42, pp. 1041–1054.
Musacchio, A., et al, (1993) "The PH Domain: A Common Piece in the Structural Patchwork of Signaling Proteins", *Trends in Biochem. Sci.*, vol. 18, pp. 343–348.

Myers, M.G. and White, M.F., et al, (1993) "The New Elements of Insulin Signaling Insulin Receptor Substrate–1 and Proteins with SH2 Domains", *Diabetes*, vol. 42, pp. 643–650.
Lee, C.H., et al, (1993) "Nck Associates with the SH2 Domain Docking Protein IRS–1 in Insulin Stimulated Cells", *Proceedings of the National Academy of Sciences*, vol. 90, pp. 11713–11717.
Sun, X J., et al, (1993) "Pleiotropic Insulin Signals Are Engaged by Multisite Phosphorylation of IRS–1", *Molecular and Cellular Biology*, vol. 13, No. 12, pp. 7418–7428.
Wang, L.M., et al, (1992) "IL–4 Activates a Distinct Signal Transduction cascade from IL–3 in Factor Dependent Myeloid Cells", *The EMBO Journal*, vol. 11, pp. 4899–4908.
Harada, N., et al, (1992) "Identification of an Essential Region for Growth Signal Transduction in the Cytoplasmic domain of the Human Interleukin–4 Receptor", *Journal of Biological Chemistry*, vol. 267, No. 32, pp. 22752–22758.
Sun, X J., et al, (1992) "Expression and Function of IRS–1 in Insulin Signal Transmission", *Journal of Biological Chemistry*, vol. 267, No. 31, pp. 22662–22672.
Backer, J.M., et al, (1992) "The Phosphatidylinositol 3'–Kinase is Activated by Association with IRS–1 During Insulin Stimulation", *The EMBO Journal*, vol. 11, pp. 3469–3479.
Myers, M.G., et al, (1992) "IRS–1 Activates Phosphatidylinositol 3'–Kinase by Associating with src Homology 2 Domains of p85", *Proceedings of the National Academy of Sciences*, vol. 89, pp. 10350–10354.
Pawson, T., et al, (1992) "SH2 and SH3 Domains From Structure to Function", *Cell*, vol. 71, pp. 359–362.
Miralpeix, M., et al, (1992) "Insulin Stimulates Tyrosine Phosphorylation of Multiple High Molecular Weight Substrates in Fao Hepatoma Cells", *Biochemistry*, vol. 31, No. 37, pp. 9031–9039.
Sun, X J., et al, (1991) "Structure of the Insulin Receptor Substrate IRS–1 Defines a Unique Signal Transduction Protein", *Nature*, vol. 352, pp. 73–77.
Paul, W.E., (1991) "Interleukin–4: A Prototypic Immunoregulatory Lymphokine", *Blood*, vol. 77, No. 9, pp. 1859–1870.
Koch, C.A., et al, (1991) "SH2 and SH3 Domains Elements that Control Interactions of Cytoplasmic Signaling Proteins", *Science*, vol. 252, pp. 668–674.
Idzerda, R.L., et al, (1990) "Human Interleukin 4 Receptor Confers Biological Responsiveness and Defines a Novel Receptor Superfamily", *J. Exp Med.*, vol. 171, pp. 861–873.
Cosman, D., et al., (1990) "A New Cytokine Receptor Superfamily", *Trends in Biochem Sci.*, vol. 15, pp. 256–270.

(List continued on next page.)

*Primary Examiner*—Paula K. Hutzell
*Assistant Examiner*—Robert C. Hayes
*Attorney, Agent, or Firm*—Louis Myers, Esq.

[57] ABSTRACT

A substantially pure nucleic acid comprising a sequence encoding an IRS-2 polypeptide, a substantially pure preparation of an IRS-2 polypeptide, and related methods.

6 Claims, 27 Drawing Sheets

OTHER PUBLICATIONS

Ferris, D K., et al, (1989) "Comparative Analysis of IL–2 and IL–3 Induced Tyrosine Phosphorylation", *Lymphokine Research*, vol. 8, No. 3, pp. 215–224.

Moria, A.O., et al, (1988) "Hematopoietic Growth Factors Activate the tyrosine phosphorylation of Distinct Sets of Proteins in Interleukin–3–dependent Murine Cell Lines", *Mol. Cell Biol.*, vol. 88, No. 5, pp. 2214–2218.

Sitkovsky, M V., and Paul, W E., (1988) "Global or direct exocytosis?", *Nature*, vol. 332, pp. 306–307.

Pestka, S, and Langer, J A, (1987) "Interferons and their actions", *Biochem.*, vol. 56, pp. 727–777.

White, M.F., et al, (1985) "Insulin rapidly stimulates tyrosine phosphorylation of a $M_r$–185,000 protein in intact cells", *Nature*, vol. 318, pp. 183–186.

White et al, "The Insulin Signalling System" J Biological Chemistry, vol. 269 1–4 (1994).

```
AGACAAGAACTCCTGGAGCCGGACCCGTAGCCTTGGGGGGCTCCTTCGGCA 3894
A-  -  -  -  -  -  -  -  -  -  -  -  -  -  -  -  -  -  -  -  A- -CCACCCCCCTTCCCCTCACCAGCCCTTAGGCA 3621

CCGTCGGAGGCTCTGGCGCCAGCGGAGTGTGTGGGGGCTCCAGGCACTGGA 3944
GCAATGAGGGCAACTCCCAAGACGCTCCAGTGAGGATTTAAGCAACTAT 3671

GCTTTGCCCTCTGCCAGCACCTATGCAAGCATCGACTTCCTGTCCCATCA 3994
GC- - - - - -CAGCATCAGCTTCCAGCAGCAAAGCCAGGATCGTCAATAG 3713

CTTGA-AGGAAGCCACAGTCGTGAAAGAGAGTGAAGCGCTACCAGCCCCATC 4043
CTTAACTGGACGTCACAG- - - - - - - - - - - - - - - - - - - - - - - - - - - - - 3731
                                                    (SEQ ID NO:1)

GCCCGCCATGTTGAAAAAACAAAAACAAAAAAAAAA 4088
- - - - - - - - - - - - - - - - - - - - - - - - - - - - - - - - - - - 3731
                                                    (SEQ ID NO:15)
```

*FIG. 4*
*CONT.*

C1(1r): >u 1>+++++ IRS-2 (4088 bases)+++++>u 4088>
```
   1:CCCCTCGGCC CTCGCCATCC CCTGTTCGCA GCCGGGCAGA GAGACCTGAA GCGGC
  aa:..........  ..........  ..........  ..........  ..........  .....
  56:GGCG ATG GCT AGC GCG CCC CTG CCT GGG CCC CCC GCG TCG GGG GGC
  aa:...  met ala ser ala pro leu pro gly pro pro ala ser gly gly
 102: GGG GAC GGC CCG AAC CTC AAT AAC AAC AAC AAC AAC AAC AAC CAC
  aa: gly asp gly pro asn leu asn asn asn asn asn asn asn asn his
 147: AGC GTG CGC AAG TGC GGC TAG CTG CGC AAG CAG AAG CAC GGC CAC
  aa: ser val arg lys cys gly tyr leu arg lys gln lys his gly his
 192: AAG CGC TTT TTC GTG TTG CGC GGG CCC GGC ACG GGC GGC GAC GAG
  aa: lys arg phe phe val leu arg gly pro gly thr gly gly asp glu
 237: GCA TCC GCG GCT GGG GGG TCG CCG CCG CAG CCT CCG CGG CTG GAG
  aa: ala ser ala ala gly gly ser pro pro gln pro pro arg leu glu
 282: TAC TAC GCG AGC GAG AAG AAG TGG AGG AGC AAG GCG GGC GCG CCG
  aa: tyr tyr glu ser glu lys lys trp arg ser lys ala gly ala pro
 327: AAG CGA GTG ATC GCG CTC GAC TGC TGT CTG AAC ATC AAC AAG CGC
  aa: lys arg val ile ala leu asp cys cys leu asn ile asn lys arg
 372: GCG GAC GCC AAG CAC AAG TAC CTG ATC GCC CTC TAC ACC AAG GAC
  aa: ala asp ala lys his lys tyr leu ile ala leu tyr thr lys asp
 417: GAG TAC TTC GCT GTA GCG GCG GAG AAC GAG CAG GAG CAG GAG GGC
  aa: glu tyr phe ala val ala ala glu asn glu gln glu gln glu gly
 462: TGG TAC CGC GCA CTC ACC GAC TTG GTC AGC GAA GGC CGC TCT GGC
  aa: trp tyr arg ala leu thr asp leu val ser glu gly arg ser gly
 507: GAG GGG GGC TCG GGC ACC ACC GGA GGC TCT TGC AGC GCC TCT CTC
  aa: glu gly gly ser gly thr thr gly gly ser cys ser ala ser leu
 552: CCG GGC GTC CTG GGC GGC TCA GCG GGC GCC GCT GGC TGC GAT GAC
  aa: pro gly val leu gly gly ser ala gly ala ala gly cys asp asp
 597: AAC TAC GGG CTC GTG ACA CCC GCC ACG GCC GTC TAC CGC GAG GTG
  aa: asn tyr gly leu val thr pro ala thr ala val tyr arg glu val
 642: TGG CAG GTG AAC CTG AAA CCT AAG GGA CTG GGC CAG AGC AAG AAC
  aa: trp gln val asn leu lys pro lys gly leu gly gln ser lys asn
 687: CTG ACT GGT GTA TAC CGC CTA TGC CTG TCT GCG CGC ACC ATC GGC
  aa: leu thr gly val tyr arg leu cys leu ser ala arg thr ile gly
 732: TTC GTG AAG CTC AAT TGC GAA CAG CCG TCG GTG ACG CTG CAG CTT
  aa: phe val lys leu asn cys glu gln pro ser val thr leu gln leu
 777: ATG AAC ATT CGC CGC TGC GGC CAC TCG GAC AGC TTC TTC TTC ATC
  aa: met asn ile arg arg cys gly his ser asp ser phe phe phe ile
 822: GAG GTG GGC CGT TCG GCG GTC ACC GGT CCC GGG GAG CTG TGG ATG
  aa: glu val gly arg ser ala val thr gly pro gly glu leu trp met
 867: CAA GCC GAC GAC TCG GTG GTG GCG CAG AAC ATC CAT GAG ACC ATC
  aa: gln ala asp asp ser val val ala gln asn ile his glu thr ile
 912: CTA GAA GCT ATG AAG GCA CTC AAA GAG CTC TTC GAG TTC CGG CCT
  aa: leu glu ala met lys ala leu lys glu leu phe glu phe arg pro
 957: CGC AGC AAG AGT CAG TCG TCC GGG TCG TCA GCC ACG CAT CCC ATC
  aa: arg ser lys ser gln ser ser gly ser ser ala thr his pro ile
1002: AGC GTG CCG GGC GCG CGC CGC CAC CAC CAC CTA GTC AAC CTA CCC
  aa: ser val pro gly ala arg arg his his his leu val asn leu pro
```

*FIG. 6*

```
1047: CCT AGC CAG ACC GGC CTG GTG CGC CGC TCG CGC ACT GAC AGC CTG
  aa: pro ser gln thr gly leu val arg arg ser arg thr asp ser leu
1092: GCG GCC ACC CCC CCA GCA GCC AAG TGC ACT TCG TGC CGG GTT CGT
  aa: ala ala thr pro pro ala ala lys cys thr ser cys arg val arg
1137: ACG GCC AGC GAG GGC GAC GGC GGC GCG GCA GGC GGG GCC GGG ACG
  aa: thr ala ser glu gly asp gly gly ala ala gly gly ala gly thr
1182: GCA GGA GGC AGG CCG ATG TCG GTG GCA GGG AGC CCC CTG AGT CCC
  aa: ala gly gly arg pro met ser val ala gly ser pro leu ser pro
1227: GGG CCG GTG CGC GCG CCC CTT AGC CGC TCG CAC ACC CTG AGC GCC
  aa: gly pro val arg ala pro leu ser arg ser his thr leu ser ala
1272: GGC TGC GGA GGC CGC CCG AGC AAA GTG ACT CTG GCG CCG GCA GGG
  aa: gly cys gly gly arg pro ser lys val thr leu ala pro ala gly
1317: GGA GCC CTG CAA CAC AGC CGC TCC ATG TCC ATG CCC GTG GCG CAC
  aa: gly ala leu gln his ser arg ser met ser met pro val ala his
1362: TCA CCT CCT GCA GCC ACC AGC CCA GGC AGC CTG TCC TCC AGC AGT
  aa: ser pro pro ala ala thr ser pro gly ser leu ser ser ser ser
1407: GGG CAC GGC TCG GGC TCC TAC CCG CTG CCA CCT GGC TCC CAC CCG
  aa: gly his gly ser gly ser tyr pro leu pro pro gly ser his pro
1452: CAC CTG CCT CAT CCA CTG CAT CAC CCC CAA GGC CAG CGT CCG TCC
  aa: his leu pro his pro leu his his pro gln gly gln arg pro ser
1497: AGC GGT AGT GCC TCC GCC TCG GGC TCC CCC ATC GAC CCG GGT TTC
  aa: ser gly ser ala ser ala ser gly ser pro ser asp pro gly phe
1542: ATG TCC CTT GAC GAG TAT GGC TCC AGC CCT GGC GAC CTG AGA GCC
  aa: met ser leu asp glu tyr gly ser ser pro gly asp leu arg ala
1587: TTC AGT AGC CAC AGG AGC AAC ACA CCC GAG TCA ATA GCG GAG ACC
  aa: phe ser ser his arg ser asn thr pro glu ser ile ala glu thr
1632: CCG CCA GCC AGA GAT GGC AGT GGG GGC GAA CTC TAT GGG TAC ATG
  aa: pro pro ala arg asp gly ser gly gly glu leu tyr gly tyr met
1677: AGC ATG GAT AGA CCC CTG AGC CAC TGT GGC CGC CCT TAC CGT AGG
  aa: ser met asp arg pro leu ser his cys gly arg pro tyr arg arg
1722: GTC TCA GGG GAT GGG GCC CAG GAC CTG GAT AGA GGA CTG AGG AAG
  aa: val ser gly asp gly ala gln asp leu asp arg gly leu arg lys
```

FIG. 6
CONT.

```
1767: AGG ACT TAT TCC CTA ACC ACG CCT GCC AGG CAG CGG CAG GTA CCT
  aa: arg thr tyr ser leu thr thr pro ala arg gln arg gln val pro
1812: CAG CCT TCC TCT GCC TCT CTA GAT GAA TAC ACT CTC ATG AGG GCC
  aa: gln pro ser ser ala ser leu asp glu tyr thr leu met arg ala
1857: ACC TTC TCT GGT AGT TCA GGT CGC CTC TGC CCA TCC TTC CCT GCG
  aa: thr phe ser gly ser ser gly arg leu cys pro ser phe pro ala
1902: TCC TCT CCC AAA GTG GCC TAC AAC CCT TAC CCA GAG GAC TCT GGA
  aa: ser ser pro lys val ala tyr asn pro tyr pro glu asp tyr gly
1947: GAC ATT GAG ATT GGT TCT CAC AAG AGT TCC AGC AGT AAC CTG GGG
  aa: asp ile glu ile gly ser his lys ser ser ser ser asn leu gly
1992: GCA GAT GAT GGC TAC CTG CCC ATG ACC CCT GGG GCA GCC CTT AGG
  aa: ala asp asp gly tyr met pro met thr pro gly ala ala leu arg
2037: AGT GGT GGT CCC AAT AGC TGC AAG AGC GAT GAC TAC ATG CCC ATG
  aa: ser gly gly pro asn ser cys lys ser asp asp tyr met pro met
2082: AGC CCC ACA AGC GTG TCT GCT CCC AAG CAG ATC CTG CAG CCA CGC
  aa: ser pro thr ser val ser ala pro lys gln ile leu gln pro arg
2127: TTG GCA GCG GCC TTG CCC CCT TCC GGA GCA GCC GTG CCA GCA CCC
  aa: leu ala ala ala leu pro pro ser gly ala ala val pro ala pro
2172: CCT TCA GGG GTG GGC AGG ACC TTC CCA TGA AAC GGA GGT GGC TAC
  aa: pro ser gly val gly arg thr phe pro val asn gly gly gly tyr
2217: AAA GCC AGC TCC CCA GCG GAG AGC TCC CCA GAA GAC AGT GGG TAC
  aa: lys ala ser ser pro ala glu ser ser pro glu asp ser gly tyr
2262: ATG CGA ATG TGG TGT GGC TCC AAG CTG TCT ATG GAG AAC CCA GAC
  aa: met arg met trp cys gly ser lys leu ser met glu asn pro asp
2307: CCT AAG CTA CTC CCC AAC GGG GAC TAC CTC AAC ATG TCC CCC AGC
  aa: pro lys leu leu pro asn gly asp tyr leu asn met ser pro ser
2352: GAG GCA GGC ACT GCA GGG ACC CCA CCT GAC TTC TCA GCA GCT TTG
  aa: glu ala gly thr ala gly thr pro pro asp phe ser ala ala leu
2397: CGT GGA GGC AGT GAA GGC CTC AAA GGC ATC CCG GGC CAC TGC TAC
  aa: arg gly gly ser glu gly leu lys gly ile pro gly his cys tyr
2442: AGC TCT TTG CCC CGC TCT TAT AAG GCT CCC TGT TCC TGC AGC GGA
  aa: ser ser leu pro arg ser tyr lys ala pro cys ser cys ser gly
2487: GAG AAT GAC CAG TAT GTG CTC ATG AGC TCC CCT GTG GGC CGG ATC
  aa: asp asn asp gln tyr val leu met ser ser pro val gly arg ile
```

FIG. 6
CONT.

```
2532: TTG GAA GAG GAG AGA CTG GAG CCC CAG GCC ACC CCA GGG GCT GGC
  aa: leu glu glu glu arg leu glu pro gln ala thr pro gly ala gly
2577: ACC TTT GGG GCA GCT GGT GGT AGT CAT ACC CAG CCT CAT CAC TCA
  aa: thr phe gly ala ala gly gly ser his thr gln pro his his ser
2622: GCA GTG CCT TCC TCC ATG AGG CCG AGT GCC ATC GGT GGC CGC CCT
  aa: ala val pro ser ser met arg pro ser ala ile gly gly arg pro
2667: GAG GGC TTC CTG GGC CAG CGA TGT CGG GCA GTG CGG CCT ACA CGC
  aa: glu gly phe leu gly gln arg cys arg ala val arg pro thr arg
2712: CTA TCG CTA GAG GGA CTG CAG ACC CTT CCC AGC ATG CAA GAG TAC
  aa: leu ser leu glu gly leu gln thr leu pro ser met gln glu tyr
2757: CCT CTA CCC ACA GAG CCC AAG AGC CCT GGC GAG TAC ATC AAC ATT
  aa: pro leu pro thr glu pro lys ser pro gly glu tyr ile asn ile
2802: GAC TTT GGT GAG GCA GGT ACC CGT CTG TCT CCG CCT GCC CCC CCA
  aa: asp phe gly glu ala gly thr arg leu ser pro pro ala pro pro
2847: CTA CTG GCA TCC GCG GCC TCA TCT TCT TCA CTG CTC TCA GCT AGT
  aa: leu leu ala ser ala ala ser ser ser ser leu leu ser ala ser
2892: AGT CCT GCT TCA TCC CTG GGT TCA GGA ACC CCA GGC ACC AGC AGC
  aa: ser pro ala ser ser leu gly ser gly thr pro gly thr ser ser
2937: GAC AGC CGG CAG CGC TCT CCA CTC TCT GAC TAT ATG AAC CTG GAC
  aa: asp ser arg gln arg ser pro leu ser asp tyr met asn leu asp
2982: TTC AGT TCT CCC AAG TCC CCC AAG CCT AGC ACC CGC AGT GGG GAC
  aa: phe ser ser pro lys ser pro lys pro ser thr arg ser gly asp
3027: ACA GTA GGC TCC ATG GAT GGC CTT CTC TCT CCA GAG GCT TCA TCC
  aa: thr val gly ser met asp gly leu leu ser pro glu ala ser ser
3072: CCA TAC CCA CCA CTG CCC CCA CGT CCT TCC ACT TCC CCT TCC TCC
  aa: pro tyr pro pro leu pro pro arg pro ser thr ser pro ser ser
3117: TTA CAG CAG CCT CTG CCA CCT GCC CCG GGA GAC CTA TAC CGC CTG
  aa: leu gln gln pro leu pro pro ala pro gly asp leu tyr arg leu
3162: CCT CCA GCA TCA GCT GCC ACT TCC CAG GGT CCC ACT GCT GGC TCC
  aa: pro pro ala ser ala ala thr ser gln gly pro thr ala gly ser
3207: TCA CTG TCC TCC GAG CCT GGG GAT AAT GGT GAC TAT ACC GAG ATG
  aa: ser met ser ser glu pro gly asp asn gly asp tyr thr glu met
3252: GCC TTT GGT GTG GCT GCA ACC CCG CCA CAA CCT ATC GTG GCA CCT
  aa: ala phe gly val ala ala thr pro pro gln pro ile val ala pro
3297: CCA AAG CCA GAA GGT GCC CGA GTG GCC AGT CCC ACA TCG GGC TTG
  aa: pro lys pro glu gly ala arg val ala ser pro thr ser gly leu
3342: AAG CGG CTA AGT CTC ATG GAT CAG GTA TCT GGG GTG GAG GCT TTC
  aa: lys arg leu ser leu met asp gln val ser gly val glu ala phe
3387: CTT CAA GTC AGC CAG CCC CCT GAC CCC CAC CGG GGT GCT AAG GTC
  aa: leu gln val ser gln pro pro asp pro his arg gly ala lys val
```

FIG. 6
*CONT.*

```
3432: ATC CGT GCA GAC CCA CAG GGG GGA CGT CGT CGC CAC AGT TCA GAG
  aa: ile arg ala asp pro gln gly gly arg arg arg his ser ser glu
3477: ACC TTT TCC TCT ACC ACC ACC GTC ACC CCA GTG TCC CCA TCC TTT
  aa: thr phe ser ser thr thr thr val thr pro val ser pro ser phe
3522: GCC CAC AAT TCC AAG CGC CAC AAT TCG GCC TCT GTG GAA AAT GTC
  aa: ala his asn ser lys arg his asn ser ala ser val glu asn val
3567: TCA CTC AGG AAA AGC AGT GAA GGC AGC AGT ACC CTG GGA GGA GGT
  aa: ser leu arg lys ser ser glu gly ser ser thr leu gly gly gly
3612: GAT GAG CCG CCC ACA TCC CCA GGA CAG GCA CAG CCC TTG GTG GCT
  aa: asp glu pro pro thr ser pro gly gln ala gln pro leu val ala
3657: GTG CCC CCA GTG CCA CAG GCT AGG CCG TGG AAC CCC GGT CAG CCC
  aa: val pro pro val pro gln ala arg pro trp asp pro gly gln pro
3702: GGA GCT TTG ATT GGC TGT CCT GGA GGC AGC AGT TCT CCC ATG CGC
  aa: gly ala leu ile gly cys pro gly gly ser ser ser pro met arg
3747: AGA GAG ACC TCC GTG GGT TTC CAG AAC GGC CTC AAC TCT ATC GCC
  aa: arg glu thr ser val gly phe gln asn gly leu asn tyr ile ala
3792: ATC GAT GTG AGA GGC GAG CAG GGG TCC TTG GCG CAG TCT CAG CCG
  aa: ile asp val arg gly glu gln gly ser leu ala gln ser gln pro
3837: CAG CCA GGA GAC AAG AAC TCC TGG AGC CGG ACC CGT AGC CTT GGG
  aa: gln pro gly asp lys asn ser trp ser arg thr arg ser leu gly
3882: GGG CTC CTC GGC ACC GTC GGA GGC TCT GGC GCC AGC GGA GTG TGT
  aa: gly leu leu gly thr val gly gly ser gly ala ser gly val cys
3927: GGG GGT CCA GGC ACT GGA GCT TTG CCC TCT GCC AGC ACC TAT GCA
  aa: gly gly pro gly thr gly ala leu pro ser ala ser thr tyr ala
3972: AGC ATC GAC TTC CTG TCC CAT CAC TTG AAG GAA GCC ACA GTC GTG
  aa: ser ile asp phe leu ser his his leu his glu ala thr val val
4017: AAA GAG TGA AGCGCTACCAGCCCC ATCGCCGCCA TGTTGAAAAA AACAAAAA
  aa: lys glu ***  ....  ..........  ..........  .......(SEQ ID NO:1)
4069: CA AAAACAAAAA AAAAAAAA (SEQ ID NO:1)
  aa: ..  ..........  ........
```

```
IRS-2      SFFFIEVGRSAVTGPGELWMQ ADDSVVAQNI HETILEAMKALKE LF EFRP   299
IRS-1      NFFFIEVGRSAVTGPGEFWMQ VDDSVVAQNM HETILEAMRAMS D-  EFRP   261
CONCENSUS  -FFFIEVGRSAVTGPGE-WMQ-DDSVVAQN-HETILEAM-A------EFRP      300

IRS-2      RSKSQSSG SSATH PISVPGA RRHHLVN LPPSQTGLV RRSRTDSL AAT PP   349
IRS-1      RSKSQSS- SSSCSN PISVP-- LRRHHLNN PPPSQVGLT RRSRTESI TATS P   308
CONCENSUS  RSKSQSS--SS----PISVP---R-HHL-N-PPSQ--GL-RRSRT--S---AT--P   350

IRS-2      A----AKCTS CRVRTAS EGDGGAAGGAGTAGG RPMSVAGSPL SPGPV RAP    395
IRS-1      ASMVGG KPGS FRVRAS SDGEGTM------ SRPASVDGSPV SPSTN RTH    350
CONCENSUS  A------K--S-RVR---S--G-G--------RP-SV-GSP-SP---R--       400

IRS-2      LS RSHTL SAGCGGRPSKVTLAPAGGAL QHSRSM SMPVAHS PPAATSPGSL   445
IRS-1      AH RHRGSS--------------- RLHPPL NHSRSI PMPSSRCSP SATSPVS L   387
CONCENSUS  --R-----S------------------L-HSRS--MP------P-ATSP-SL      450

IRS-2      SSS SGHGSGSY PLPPGS HPHL P HHPQGQRPSSG SASA SGSPSD DPGFM   495
IRS-1      SSSS TSGHGS----- TSDCLFPRR-------- SSASV SGSPSD GGFI       421
CONCENSUS  SSSS--G-GS------------------P--------SAS-SGSPSD-GF-       500
```

| | | | |
|---|---|---|---|
| IRS-2 | SLDEYGSSPGDLRAFSSHRSNTPESIAETPPARDGSGGELYGYMSMDRP- | 544 |
| IRS-1 | SSDEYGSSPCDFR--SSFRSVTPDSLGHTPPARG--EEELSNYICMGGKG | 467 |
| CONSENSUS | S-DEYGSSP-D-R--SS-RS-TP-S---TPPAR------EL--Y--M--- | 550 |
| IRS-2 | ----LSHCGRPYRRVSG-------DGAQDLDRGLR | 568 |
| IRS-1 | ASTLAAPNGHYILSRGGNGHRYIPGANLGTSPALPGDEAAGADLDNRFR | 517 |
| CONSENSUS | ---------G--------G-------GA-DLD---R | 600 |
| IRS-2 | KRTYSLTTPA---RQRQVPQPSSASLDEYT-LMRATF---SGSSGRLCPS | 611 |
| IRS-1 | KRTHSAGISPTISHQKTPSQSSVASIEEYTEMMPAAYPPGGGSGGRL-PG | 566 |
| CONSENSUS | KRT-S---T------Q------Q--S-AS--EYT--M--A------GS-GRL-P- | 650 |
| IRS-2 | FPASSPKVAYNPYPEDYGDIE----IGSHKSSSNLGADDGYMPMTPGA | 656 |
| IRS-1 | YRH-SAFVPTHSYPEEGLEMHHLERRGGHHRPDTSNLHTDDGYMPMSPGV | 615 |
| CONSENSUS | ----S----V----YPE---------G-H-----SNL--DDGYMPM-PG- | 700 |
| IRS-2 | ALRSGGPNSCKSDDYMPMSPTSVSAPKQILQP--RLAAALPPSGAAVPAP | 704 |
| IRS-1 | A--PVPSNRKGNGDYMPMSPKSVSAPQQIINPIRRHPQRVDPNGYMMMSP | 663 |
| CONSENSUS | A-------N------DYMPMSP-SVSAP-QI--P--R------P--G----P | 750 |

FIG. 7
CONT.

```
IRS-2       PSGVGRTFPVN GGG GYKASSPAESS PED SGYMRMWCGS----------·K  742
IRS-1       SGSCSPDI--- GGG SSSSISAAPSG SGS SYGKPWTNGVGGHHTHALPHAK  710
CONCENSUS   ---------·· GGG ----SS·---- ··· -·······P··S·Y····K  800

IRS-2       LSMENPDPKLLP-NGDYLNMSP SEAGTAGTPP PDF SAALRG GS EGLKG IPG  791
IRS-1       PPVE SGGGKLLP CTGDYMNMSP VGDSNTSSPS ECYY---  GP EDPQHK PV  756
CONCENSUS   ····E····KLLP··GDY·NMSP·········P·····G·E······P·  850

IRS-2       HCY SSLPRSYKAPCSCS---GDNDQ YVLMSSP VGRI---· LEEERLEP  832
IRS-1       LS Y YSLPRSFK HTQRPGEPEE GA RHQ HLRLSSS GRL RYTATAED SSSST  806
CONCENSUS   ··Y·SLPRS·K········G······Q······SS··GR·······E····  900

IRS-2       QATPGAGT FGAA--GG SHTQPHHSAVPSS MRPSAIGGRPEGFLGQRC RAV  880
IRS-1       SSDSLGG GG YCGA RPES SLT HPHHHVLQPHL PRKVDTAAQTN----S R LA  851
CONCENSUS   ·······G··················S··T·PHH··············R·  950

IRS-2       --- TLPSMQEYPL-------- PTEPKSPGEYINIDFGEAGT  921
IRS-1       LGDPKAS TLPRVRE QQQQQQSSLHP PEPKSPGEYVNIEFGSG----  899
CONCENSUS   ·········TLP···E·············P·EPKSPGEY·NI·FG----  1000
```

```
IRS-2      R L S P P A P P L L A S A A S S L L S A S S P A S S L G S G T P G T S S D S R Q R S P L S D Y M  971
IRS-1      . . . . Q P G Y L A G P A T S R S S P S V R C P P Q L H P A P R E E T G S E . . . . . . E Y M  936
CONCENSUS  . . . . . . . . P . . L A . . A . S . . . . . S . . . . . . . . . P . . . . . . . . . T . S . . Y M  1050

IRS-2      N L D F S S P K P S P K P S T R S G D T V G S M D G L L S P E A S S P Y P P L P P R P S T S P S S L Q  1021
IRS-1      N M D L G P G R R A T W Q E S G G V E L G R I G P . . . . . . . . . . A P P G S A T V C R P T  973
CONCENSUS  N . D . . . . . . . . . . . . G . . . G . . . . . . . . . . . . . . . . . . . . P . . S . . . . . . . . . . 1100

IRS-2      Q P L P P A P G D L Y R L P P A S A A T S Q G P T A G S S M S S . . . E P G D N G D Y T E M A F G  1067
IRS-1      R S V P N S R G D Y M T M Q I G C P R Q S Y V D T S P V A P V S Y A D M R T G I A A E K A S L P R P  1023
CONCENSUS  . . . P . . . G D . . . . . . . . . . . . . . . . G . . . . . . . . . S . . . . . . . . . . . . . . G . . . 1150

IRS-2      V A A T P P Q P I V A P P K P E G A R V A S P T S G L K R L S L M . . . D Q V S G V E A F L Q V S Q  1114
IRS-1      T G A A P P P S S T A S S S A S V T P Q G A T A E Q A T H S S L L G G P Q G P G G M S A F T R V N L  1073
CONCENSUS  . . . . . . . . . A . P P . . . . . . . . . A . . . . . . . . . . . . . . . . . . . . S L . . . G . . . . . A F . . . V . . 1200

IRS-2      P P D P H R G A K V I R A D P Q G G R R R H S S E T F S S T T T V T P V S P S F A . . . . . . . . . 1155
IRS-1      S P N H N Q S A K V I R A D T Q G C R R R H S S E T F S A P T R A G N T V P F G A G A A V G G S G G 1123
CONCENSUS  P . . . . . . . A K V I R A D . Q G . R R R H S S E T F S . . T . . . . . . . . . . . . P . . A . . . . . . . . . 1250
```

```
IRS-2      - - - - - H N S K R H N S A S V E N V S L R K S S E G S S T L G G G D E P P T S P G Q A Q P L V A   1199
IRS-1      G G G G G S E D V K R H S S A S F E N V W L R P G D L G - - - G V S K E S A P V C G A A - - - - -   1164
CONCENSUS  - - - - - - - - K R H - S A S - E N V - L R - - - - - G - - - - - - - E - - - - G - A - - - - -   1300

IRS-2      V P P V P Q A R P W N P G Q P G A L I G C P G G S S S P M R R E T S V G F Q N G L N Y I A I D V R G   1249
IRS-1      - - - - - - - - - - - - - - - - - - - - - - - - - - - - - - - G G L E K S L N Y I D L D L A K     1180
CONCENSUS  - - - - - - - - - - - - - - - - - - - - - - - - - - - - - - - G - - - - - L N Y I - - - D - - - -   1350

IRS-2      E Q G S L A Q S Q P Q P G D K N S W S R T R S L G G L L G T V G G S G A S G V C G G P G T G A L P S   1299
IRS-1      E - - - - H S Q D C P S Q Q Q S L P P P P H Q P L G S N E G N S P R R S S - - - - - - E D           1216
CONCENSUS  E - - - - - - - S Q - - - P - - - - - - S - - - - - - - - - - - - G - - - - - - - - - - - - - -   1400

IRS-2      A S T Y A S I D F L S H H L K E A T V V K E X                                                       1322
IRS-1      L S N Y A S I S F Q K Q P E D R Q X - - - - -                                                       1234
CONCENSUS  - S - Y A S I - F - - - - - - - - - - - - - -                                                       1423
```

IRS-2                   (SEQ ID NO:1)
IRS-1                   (SEQ ID NO:15)
CONCENSUS               (SEQ ID NO:16)

FIG. 7 CONT.

DNA ENCODING AN INSULIN RECEPTOR SUBSTRATE

This invention was made with government support from the National Institute of Health. Accordingly, the government retains certain rights in the invention.

BACKGROUND OF THE INVENTION

The invention relates to IRS genes, e.g., to IRS-2, which encodes a protein which is a substrate for several molecules, e.g., the insulin receptor, the IL-4 receptor and the IL-15 receptor.

SUMMARY OF THE INVENTION

The inventors have discovered IRS-2, insulin receptor substrate-2. They have also discovered the existence of a family of IRS-2-like genes, which share functional and structural properties.

Accordingly, the invention features a purified preparation of an IRS polypeptide, or a recombinant IRS peptide, having one or more of the following characteristics:

(i) the IRS polypeptide includes at least one IRS-common-tyrosine-containing phosphorylation site (IRS-CPS);

(ii) the IRS polypeptide includes at least one IRS homology domain (IH) chosen from the group of: IRS homology domain 1 (IH1), IRS homology domain 2 (IH2), and IRS homology domain 3 (IH3);

(iii) the IRS polypeptide can bind with the insulin receptor, and can be phosphorylated by the insulin receptor;

(iv) the IRS polypeptide can bind with the IL-4 receptor complex, and can be phosphorylated by the IL-4 receptor complex; and (v) the IRS polypeptide can bind with the IL-15 receptor complex, and can be phosphorylated by the IL-15 receptor complex; and (vi) the IRS polypeptide can bind an SH2 domain containing protein.

In preferred embodiments, the IRS polypeptide is other than IRS-1.

In preferred embodiments, the IRS polypeptide includes: 1, 2, 3, 4, 5, 6, 7, 8, 9, 10, 11, 12, or 13 IRS-CPS's; IRS-CPS 1 and 2; IRS-CPS 3; IRS-CPS 8; IRS-CPS 9; IRS-CPS 10; IRS-CPS 11; at least 5 or 10 IRS-CPS's.

In preferred embodiments, the IRS polypeptide further includes tyrosine containing phosphorylation sites other than IRS-CPS's, i.e., non-common sites. Non-common sites can be present in IH domains, e.g., in IH1, IH2, or IH3, or in other regions. In preferred embodiments: one or more non-common sites will be in the C-terminal region; the IRS polypeptide contains at least 1, 2, 3, 4, 5, 6, 7, 8, or 9 non-common sites.

In preferred embodiments, the sequence of the four amino acids on each side of a tyrosine of a IRS-CPS is essentially the same, or differs by only 1 or 2 residues, from the sequence of a site shown in FIG. 8. In other embodiments, the location of the tyrosine(s) is essentially the same as in FIG. 8, but the four amino acids on each side of a tyrosine of a IRS-CPS are completely or mostly different.

In preferred embodiments, the IRS polypeptide includes: IH1; IH2; IH3; IH1 and IH3; IH1 and IH2; IH2 and IH3; IH1, IH2, and IH3.

In preferred embodiments, the IRS polypeptide binds with: the insulin receptor; the interleukin 4 receptor; the interleukin 13 receptor; the insulin-like growth factor receptor; or the IL-15 receptor.

In preferred embodiments, the IRS polypeptide binds with a SH2 domain containing protein, e.g., PI 3'-kinase, Grb-2, SH-PTP-2, nck, or c-fyn.

In preferred embodiments the IRS polypeptide has a molecular weight of about 165–190 kd, as determined by SDS-PAGE.

In another aspect, the invention features an IRS-2 polypeptide, preferably a substantially pure preparation of an IRS-2 polypeptide, or a recombinant IRS-2 polypeptide. In preferred embodiments: the polypeptide has biological activity, e.g., it specifically binds the insulin receptor; it binds to the PI 3'-kinase (preferably to the SH2 region of PI 3'-kinase) after ligand (e.g., insulin, IGF-1 or IL-4) stimulation; it is phosphorylated by the insulin receptor or other tyrosine kinases; the polypeptide has an amino acid sequence at least 40%, 50%, 60%, 80%, 90%, 95%, or 99% homologous to the amino acid sequence in SEQ ID NO:1; the polypeptide has an amino acid sequence essentially the same as the amino acid sequence in SEQ ID NO:1; the polypeptide is at least 5, 10, 20, 50, 100, or 150 amino acids in length; the polypeptide comprises at least 5, preferably at least 10, more preferably at least 20, more preferably at least 50, 100, 150, 500, 750, or 1,000 contiguous amino acids from SEQ ID NO:1; the IRS-2 polypeptide is either, an agonist or an antagonist of a biological activity of a naturally occurring IRS-2, e.g., PI 3'-kinase, p70sbk agonists.

In preferred embodiments the invention includes an IRS-2 polypeptide with biological activity, e.g., a polypeptide capable of: binding to the insulin receptor; binding to the PI 3'-kinase (preferably to the SH2 region of PI 3'-kinase) after ligand (e.g., insulin, IGF-1 or IL-4) stimulation; being phosphorylated by the insulin receptor or other tyrosine kinases.

In a preferred embodiment, the invention includes a peptide having at least one biological activity of the subject IRS-2 polypeptide which differs in amino acid sequence at one, two, three, five or ten residues, from the sequence in SEQ ID NO:1.

Yet other preferred embodiments include: an IRS-2 polypeptide which is a recombinant fusion protein which includes a second polypeptide portion, e.g., a second polypeptide having an amino acid sequence unrelated to a protein represented by one of SEQ ID NO:1. The second polypeptide portion can be, e.g., glutathione-S-transferase, a DNA binding domain, a polymerase activating domain. In preferred embodiments the fusion protein is functional in a two-hybrid assay.

Yet other preferred embodiments include: a polypeptide homologous to SEQ ID NO:1, the polypeptide having a molecular weight of approximately 165 to 190 kilodaltons, e.g. a molecular weight of about 170 or 180 kD, as determined by SDS-PAGE.

In another aspect, the invention features an immunogen including an IRS-2 polypeptide in an immunogenic preparation, the immunogen being capable of eliciting an immune response specific for the IRS-2 polypeptide; a humoral response, e.g., an antibody response; or a cellular response. In preferred embodiments, the immunogen includes an antigenic determinant, e.g. a unique determinant, from a protein represented by SEQ ID NO:1.

In another aspect, the invention features an antibody preparation, e.g., a monoclonal antibody preparation, specifically reactive with an IRS-2 polypeptide. In preferred embodiments: the antibody does not react with IRS-1; the antibody is specific for a site on IRS-2 other than a phosphotyrosine residue.

In another aspect, the invention features a substantially pure IRS nucleic acid which encodes an IRS polypeptide having one or more of the following characteristics:

(i) the IRS encoded polypeptide includes at least one IRS-common-tyrosine-containing-phosphorylation site (IRS-CPS);

(ii) the IRS encoded polypeptide includes at least one IRS homology domain (IH) chosen from the group of: IRS homology domain 1 (IH1), IRS homology domain 2 (IH2), and IRS homology domain 3 (IH3);

(iii) the IRS encoded polypeptide can bind with the insulin receptor, and can be phosphorylated by the insulin receptor; and (iv) the IRS encoded polypeptide can bind with the IL-4 receptor complex, and can be phosphorylated by the IL-4 receptor;

(v) the IRS encoded polypeptide can bind with the IL-15 receptor complex, and can be phosphorylated by the IL-15 receptor complex; and (vi) the IRS encoded polypeptide can bind an SH2 domain containing protein.

In preferred embodiments, the IRS encoded polypeptide is other than IRS-1.

In preferred embodiments, the IRS encoded polypeptide includes: 1, 2, 3, 4, 5, 6, 7, 8, 9, 10, 11, 12, or 13 IRS-CPS's; IRS-CPS 1 and 2; IRS-CPS 3; IRS-CPS 8; IRS-CPS 9; IRS-CPS 10; IRS-CPS 11; at least 5 or 10 IRS-CPS's.

In preferred embodiments, the IRS encoded polypeptide further includes tyrosine containing phosphorylation sites other than IRS-CPS's, i.e., non-common sites. Non-common sites can be present in IH domains, e.g., in IH1, IH2, or IH3, or in other regions. In preferred embodiments: one or more non-common sites will be in the C-terminal region; the IRS encoded polypeptide contains at least 1, 2, 3, 4, 5, 6, 7, 8, or 9 non-common sites.

In preferred embodiments, the sequence of the four amino acids on each side of a tyrosine of a IRS-CPS is essentially the same, or differs by only 1 or 2 residues, from the sequence of a site shown in FIG. 8. In other embodiments, the location of the tyrosine(s) is essentially the same as in FIG. 8, but the four amino acids on each side of a tyrosine of a IRS-CPS are completely or mostly different.

In preferred embodiments, the IRS encoded polypeptide includes: IH1; IH2; IH3; IH1 and IH3; IH1 and IH2; IH2 and IH3; IH1, IH2, and IH3.

In preferred embodiments, the IRS encoded polypeptide binds with: the insulin receptor; the interleukin 4 receptor; the interleukin 13 receptor; the insulin-like growth factor receptor; or the IL-15 receptor.

In preferred embodiments, the IRS encoded polypeptide binds with a SH2 domain containing protein, e.g., PI 3'-kinase, Grb-2, SH-PTP-2, nck, or c-fyn.

In preferred embodiments the IRS polypeptide has a molecular weight of about 165–190 kd, as determined by SDS-PAGE.

In another aspect, the invention features a substantially pure nucleic acid having a nucleotide sequence which encodes an IRS-2 polypeptide. In preferred embodiments: the encoded polypeptide has biological activity, e.g., it specifically binds the insulin receptor; it binds to the PI 3'-kinase (preferably to the SH2 region of PI 3'-kinase) after ligand (e.g., insulin, IGF-1 or IL-4) stimulation; it is phosphorylated by the insulin receptor or other tyrosine kinases; the encoded polypeptide has an amino acid sequence at least 40%, 50%, 60%, 80%, 90%, 95%, or 99% homologous to the amino acid sequence in SEQ ID NO:1; the encoded polypeptide has an amino acid sequence essentially the same as the amino acid sequence in SEQ ID NO:1; the encoded polypeptide is at least 5, 10, 20, 50, 100, or 150 amino acids in length; the encoded polypeptide comprises at least 5, preferably at least 10, more preferably at least 20, more preferably at least 50, 100, 150, 500, 750, or 1,000 contiguous amino acids from SEQ ID NO:1; the encoded IRS-2 polypeptide is either, an agonist or an antagonist of a biological activity of an IRS-2, e.g., PH 3'-kinase, p70sbk agonists.

In preferred embodiments the encoded polypeptide has biological activity, e.g., the encoded polypeptide is capable of: binding to the insulin receptor; binding to the IL-4 receptor; binding to the PI 3'-kinase (preferably to the SH2 region of PI 3'-kinase) after ligand (e.g., insulin, IGF-1 or IL-4) stimulation; being phosphorylated by the insulin receptor or other tyrosine kinases.

In a preferred embodiment, the invention includes an encoded peptide having at least one biological activity of the subject IRS-2 polypeptide which differs in amino acid sequence at one, two, three, five, or ten residues, from the sequence in SEQ ID NO:1.

In yet other preferred embodiments: the encoded polypeptide is a recombinant fusion protein which includes a second polypeptide portion, e.g., a second polypeptide having an amino acid sequence unrelated to a protein represented by one of SEQ ID NO:1. The second polypeptide portion can be, e.g., glutathione-S-transferase, a DNA binding domain, a polymerase activating domain. In preferred embodiments the fusion protein is functional in a two-hybrid assay.

In other preferred embodiments, the IRS-2 nucleic acid includes a transcriptional regulatory sequence, preferably a sequence other than the IRS-2 regulatory sequence. The transcriptional regulatory sequence can include a transcriptional promoter or a transcriptional enhancer sequence. In preferred embodiments the sequence is operably linked to the IRS-2 gene sequence, e.g., to render the IRS-2 gene sequence suitable for use as an expression vector.

In preferred embodiments, the nucleic acid hybridizes under stringent conditions to a nucleic acid probe corresponding to at least 12 consecutive nucleotides of SEQ ID NO:1; more preferably to at least 20 consecutive nucleotides of SEQ ID NO:1; more preferably to at least 40 consecutive nucleotides of SEQ ID NO:1.

In another aspect, the invention includes: a vector including a nucleic acid which encodes an IRS polypeptide (preferably other than IRS-1), e.g., an IRS-2 polypeptide; a host cell transfected with the vector; and a method of producing a recombinant IRS polypeptide (preferably other than IRS-1), e.g., an IRS-2 polypeptide, including culturing the cell, e.g., in a cell culture medium, and isolating the IRS polypeptide (preferably other than IRS-1), e.g., an IRS-2 polypeptide, e.g., from the cell or from the cell culture medium.

In another aspect, the invention features a preparation of cells, e.g., cells having an IRS transgene (preferably other than IRS-1), e.g., an IRS-2 transgene, or cells which misexpresses an IRS (preferably other than IRS-1), e.g., IRS-2. The cell preparation can consist of human or non-human cells, e.g., rodent cells, e.g., mouse or a rat cells, rabbit cells, or pig cells. In preferred embodiments, the cells include (and preferably express) a heterologous form of the IRS-2 gene, e.g., a transgene, e.g., a gene derived from humans (in the case of a non-human cell), or a gene which misexpresses an exogenous or an endogenous IRS-2 gene. In preferred embodiments: the cells include a lesion which results in the misexpression of an insulin responsive gene other than IRS-2, e.g., IRS-1; the cells include a transgene for an insulin responsive gene other than IRS-2, e.g., IRS-1, and preferably the transgene is misexpressed. Cells of the invention can serve as a model for studying insulin related disorders, e.g., an insulin resistant insulin related disease, e.g., type II diabetes, an immune disorder, a disorder characterized by unwanted cell proliferation, or any disorder characterized by the mutation, or misexpression of IRS-2, IRS-1, or both. As is discussed herein such cells can also be used for drug screening.

In another aspect, the invention features a transgenic non-human animal, e.g., a rodent, e.g., a mouse or a rat, a rabbit, or a pig, having an IRS (preferably other than IRS-1) transgene, e.g., an IRS-2 transgene. In preferred embodiments, the animal includes (and preferably expresses) a heterologous form of the IRS-2 gene, e.g., a gene derived from humans, or a gene which misexpresses an exogenous or an endogenous IRS-2 gene. In preferred embodiments: the animal further includes a lesion which results in the misexpression of an insulin responsive gene other than IRS-2, e.g., IRS-1; the animal further includes a transgene for an insulin responsive gene other than IRS-2, e.g., IRS-1, and preferably the transgene is misexpressed. Transgenic animals of the invention can serve as a model for studying insulin related disorders, e.g., an insulin resistant insulin related disease, e.g., type II diabetes, an immune disorder, a disorder characterized by unwanted cell proliferation, or other disorders characterized by mutation or misexpression of IRS-2, IRS-1, or both. As is discussed herein such animals can also be used for drug screening.

In another aspect, the invention features a non-human animal useful, e.g., as an animal model for a disorder, e.g., an insulin related disorder, e.g., an insulin resistant insulin related disease, e.g., type II diabetes, an immune disorder, or a disorder characterized by unwanted cell proliferation. In preferred embodiments the non-human animal has a mutated or misexpressed IRS gene (preferably other than IRS-1), e.g., an IRS-2 gene. In preferred embodiments the non-human animal is: a mammal, e.g., a rodent, e.g., a mouse or a rat, a rabbit, or a pig. In preferred embodiments: the mutated gene includes a gross chromosomal rearrangement, e.g., a deletion, duplication, inversion, or translocation; a point mutation; the mutated or misexpressed gene is the IRS-2 gene. In preferred embodiments, the non-human animal further includes a second gene which is mutated or misexpressed. The second gene can be an insulin responsive gene, e.g., an IRS-1 gene. The first, second, or both genes can be transgenes, e.g., knockouts.

In another aspect, the invention features a method of determining if a subject is at risk for a disorder, e.g., an insulin-related disease, e.g., an insulin resistant insulin-related disease, e.g., Type II diabetes, or an immune disorder, or a disorder characterized by unwanted cell proliferation. The subject can be a mammal, e.g., a human. In preferred embodiments the disorder is characterized by an abnormality in the structure or metabolism of an IRS gene (preferably other than IRS-1), e.g., IRS-2. In the case where the disorder is related to IRS-2, the method includes: evaluating an aspect of IRS-2 metabolism in the mammal, an abnormal level of IRS-2 metabolism being diagnostic of the disorder. Preferred embodiments include those in which: the evaluation includes measuring the level of IRS-2 protein, e.g., in a sample, e.g., a tissue sample (a tissue sample as used herein means any suitable sample, e.g., a sample including classic insulin sensitive tissue, e.g., muscle, fat or liver tissue, or a sample including more easily accessible tissue, e.g., circulating blood cells or fibroblasts); the evaluation includes measuring the level of phosphorylation of the IRS-2, e.g., in a tissue sample; the evaluation includes measuring the level of kinase activity of IRS-2; and the evaluation includes measuring the amount of IRS-2 encoding RNA, e.g., in a tissue sample. Although, the method is described here with the IRS-2 gene, other members of the family, (preferably other than IRS-1) can be used.

In another aspect, the invention features a method of determining, preferably prenatally, whether a subject is at risk for an insulin-related disorder, e.g., an insulin resistant insulin-related disorder, e.g., Type II diabetes, or an immune disorder, or a disorder characterized by unwanted cell proliferation. The subject can be a mammal, e.g., a human. The method includes determining the structure of an IRS gene (preferably other than IRS-1), e.g., the IRS-2 gene, an abnormal structure being indicative of risk for the disorder.

In another aspect, the invention features a method of evaluating an effect of a treatment, e.g., a treatment used to treat an insulin-related disorder, or an immune disorder, or a disorder characterized by unwanted cell proliferation. The method uses a test cell or organism which misexpresses an IRS gene (preferably other than IRS-1). In the case where the misexpressed gene is IRS-2 the method includes: administering the treatment to a test cell or organism, e.g., a cultured cell, or a mammal, and evaluating the effect of the treatment on an aspect of IRS-2 metabolism. An effect on an aspect of IRS-2 metabolism indicates an effect of the treatment. In preferred embodiments: the insulin-related disorder is an insulin resistant disease; the effect on an aspect of IRS-2 metabolism is a change in the level of IRS-2 phosphorylation, a change in the level of IRS-2 binding activity, a change in IRS-2 mRNA levels, a change in IRS-2 protein levels. In yet other preferred embodiment, the test cell or organism misexpresses an insulin responsive gene, e.g., IRS-1, IRS-2, or both. Although, the method is described here with the IRS-2 gene, other members of the family, (preferably other than IRS-1) can be used. Some disorders are characterized by inadequate expression of the subject gene, and the ability of a treatment to increase expression is indicative of the treatments usefulness.

In another aspect, the invention features a method of evaluating an effect of a treatment, e.g., a treatment used to treat an insulin-related disorder, or an immune disorder, or a disorder characterized by unwanted cell proliferation. The method includes: providing a test cell or organism, e.g., a cultured cell, or a mammal, which misexpresses an IRS gene (preferably other than IRS-1), e.g., IRS-2; administering the treatment to the animal or cell, evaluating the effect of the treatment on an aspect of insulin metabolism. An effect on an aspect of insulin metabolism indicates an effect of the treatment. In preferred embodiments: the insulin-related disorder is an insulin resistant disease; the effect on an aspect of insulin metabolism is a change in the level of IRS-2 or IRS-1 phosphorylation, a change in the level of IRS-2 or IRS-1binding activity, a change in IRS-2 or IRS-1 mRNA levels, a change in IRS-2 or IRS-1 protein levels, or change in any response to insulin. In yet other preferred embodiment, the test cell or organism misexpresses a second insulin responsive gene (other than IRS-2), e.g., IRS-1. In preferred embodiments, the misexpression of the IRS gene mimics a disorder, e.g., an insulin related disorder.

In another aspect, the invention features a method for evaluating a compound for the ability to modulate (e.g., to inhibit or promote) the binding of an IRS polypeptide (preferably other than IRS-1), e.g., an IRS-2 polypeptide, with an IRS-2 binding ligand, e.g., a naturally occurring ligand, e.g., the insulin receptor. In the case of an IRS-2 polypeptide the method includes: (i) combining an IRS-2 polypeptide, an IRS-2 binding ligand, e.g., a protein, and a compound; and (ii) detecting the formation of a complex which includes the IRS-2 polypeptide and the IRS-2 binding ligand. Modulation of the formation of the complex in the presence of the compound (e.g., as compared with formation in the absence of the compound) is indicative of a modulation of the interaction between an IRS-2 polypeptide and an IRS-2 binding ligand. Other IRS polypeptides (preferably other than IRS-1) can also be used in this method.

In another aspect, the invention features a two-phase method (e.g., a method having a primary in vitro and a secondary in vivo phase) for evaluating a treatment. The method can be used to evaluate a treatment for the ability of the treatment to modulate, e.g., to inhibit or promote, an aspect of insulin metabolism, e.g., an aspect of IRS metabolism, or to evaluate test compounds for use as therapeutic agents. The method includes: (i) an in vitro phase in which the test compound is contacted with a cell, or a cell free system, which includes a reporter gene functionally linked to an IRS regulatory sequence other than an IRS-1 regulatory sequence, e.g., an IRS-2 regulatory sequence, and detecting the modulation of the expression of the reporter gene and (ii) if the test compound modulates the expression, administering the test compound to an animal, and evaluating the in vivo effects of the compound on an aspect of insulin metabolism, e.g., response to insulin or IRS-2 expression.

In another aspect, the invention features a method of evaluating an effect of a treatment which mimics a first effect of insulin, the first effect mediated by an IRS (preferably other than IRS-1), e.g., IRS-2, without mimicking a second effect of insulin. In the case of IRS-2, the method includes administering the treatment to a test organism, e.g., a cell grown in culture or a mammal, and evaluating the effect of the treatment on an aspect of IRS-2 metabolism, e.g., the level of IRS-2 expression, the kinase activity of IRS-2, the cellular or intra-cellular distribution of IRS-2, or the level of the IRS-2 phosphorylation. An effect on an aspect of IRS-2 metabolism indicates an effect of the treatment. Other IRS polypeptides (preferably other than IRS-1) can also be used in this method.

In another aspect, the invention features a method of evaluating an effect of a treatment, which alters the ability of a tyrosine kinase to phosphorylate a substrate which includes the amino acid sequence of one of the tyrosine phosphorylation sites of FIG. 8, other than a YMXM-containing site (SEQ ID NO:2). The method includes administering the treatment to a test organism, e.g., a cultured cell or a mammal, and measuring the level of phosphorylation of a substrate, which includes the amino acid sequence of one of the tyrosine phosphorylation sites of FIG. 8, other than a YMXM-containing site (SEQ ID NO:2), e.g., a naturally occurring substrate of the tyrosine kinase or a synthetic substrate.

In another aspect, the invention features a method of making an IRS-2 polypeptide having a non-wild type activity, e.g., an antagonist, agonist or super agonist of a naturally occurring IRS-2. The method includes: altering the sequence of an IRS-2 polypeptide, e.g., altering the sequence of a non-common phosphorylation site, and testing the altered polypeptide for the desired activity.

In another aspect, the invention features a method of making an IRS polypeptide, (e.g., an IRS polypeptide, preferably other than IRS-1, e.g., IRS-2) having a non-wild type activity, e.g., an antagonist, agonist, or super agonist of a naturally occurring IRS. The method includes: altering the sequence of one or more of the IRS-CPS's of the polypeptide or altering the sequence of one or more of IH1, IH2, or IH3, and testing the altered polypeptide for the desired activity.

In another aspect, the invention features a method of making a fragment or analog of an IRS-2 polypeptide having a biological activity of a naturally occurring IRS-2. The method includes: altering the sequence of a IRS-2 polypeptide, e.g., altering the sequence of a non-common phosphorylation site, and testing the altered polypeptide for the desired activity.

In another aspect, the invention features a method of making a fragment or analog of an IRS polypeptide, (e.g., an IRS polypeptide, preferably other than IRS-1, e.g., IRS-2) having a biological activity of a naturally occurring IRS. The method includes: altering the sequence of one or more of the IRS-CPS's of an IRS polypeptide or altering the sequence of one or more of IH1, IH2, or IH3, and testing the altered polypeptide for the desired activity.

In another aspect, the invention features, a method of evaluating a compound for the ability to bind an IRS polypeptide (preferably other than IRS-1), e.g., an IRS-2 polypeptide. The method includes: contacting the compound with the polypeptide; and evaluating ability of the compound to form a complex with the polypeptide.

In another aspect, the invention features, a method of evaluating a compound for the ability to bind a nucleic acid encoding an IRS regulatory sequence (preferably other than IRS-1), e.g., an IRS-2 regulatory sequence. The method includes: contacting the compound with the nucleic acid; and evaluating ability of the compound to form a complex with the nucleic acid.

In another aspect, the invention features a method of treating a mammal, e.g., a human, at risk for a disorder, e.g., an immune system disorder, a disorder characterized by unwanted cell proliferation, or an insulin related disorder, e.g., a disorder characterized by an abnormality of IRS metabolism, e.g., IRS-2 or IRS-1 metabolism. The method includes administering to the mammal a treatment, e.g., a therapeutically effective amount an IRS polypeptide (preferably other than IRS-1), e.g., an IRS-2 polypeptide, which alters an aspect of insulin metabolism. In preferred embodiments the disorder is characterized by the inability of the insulin receptor to respond to insulin by phosphorylating IRS-2 or IRS-1. In other preferred embodiments the treatment increases the phosphorylation of IRS-2, e.g., by increasing the activity of a kinase or decreasing the activity of a phosphatase. In other preferred embodiments the treatment decreases the phosphorylation of IRS-2, e.g., by decreasing the activity of a kinase or increasing the activity of a phosphatase.

In another aspect, the invention features a method of treating a mammal, e.g., a human, at risk for a disorder, e.g., a disorder caused by a tyrosine kinase. The method includes administering to the mammal a treatment, e.g., a therapeutically effective amount of an IRS-2 polypeptide, which modifies the ability of endogenous IRS-2 to alter the phosphorylation of the tyrosine kinase, thereby altering the activity of the tyrosine kinase. In preferred embodiments the tyrosine kinase is the product of an oncogene.

In another aspect, the invention features a method of treating a mammal, e.g., a human, at risk for a disorder, e.g., a disorder characterized by abnormal cell proliferation. Abnormal cell proliferation, as used herein, includes both neoplastic and non-neoplastic disorders, and thus includes diseases such as cancer and artherosclerosis. The method includes administering to the mammal a treatment, e.g., a therapeutically effective amount of an IRS polypeptide other than an IRS-1 polypeptide, e.g., an IRS-2 polypeptide, which alters an aspect of insulin metabolism, e.g., an aspect of IRS-2 metabolism. In preferred embodiments the aspect of insulin metabolism is IRS-2 phosphorylation. In other preferred embodiments the aspect of insulin metabolism is the level of kinase activity of IRS-2.

In another aspect, the invention features a method of treating a mammal e.g., a human, at risk for a disorder, e.g., a disorder characterized by the phosphorylation of a substrate of a tyrosine kinase, the substrate including the amino acid sequence of one of the tyrosine phosphorylation sites of FIG. 8, other than a YMXM-containing site (SEQ ID NO:2). The tyrosine kinase may be, e.g., a receptor tyrosine kinase, e.g., insulin receptor, epidermal growth factor (EGF) receptor, platelet derived growth factor, (PDGF) receptor, or insulin-like growth factor (ILG) receptor, or an oncogene product, e.g., the src, abl, or fms gene product. The method includes administering a treatment, e.g., a therapeutically effective amount of a therapeutic agent, e.g., an IRS-2 polypeptide, which includes the amino acid sequence of one of the tyrosine phosphorylation sites of FIG. 8, other than a YMXM-containing site (SEQ ID NO:2). In preferred embodiments the therapeutic agent blocks phosphorylation of the naturally occurring substrate by competitive or non-competitive inhibition of the naturally occurring substrate.

An immune system disorder is a disorder characterized by either, an unwanted immune response, or by the absence or reduction of a normal immune response.

An insulin-related disorder, as used herein, is a disease, or condition in which an aspect of insulin metabolism is disrupted, or, a disorder in which insulin action contributes to the disorder. An insulin resistant insulin-related disorder, as used herein, is any disease, or condition in which a normal amount of insulin results in a less than normal biological response. Examples of insulin resistant disorders include Type II diabetes, obesity, aging related insulin resistance, and insulin resistance that arises secondary to infections, hormonal disorders, or other causes.

A vector, as used herein, is an autonomously replicating nucleic acid molecule.

A heterologous promoter, as used herein is a promoter which is not naturally associated with a gene or a purified nucleic acid.

A purified preparation or a substantially pure preparation of an IRS polypeptide (other than IRS-1), as used herein, means an IRS polypeptide that has been separated from other proteins, lipids, and nucleic acids with which it naturally occurs. Preferably, the IRS polypeptide is also separated from substances, e.g., antibodies or gel matrix, e.g., polyacrylamide, which are used to purify it. Preferably, the IRS polypeptide constitutes at least 10% dry weight of the purified preparation. Preferably, the preparation contains: sufficient IRS polypeptide to allow protein sequencing; at least 1, 10, or 100 μg of IRS polypeptide; at least 1, 10, or 100 mg of IRS polypeptide.

A purified preparation or a substantially pure preparation of IRS-2, as used herein, means IRS-2 that has been separated from other proteins, lipids, and nucleic acids with which it naturally occurs. Preferably, the IRS-2 is also separated from substances, e.g., antibodies or gel matrix, e.g., polyacrylamide, which are used to purify it. Preferably, the IRS-2 constitutes at least 10% dry weight of the purified preparation. Preferably, the preparation contains: sufficient IRS-2 to allow protein sequencing; at least 1, 10, or 100 μg of IRS-2 polypeptide; at least 1, 10, or 100 mg of IRS-2 polypeptide.

SH2 domain, as used herein, refers to a conserved apparently noncatalytic sequence of approximately 100 amino acids found in many signal transduction proteins including Fps, Stc, Abl, GAP, PLCλ, v-Crk, Nck, p85, and Vav. See Koch et al., 1991, Science 252:668, hereby incorporated by reference. The amino acid sequences of the SH2 domain of 27 proteins is given in Koch et al., 1991. The SH2 domain mediates protein-protein interactions between the SH2 containing protein and other proteins by recognition of a specific site on a second protein. The SH2/second protein site interaction usually results in an association of the SH2 contacting protein and the second protein. As used herein, SH2 domain refers to any sequence with at least 70%, preferably at least 80%, and more preferably at least 90% sequence homology with a naturally occurring SH2 domain, and to any analog or fragment of an SH2 domain which exhibits at least 50% of the binding activity of a naturally occurring variant of that domain, when binding is measured as the ability to bind a YFIN (SEQ ID NO:3) containing peptide.

A purified preparation of cells refers to, in the case of plant or animal cells, an in vitro preparation of cells and not an entire intact plant or animal. In the case of cultured cells or microbial cells, it consists of a preparation of at least 10% and more preferably 50% of the subject cells.

Abnormal cell proliferation, as used herein, includes both neoplastic and non-neoplastic diseases, and thus includes diseases such as cancer and artherosclerosis.

A mutation, as used herein, means an alteration, either gross or fine structure, in a nucleic acid. Examples of common mutations are nucleotide deletions and insertions. The mutation further can be a mutation of the DNA encoding IRS-2 which results in misexpression of IRS-2.

A treatment, as used herein, includes any therapeutic treatment, e.g., the administration of a therapeutic agent or substance, e.g., a drug.

The metabolism of a substance, as used herein, means any aspect of the, expression, function, action, or regulation of the substance. The metabolism of a substance includes modifications, e.g., covalent or non covalent modifications of the substance. The metabolism of a substance includes modifications, e.g., covalent or non covalent modification, the substance induces in other substances. The metabolism of a substance also includes changes in the distribution of the substance. The metabolism of a substance includes changes the substance induces in the distribution of other substances.

A substantially pure nucleic acid, e.g., a substantially pure DNA, is a nucleic acid which is one or both of: not immediately contiguous with both of the coding sequences with which it is immediately contiguous (i.e., one at the 5' end and one at the 3' end) in the naturally-occurring genome of the organism from which the nucleic acid is derived; or which is substantially free of a nucleic acid sequence with which it occurs in the organism from which the nucleic acid is derived. The term includes, for example, a recombinant DNA which is incorporated into a vector, e.g., into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment) independent of other DNA sequences. Substantially pure DNA also includes a recombinant DNA which is part of a hybrid gene encoding additional IRS-2 sequence.

Homologous refers to the sequence similarity between two IRS-2 molecules or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared× 100. For example, if 6 of 10, of the positions in two sequences are matched or homologous then the two sequences are 60% homologous. By way of example, the DNA sequences ATTGCC and TATGGC share 50% homology. Generally, a comparison is made when two sequences are aligned to give maximum homology.

The terms peptides, proteins, and polypeptides are used interchangeably herein.

As used herein, the term "transgene" means a nucleic acid sequence (encoding, e.g., one or more hematopoietic peptides), which is partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene can include one or more transcriptional regulatory sequences and any other nucleic acid, such as introns, that may be necessary for optimal expression of the selected nucleic acid, all operably linked to the selected nucleic acid, and may include an enhancer sequence.

As used herein, the term "transgenic cell" refers to a cell containing a transgene.

As used herein, a "transgenic animal" is any animal in which one or more, and preferably essentially all, of the cells of the animal includes a transgene. The transgene can be introduced into the cell, directly or indirectly by introduction into a precursor of the cell, by way of deliberate genetic manipulation, such as by microinjection or by infection with a recombinant virus. This molecule may be integrated within a chromosome, or it may be extrachromosomally replicating DNA.

A polypeptide has IRS-2 biological activity if it has one, two, three, and preferably more of the following properties: (1.) the peptide is capable of binding to insulin receptor; (2.) the peptide is capable of binding to IL-4 receptor complex; (3.) the peptide is capable of binding to IL-15 receptor complex; (4.) the peptide is capable of binding specific IRS antibodies; (5.) the peptide is capable of association with SH2 domains of Grb-2, SH-PTP-2, nck, and c-fyn, after ligand stimulation; (6.) the peptide is capable of association with PI 3'-kinase, preferably to the SH2 region of PI 3'-kinase, after ligand stimulation, and is capable of stimulating PI 3'-kinase activity; (7.) the peptide is capable of being phosphorylated by the insulin receptor or other tyrosine kinases. A polypeptide has biological activity if it is an antagonist, agonist, or super-agonist of a polypeptide having one of the above-listed seven properties.

Misexpression, as used herein, refers to a non-wild type pattern of gene expression. It includes: expression at non-wild type levels, i.e., over or under expression; a pattern of expression that differs from wild type in terms of the time or stage at which the gene is expressed, e.g., increased or decreased expression (as compared with wild type) at a predetermined developmental period or stage; a pattern of expression that differs from wild type in terms of decreased expression (as compared with wild type) in a predetermined cell type or tissue type; a pattern of expression that differs from wild type in terms of the size, amino acid sequence, posttransitional modification, or biological activity of IRS-2; a pattern of expression that differs from wild type in terms of the effect of an environmental stimulus or extracellular stimulus on expression of the gene, e.g., a pattern of increased or decreased expression (as compared with wild type) in the presence of an increase or decrease in the strength of the stimulus.

IH1, as used herein, refers to the IRS-homology domain I (also called the pleckstrin homology domain (PH)). The IH1 is usually in the N-terminal region of native IRS polypeptide. An exemplary IH1, the IRS-2 IH1, is found at residues 30–141 of IRS-2 (SEQ ID NO:1). In general, IH 1 sequences will be approximately 90–120, and more preferably about 112 amino acids in length. Another exemplary IH1, is the IH1 of IRS-1 (residues 13–113 of IRS-1). In general, IH1 sequences will have at least 60%, 70%, 80%, 85%, 90%, 95%, or 99% homology with residues 30–141 of SEQ ID NO:1 or with the IH1 of IRS-1.

IH2, as used herein, refers to the IRS-homology domain 2. The IH2 is usually in the N-terminal region of native IRS polypeptide. An exemplary IH2, the IRS-2 IH2, is found at residues 190–366 of SEQ ID NO:1. In general, IH2 sequences will be approximately 150–200, and more preferably about 175 amino acids in length. Another exemplary IH2 is the IH2 of IRS-1, found at residues 155–328 of IRS-1. In general, IH2 sequences will have at least 70%, 80%, 85%, 90%, 95%, or 99% homology with residues 190–366 of IRS-2 of SEQ ID NO:1 or with residues 155–328 of IRS-1.

IH3, as used herein, refers to the IRS-homology domain 3. The IH3 is usually in the N-terminal region of native IRS polypeptide. An exemplary IH3, the IRS-2 IH3, is found at residues 481–527 of SEQ ID NO:1. In general, IH3 sequences will be approximately 25–75, and more preferably about 50 amino acids in length. Another exemplary IH3 is the IH3 of IRS-1, found at residues 408–452 of IRS-1. In general, IH3 sequences will have at least 70%, 80%, 85%, 90%, 95%, or 99% homology with residues 481–527 of SEQ ID NO:1 or residues 408–452 of IRS-1.

IRS proteins contain a constellation of IRS-common-tyrosine-containing phosphorylation sites (IRS-CPS). IRS-1 and IRS-2 share the IRS CPS's detailed in Table 1 below. Note, for CPS sequences see FIG. 8.

TABLE 1

| SITE | Y LOCATION IN IRS-1 | Y LOCATION IN IRS-2 |
|---|---|---|
| CPS1 | 46,47 | 80,81 |
| CPS2 | 107 | 141 |
| CPS3 | 426 | 504 |
| CPS4 | 460 | 543 |
| CPS5 | 546 | 599 |
| CPS6 | 578 | 629 |
| CPS7 | 608 | 654 |
| CPS8 | 628 | 676 |
| CPS9 | 727 | 763 |
| CPS10 | 895 | 916 |
| CPS11 | 939 | 974 |
| CPS12 | 1172 | 1247 |
| CPS13 | 1222 | 1309 |

The method of the invention can be used to diagnose the presence of a disorder characterized by an abnormality in the structure or metabolism of an IRS gene (other than IRS-1), e.g., IRS-2. The disorder can be e.g., an immune disorder, an insulin-related disorder, or a disorder characterized by unwanted cell proliferation.

The invention allows for the analysis of various aspects of metabolism, e.g., insulin metabolism, e.g., for the determination of insulin receptor function, e.g., the detection of insulin-stimulated substrate phosphorylation.

The invention also provides useful tools for the testing and development of agents used to treat or diagnose the above-listed disorders.

Methods of the invention also allow the treatment of a variety of disorders, e.g., insulin related diseases, insulin resistant diseases, diseases characterized by abnormal cellular proliferation, immune disorders or disorders associated with the phosphorylation of a substrate by a tyrosine kinase.

Other features and advantages of the invention will be apparent from the following description of the preferred embodiments and from the claims.

DETAILED DESCRIPTION OF THE INVENTION

The drawings are first briefly described.

Drawings:

FIG. 4 is alignment of IRS-1 and IRS-2 DNA sequences. Boxed sequences indicate regions of 100% identity.

FIG. 6 is a map of the translated sequence of IRS-2 (SEQ ID NO:1 is the nucleic acid, and SEQ ID NO:64 is the amino acid).

FIG. 7 is an alignment of IRS-1 and IRS-2 amino acid sequences. Boxed sequences indicate regions of 100% identity.

Evidence that IRS-2 is distinct from IRS-1

Figure 1:
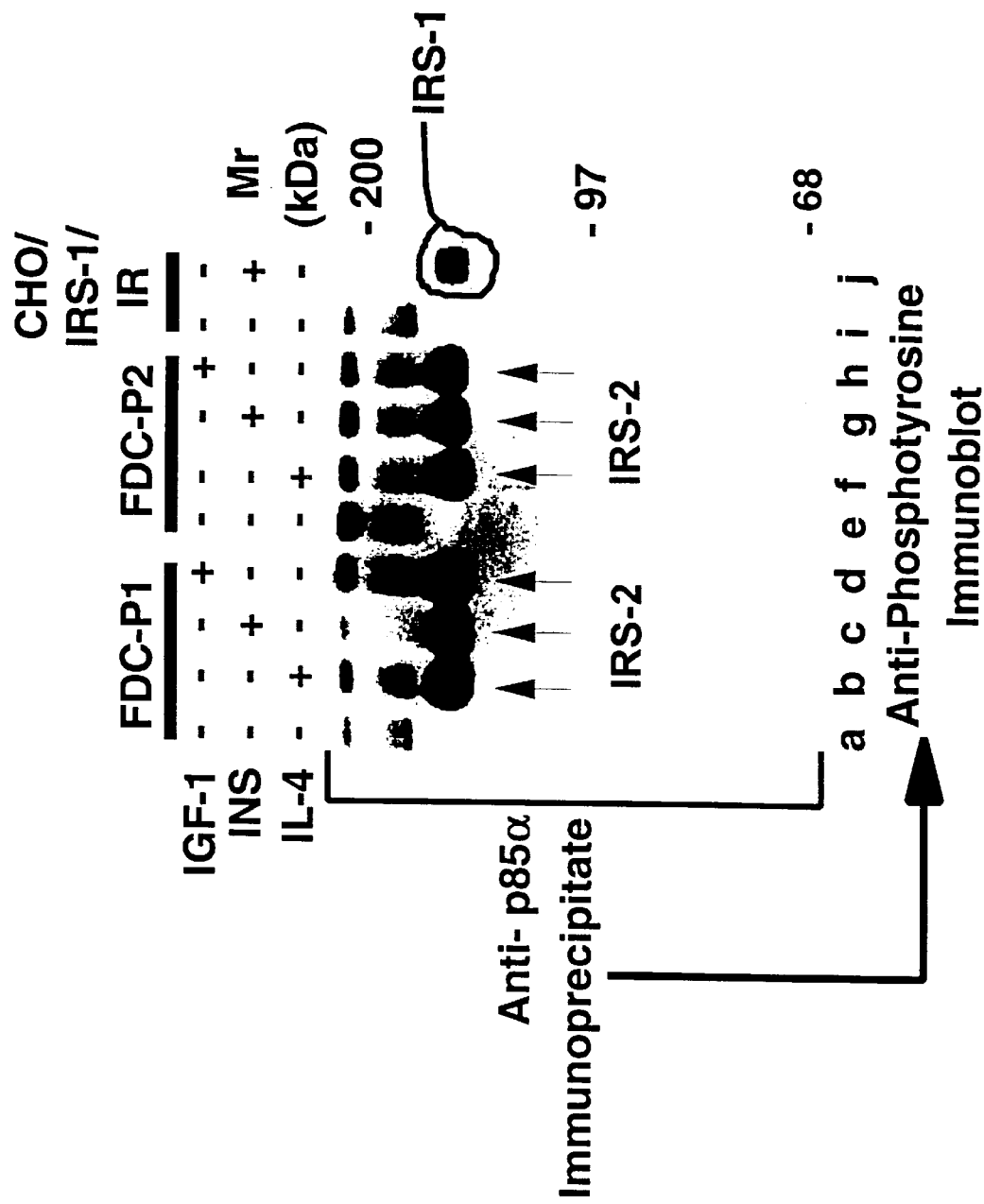
FIG. 1 is a gel of the co-immunoprecipitation of IRS-2 and IRS-1 with anti-PI 3'-kinase antibody (anti-p85).

Like IRS-1, IRS-2 strongly associates with the PI 3'-kinase after ligand stimulation. This is shown in immunoprecipitates of the regulatory subunit of the PI 3'-kinase (p85α) from myeloid progenitor (FDC) cells stimulated with insulin, IL-4 or IGF-1. p85α immunoprecipitates contained IRS-2 which was detected with αPY (FIG. 1). Moreover, IRS-2 co-migrates during SDS-PAGE with IRS-1 obtained by similar methods from CHO cells (FIG. 1, lane j).

IRS-2 does not react with most IRS-1 antibodies, further supporting its unique character. Antibodies raised against the amino terminus (αNT), carboxy-terminus (α CT), or a middle region (αPep80) of IRS-1 do not immunoprecipitate IRS-2 from insulin-stimulated FDC-P2 cells. Moreover, one polyclonal antibody (αIRS-1-#1) obtained from rabbits injected with recombinant IRS-1 did not react with IRS-2, whereas a different one (αIRA-1-#2) reacts with IRS-2. These results provide immunological evidence that IRS-2 is a distinct protein that is partially related to IRS-1.

An antibody to the first 130 amino acids in IRS-1, which constitute the so-called pleckstrin homology (PH) domain was prepared (PH-domains maybe important for protein-protein interactions). The PH-domain antibody reacts with IRS-2 and IRS-1, suggesting that this region may be conserved in the two proteins.

That IRS-1 is modified in myeloid cells, so that it cannot react with all IRS-1 antibodies, was shown not to be the case since IRS-1 expressed in FDC-P1 cells readily reacts with αIRS-1. A sensitive way to demonstrate this is to carry out PI 3'-kinase assays on αIRS-1 immunoprecipitates. Whereas anti-phosphotyrosine (αPY) immunoprecipitates PI 3'-kinase activity from FDC-P1 cells after IL-4 stimulation, the αIRS-1-#1 antibody does not. However, after expression of IRS-1 in FDC-P1 cells, the amount of PI 3'-kinase immunoprecipitated with αPY increased and PI 3'-kinase was also found in αIRA-1-#1 immunoprecipitates. Therefore, αIRS-1 in myeloid cells can react with αIRS-1, whereas IRS-2 does not. This is evidence that IRS-2 is a distinct substrate.

The IRS-1 gene is absent in IRS-2-containing FDC-P2 cells

Since IRS-1 is absent from FDC-P2 cells, it seemed possible to purify IRS-2 from this source. In order to determine the feasibility of cloning IRS-2 from murine FDC-P2 cells, a directional cDNA expression library was prepared in a λEXlox vector with mRNA isolated from FDC-P2 cells. This λEXlox cDNA library was analyzed by PCR analysis and low stringency screening with an IRS-1 cDNA probe. Fourteen PCR primer pairs were chosen to produce 300 to 600 bp products throughout the entire coding region of mouse IRS-1. Each of the primer pairs yielded a product of the expected size from a library known to contain IRS-1; however, none of the PCR products obtained from the library matched the expected results for IRS-1. This result suggests that IRS-1 cDNA is either unrepresented in the library or at such a low concentration that it is undetectable by our methods. Moreover, the 180-kDa phosphotyrosine protein (IRS-2) must be distinct from IRS-1.

Next, the FDC-P2 library was screened at low and high stringency with a full-length IRS-1 cDNA probe lacking the polyglutamine region $(CAG)_{30}$. No positive clones were identified at high stringency as ordinarily observed in hepatocyte, fat or muscle cDNA libraries that contain IRS-1. Thus, IRS-1 gene was not found in FDC-P2 libraries.

Two hundred weakly positive clones were obtained by low stringency screening of the λEXlox with the full-length IRS-1 probe lacking the polyglutamine region $(CAG)_{30}$. The eight strongest positive clones were isolated and sequenced. These clones were identified as mouse acidic ribosomal phosphoprotein (mARP). mARP is 36 kDa protein encoded by 1094 bases that contain numerous stretches of identity to IRS-1 at the cDNA level. The overall identity is about 46%. However, no similarity occurs at the amino acid sequence level because the reading frames are different. PCR analysis of these clones reveals that the PCR products from the library likely results from this cDNA. Since it is difficult to devise a way to logically screen the additional 192 clones obtained from the low stringency IRS-1 screen, the approach was abandoned. Moreover, PCR cloning failed to reveal the IRS-2 gene. It was provisionally concluded that FDC-P2 cells do not contain IRS-1, and IRS-2 cannot be obtained by straightforward techniques.

Purification of IRS-2

The strategy to purify the IRS-2 relied in part on the fact that IRS-2 associates with PI 3'-kinase after insulin or IL-4 stimulation. The data in the previous section suggest this association occurs through the same mechanism used by IRS-1. In this model, tyrosine phosphorylation sites in IRS-2 might be expected to bind to the Src homology-2 (SH2) domains in p85. Therefore, immobilized SH2 domains of p85 were used as affinity reagents to purify IRS-2 from insulin stimulated FDC-P2 cells.

The efficiency of the SH2 affinity column was compared with that of an affinity column made with antiphosphotyrosine antibody. The efficiency of IRS-2 binding to antiphosphotyrosine antibody αPY, or glutathione-S transferase (GST) bacterial fusion proteins containing the SH2-domains of p85 (GST-SH2$^{p85}$), Fyn (GST-SH2$^{fyn}$), GRB2 (GST-SH2$^{GRB2}$), SH-PTP2 (GST-SH2$^{syp}$) was tested. FDCP-2 cells were grown to 0.7·10⁶ cell/ml. Before the experiment, the cells (3.5·10⁶/ml) were incubated in DMEM containing high glucose, and 50 μPM V0₄ for 2 hours. Cell lysates, prepared from an equal amount of insulin-stimulated or unstimulated cells, were incubated with αPY or the various GST fusion proteins containing different SH2 domains. αPY immunocomplexes were precipitated with protein A Sepharose, and washed three times with lysate buffer. The GST fusion protein complexes were precipitated with glutathion-Sepharose, and the resin was briefly washed twice with GST binding buffer. Bound protein was removed from the protein A Sepharose resin by boiling in Laemmli sample buffer containing 0.1M DTT for 5 min. The eluted protein mixture was resolved into components on a 7.5% SDS page gel, and transferred to nitrocellulose membrane. IRS-2 was detected by αPY immunoblotting. GSTnSH2P⁸⁵ (a GST-SH2P⁸⁵ containing the amino terminal SH2 of p85) precipitated equivalent amounts of IRS-2 compared to αPY (3 μg). Increasing the amount of fusion protein from 5 μg to 20 μg precipitated almost all the IRS-2 in the lysate since there was no detectable IRS-2 in a second round of precipitation.

GSTnSH2$^{P85}$ was chosen for the purification of IRS-2 instead of αPY for a number of reasons including:

1. Pure fusion protein can be prepared in a large quantity in a short period of time.
2. It is easy to pack a high capacity affinity column.
3. GSTnSH2$^{P85}$ binding protein can be specifically eluted with 20 mM glutathion.

To evaluate this choice, FDCP-2 cells were stimulated with insulin, and extracts were passed over a small SH2$^{P85}$ affinity column. Several fractions of eluate were collected and separated by SDS-PAGE. IRS-2 was readily detected by protein staining in fractions 2–4.

A high capacity affinity column was made by running 4 mg of GSTnSH2$^{P85}$ through a column containing 0.4 ml glutathion sepharose, and washing extensively with washing buffer (10 mM DTT in PBS containing 200 μg/ml BSA). An FDC-P2 cell lysate was prepared from 30 liters of insulin stimulate FDCP-2 cells and applied on the GSTnSH2$^{P85}$ affinity column. The column was washed with 10 ml of washing buffer and 10 ml of washing buffer without BSA. The proteins were eluted with 2×1 ml of elution buffer (20 mM glutathion, 20 mM DTT, 250 mM NaCl in 50 mM Tris, pH 7.4), and concentrated in a Centricon-30. The proteins were boiled in Laemmli sample buffer containing DTT (0.1M final concentration) for 5 min, separated by 7.5% SDS-PAGE, transferred to PVDF membrane, and stained with Ponceau S. A doublet band appeared on the membrane at the same position as recombinant IRS-1 used as a control. The approximate amount of purified IRS-2 based on the quantitation of IRS-1 and density of Ponceau S staining was about 5 μg.

Figure 2:
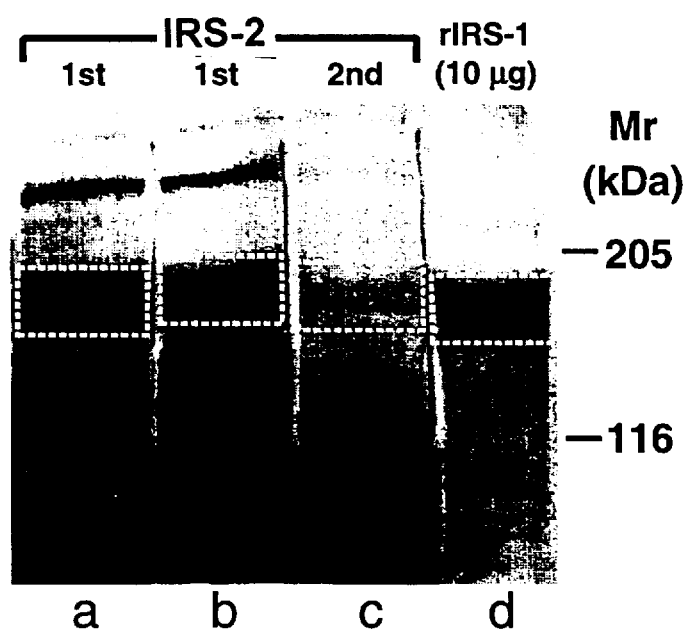
FIG. 2 is a gel showing a product of a large-scale purification of IRS-2.

The protein bands of interest are boxed (FIG. 2). The bands that contained IRS-2 and IRS-1 were excised and subjected to protease Lys-C digestion separately. The resulting peptides were separated on HPLC, and the elution profiles at OD$_{214}$ determinants. The peptide maps for IRS-2 and IRS-1 were strikingly different, suggesting that IRS-2 is a different molecule from IRS-1.

Eight major novel peptides were subjected to amino acid sequencing. The amino acid sequence of each is shown in Table 2. Seven of the peptides had no homology with any peptide sequences in the protein data bank. One of the peptides (p90) shared 80% homology with sequence in IRS-1. These data indicated that IRS-2 is a novel protein and strongly indicated that IRS-2 is related to IRS-1.

TABLE 2

| Peptide | Sequence | Identity |
|---|---|---|
| p60 | VAYNPYPEDYGDIEIgshk (SEQ ID NO:4) | IRS-2 |
| p96 | LS-eGLQTLPSMS-YpL-n (SEQ ID NO:5) | IRS-2 |
| p128 | YGFSDPLTFNsVVELIN-Yr (SEQ ID NO:6) | p85nSH2 |
| p109 | LLLEYLEEKYEEHLYER (SEQ ID NO:7) | GST |
| p79 | gFQqISFVNS-ATsK (SEQ ID NO:8) | ? |
| p93 | ELDMNNaM-1Q-AE-a (SEQ ID NO:9) | ? |
| p90 | ETSVGFQNGLNYIAIDV (SEQ ID NO:10) | IRS-2 |
| p80 | LPPASAATSQGP-a (SEQ ID NO:11) | IRS-2 |
| p47 | ALTDLVSEGR (SEQ ID NO:12) | IRS-2 |

Cloning of IRS-2

A mouse FDCP-2 cell cDNA library prepared in λEXlox™, and a mouse genomic library in λFIX vector (Strategene) were screened with an oligonucleotide probe. The probe (PROBE-60) was prepared with a pair of oligonucleotides with a 10 nucleotide overlap based on the amino acid sequence of p60 Table 2:

1. GTGGCCTACAACCCATACCCTGAGGAC (SEQ ID NO:13)
2. AATCTCAATGTCGCCATAGTCCTCAGGG (SEQ ID NO:14)

Each pair of oligonucleotides (0.6 pmol) was annealed in 10 μl of labeling buffer (Amersham). [³²P]dATP (210 μl of 1 mCi/ml, 3000 Ci/mmol) and [³²P]dCTP (21 μl of 20 mCi/ml, 6000 Ci/mmol) were mixed and lyophilized in microfuge tubes, followed by addition of 26 μl of H₂O, 4 μl of 5× labeling buffer, 4 μl of dGTP and dTTP, 10 μl of annealed oligos, and extended with excess Klenow (Amersham). The mixture was incubated at room temperature for 2 hours and then at 37° C. for 30 min.

The labeled probe was separated from free dNTPs using an Elutip (Schleicher and Schuell). Specific activity was 8×10⁸ cpm/pmol for probe-60. Approximately 1.0 million plaques were plated at a density of 40,000 plaques per 150 mm plate, transferred to nitrocellulose filters (Schleicher and Schuell), and screened with a probe-60 (2.5×10⁶ cpm/ml). Hybridizations were performed overnight in 5× Denhardt's solution containing 20% formamide, 10% dextran sulfide, 6×SSC, and 50 mM sodium phosphate (pH 6.8) containing 100 μg/ml salmon sperm DNA. The filters were washed 3 times with 2× SSC containing 0.1% SDS at 22° C., then for 30 min with 0.2× SSC and 0.1% SDS at 37° C. for 30 min. The dried blots were exposed to Kodak XAR-5 film with a Quanta 111 intensifying screen at −70° C.

Figure 3:
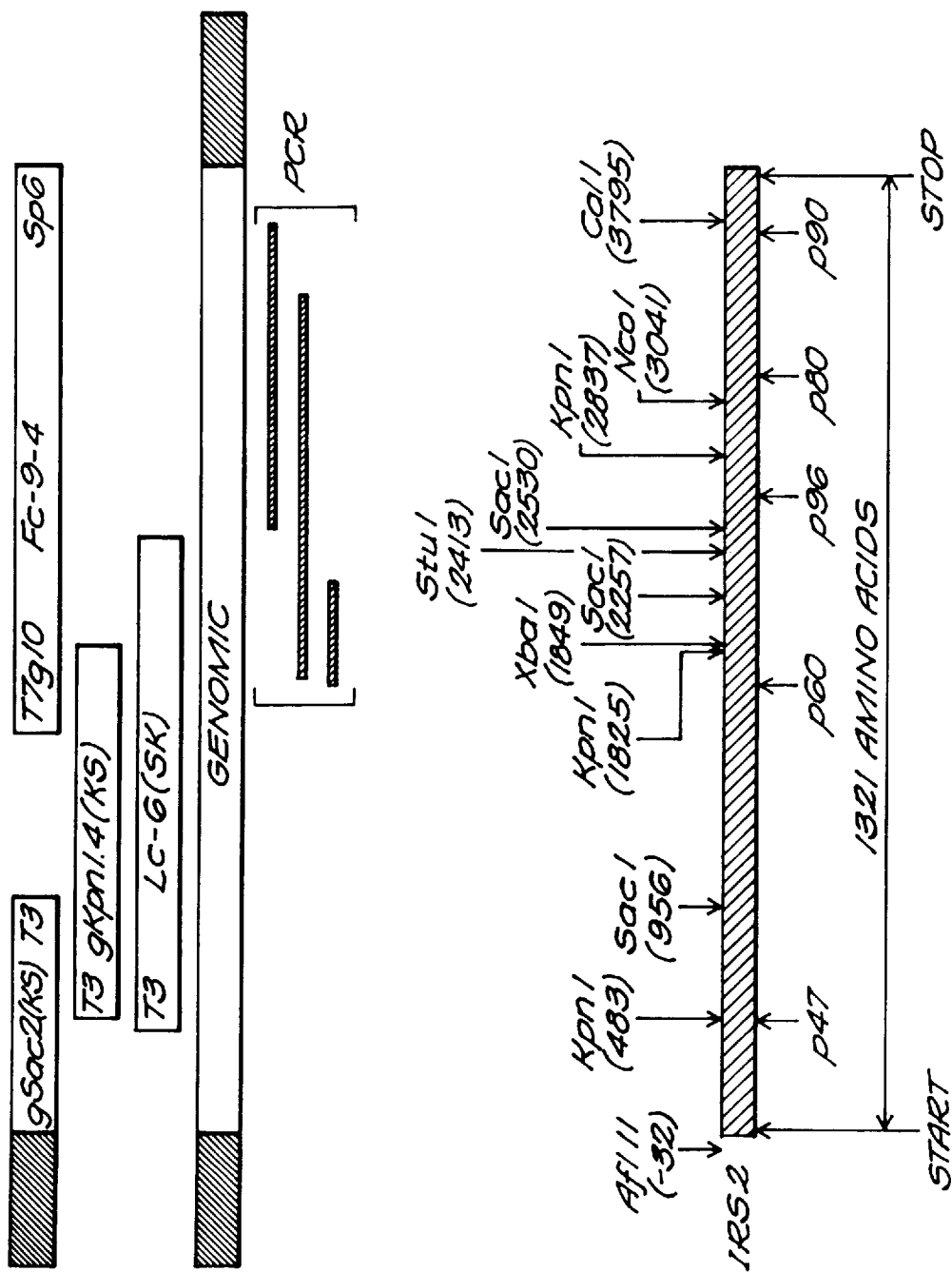
FIG. 3 is a map of clones and restriction sites from the cloning of IRS-2.

One cDNA (c9-4) and one genomic DNA (g9) were identified in 1.0 million clones of each library. Clone c9-4 contains a 2.4 kpb insert including a poly-A region indicating the 3'-end of the cDNA (FIG. 3). The nucleotide sequence of c9-4 contains a relatively low level, but recognizable homology with mouse IRS-1 sequence (30–40%); however, the translated peptide sequences revealed the presence of several tyrosine phosphorylation sites in amino acid sequence motif similar to those in IRS-1. These results confirm that IRS-2 is related to IRS-1.

This initial cDNA fragment was used to screen a mouse lung cDNA library. One new cDNA clone was obtained called Lc-6(SK) (FIG. 3). This clone overlapped with the initial clone and extended the sequence in the 5'-direction. That the IRS-1coding region lacks an intron in the coding region, suggested that the IRS-2 genomic sequence would lack an intron and could be used to isolate the full length coding region. A Sac I fragment from the 5'-end of the c9-4 clone was used to probe genomic DNA restriction fragments by Southern blot. A 1.4 kbp Kpn I fragment hybridized with the probe and was predicted to contain 5'-end sequence. The 1.4 kbp fragment was subcloned into pBluescript and sequenced. The genomic DNA fragments were reprobed with the 1.4 kbp (gKpn1.4) revealing a 2 kbp Sac I fragment which provisionally assigns additional 5'-end DNA sequence. Both genomic DNA fragments were sequenced, reading frame was followed by peptide sequences obtained from IRS-2 and homology with IRS-1 (FIG. 3). An alignment is shown in FIG. 3. It is possible that errors exist in the first 450 nucleotides because a corresponding cDNA has not been isolated. However, subsequent alignments suggest that the correct sequence has been assembled.

Figure 4:
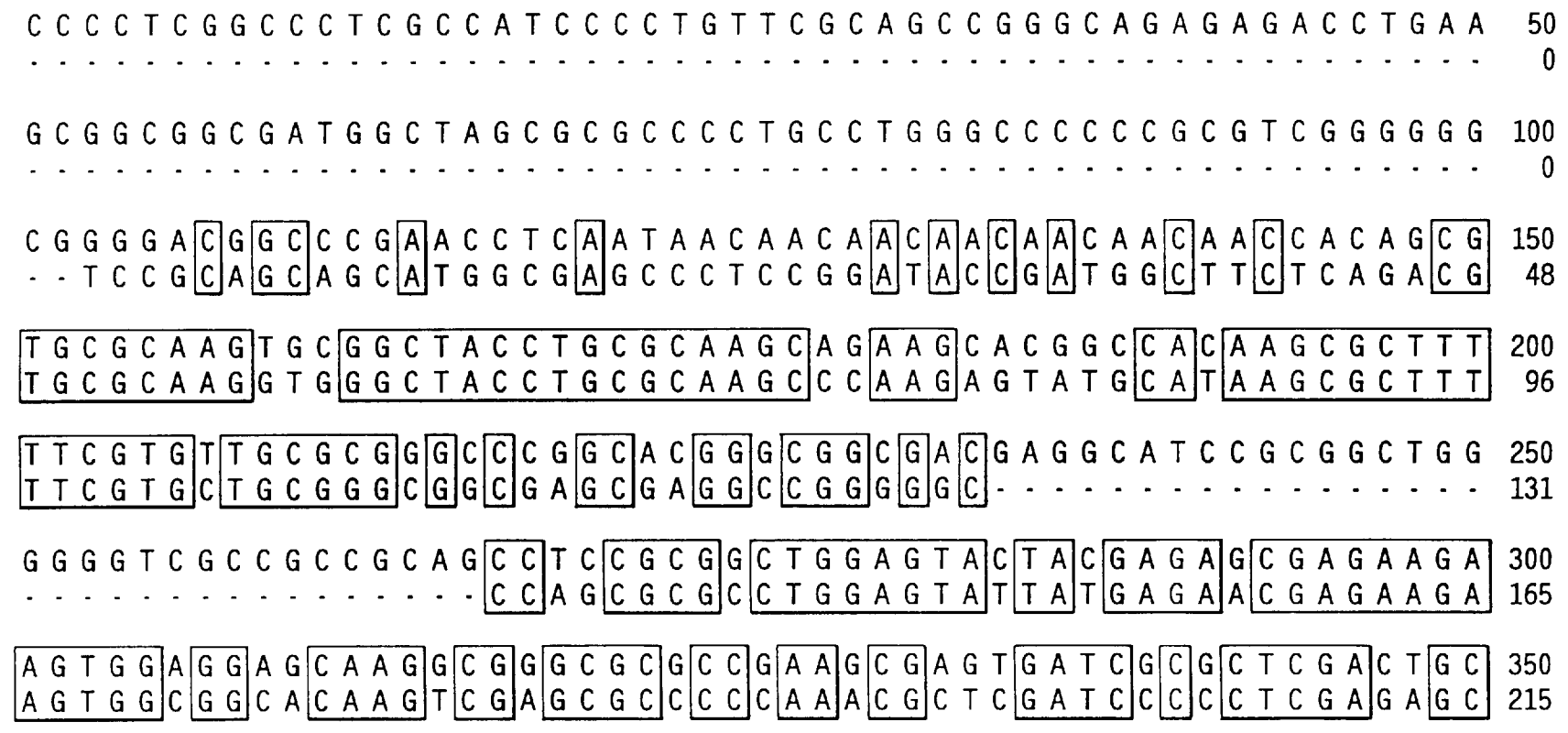
Figure 4:
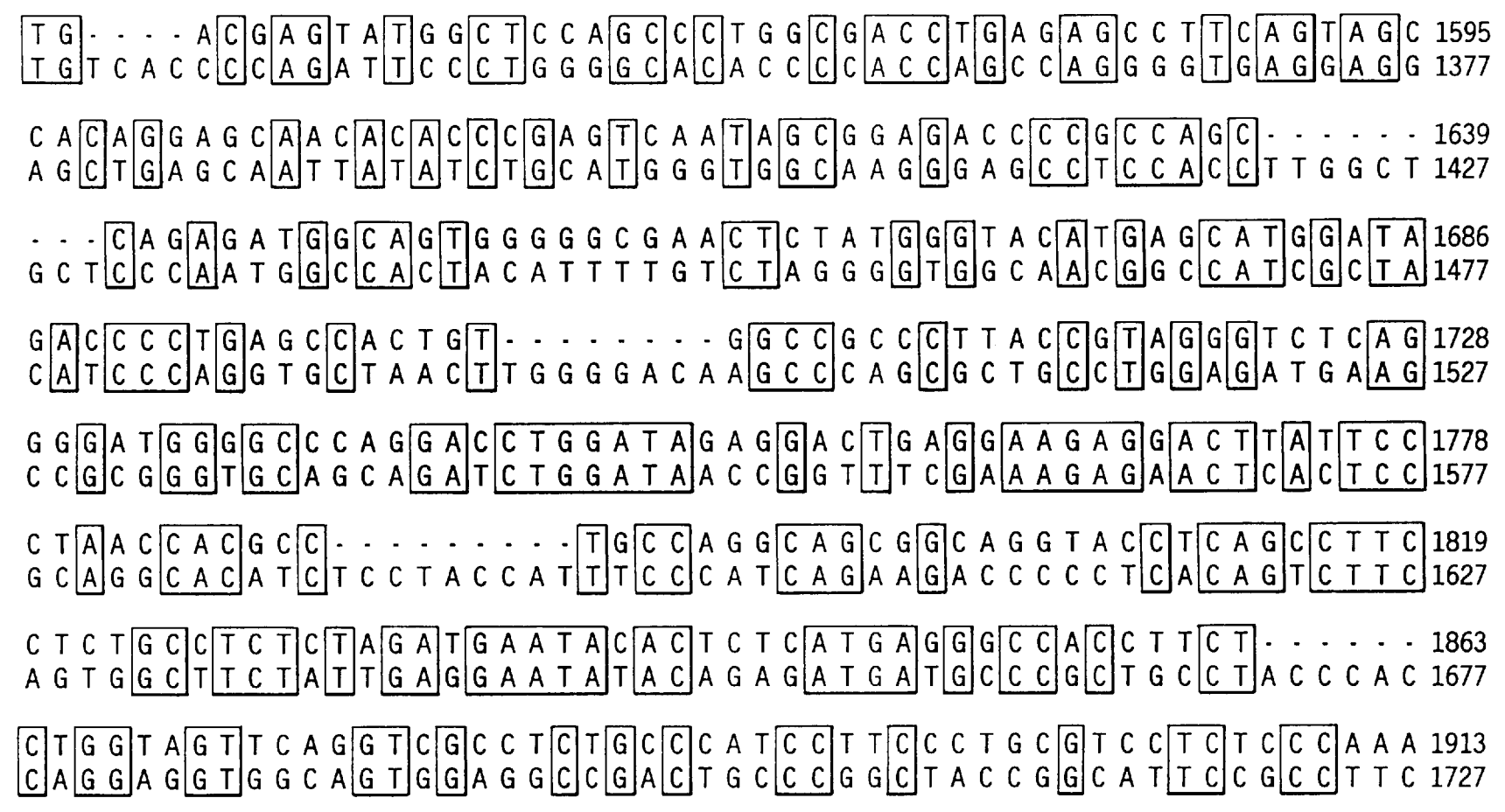
Figure 4:
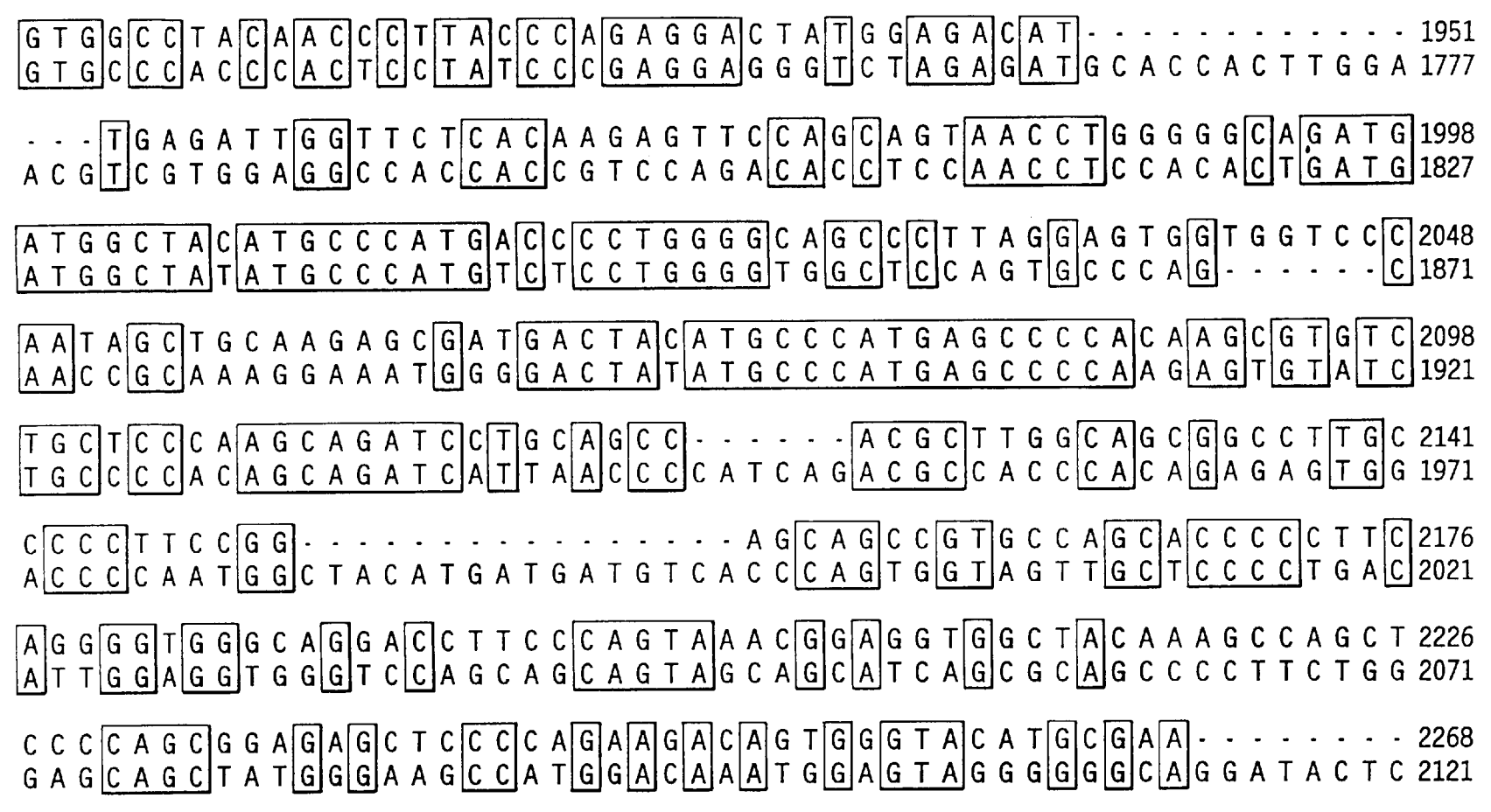
Figure 4:
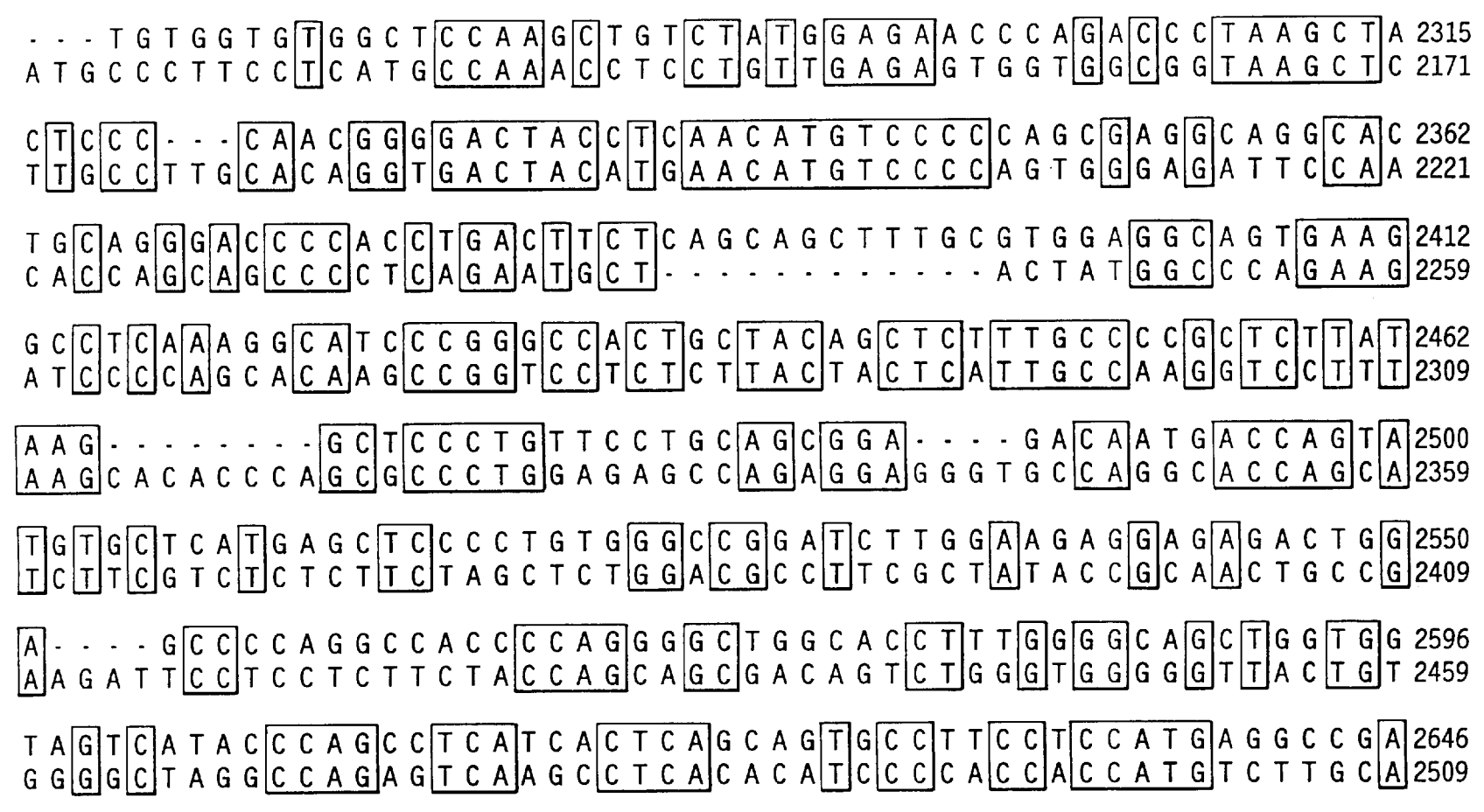
Figure 4:
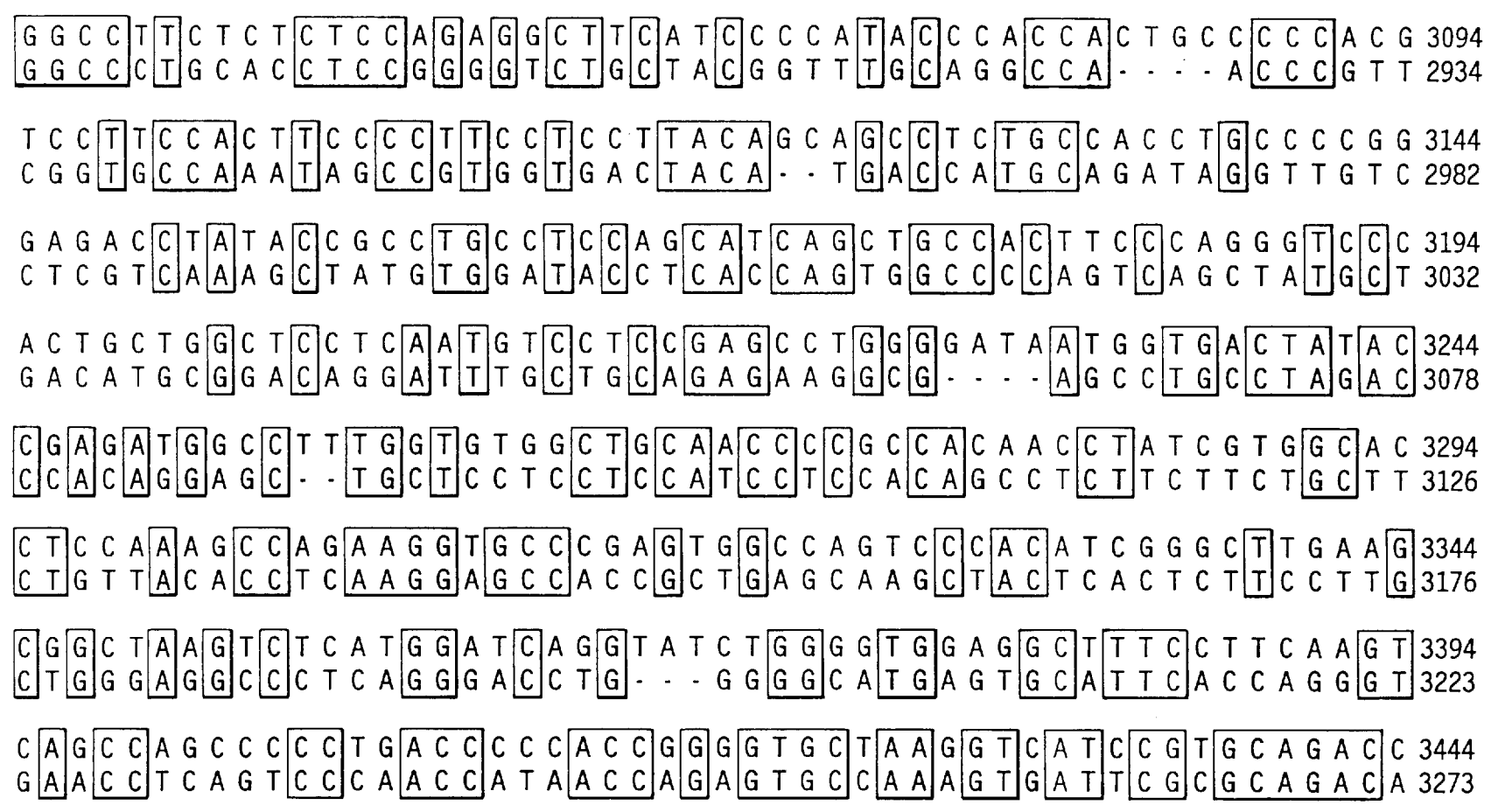
Figure 5:
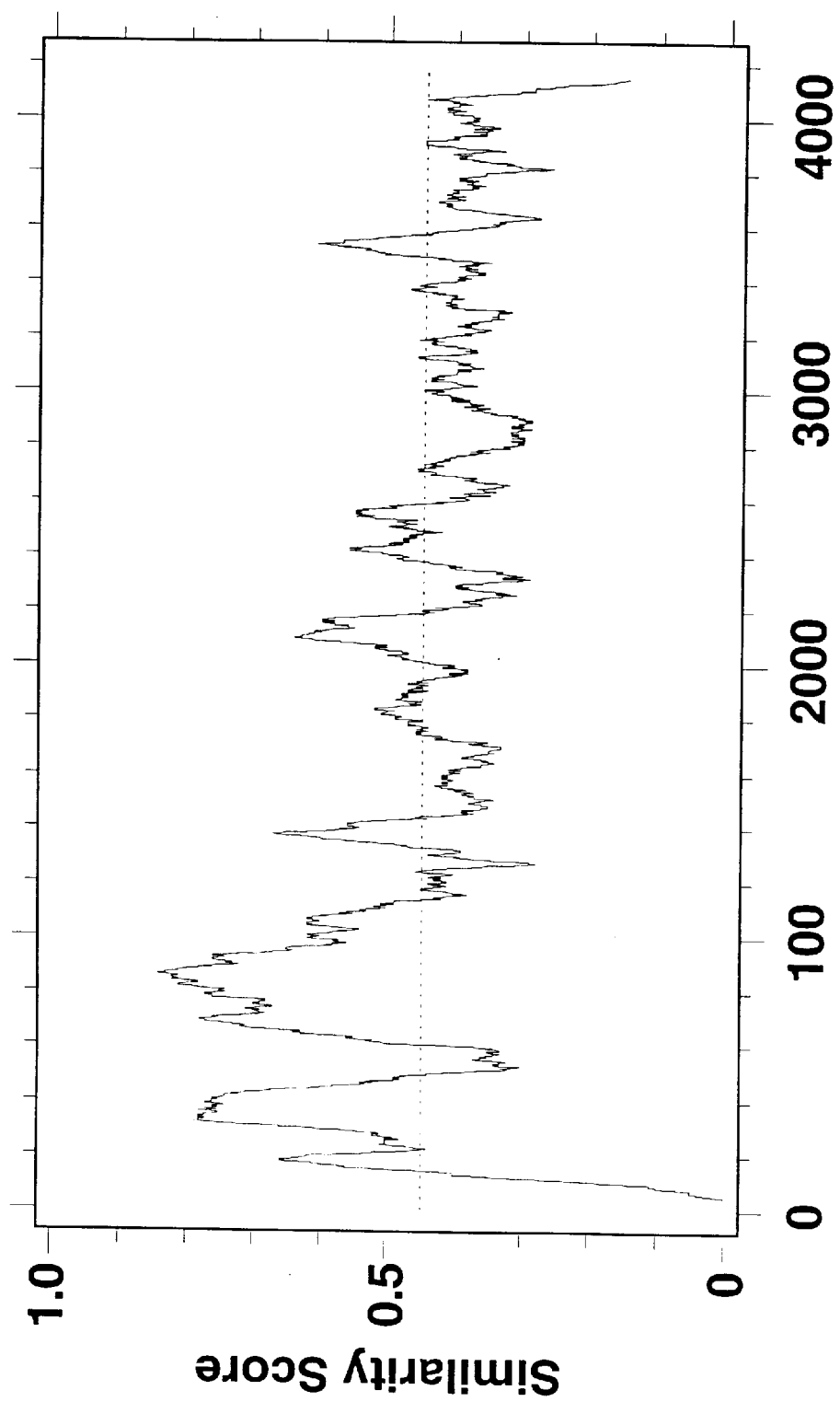
FIG. 5 is a graph of the similarity between the cDNA sequence of IRS-1 and IRS-2.

The partial cDNA is 4100 bp long and contains an open reading frame which extends from a Kozac start site at nucleotide 40, to the first TAG stop codon at nucleotide 3900. The nucleotide sequences of IRS-2 and IRS-1 are compared in FIG. 4. There are three regions of relatively high identity in the 5'-end (reaching near 70%). The identities are shown graphically in FIG. 5.

Figure 7:
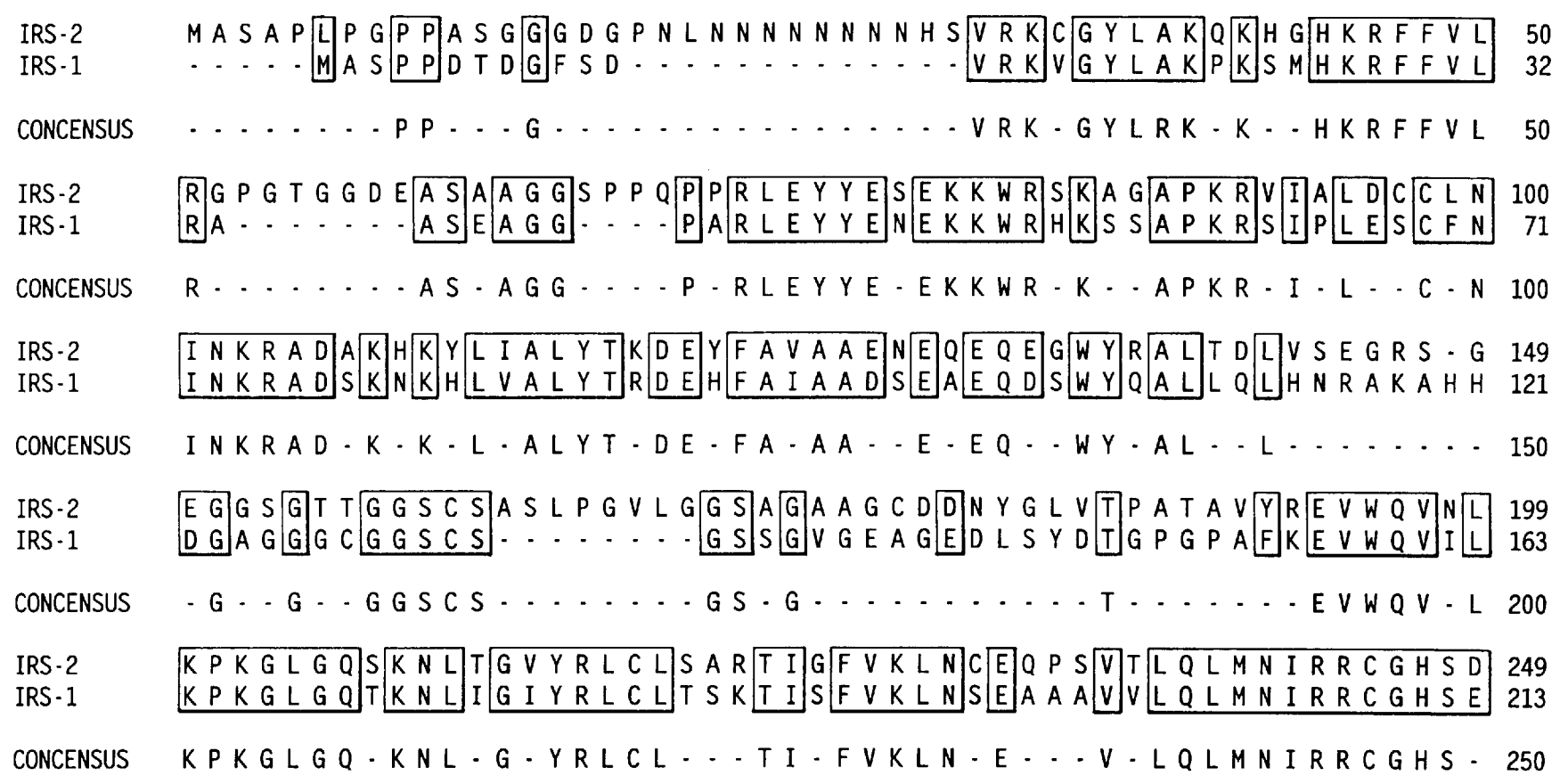

The partial cDNA sequence of IRS-2 is shown with the deduced amino acid sequence of the largest open reading frame (FIG. 6). Five out of nine peptide sequences obtained from purified IRS-2 protein were found in the deduced amino acid sequence of IRS-2. The open reading frame of IRS-2 cDNA is compared to that of IRS-1 (FIG. 7); omitting gaps, the overall identity is 51%. There are three regions of identity (65–70%) which are located in the first 500 amino acids, whereas homology in the 3'-end was less than 50% (FIG. 7).

Tissue distribution of the IRS-2 transcript was studied by northern blot of poly(A)+RNA from mouse tissues and FDCP-2 cells. The blot was probed with IRS-2 specific oligonucleotide (deduced from peptide 60) that has no homology with IRS-1 at all. IRS-2 expression was detected in heart, brain, spleen, lung, liver, skeletal muscle, kidney, testis, and FDC-P2 cells. One of ordinary skill in the art can apply routine methods to obtain IRS-2 nucleic acids from other species, e.g., humans. For example, a human IRS-2 genomic clone can be obtained by PCR cloning, using specific IRS-2 oligonucleotide primers to amplify human genomic DNA. Amplification fragments thus obtained can than be cloned into an appropriate vector, e.g., a pBluescript vector, and subsequently sequenced. Alternatively, human cDNA libraries can be screened by low stringency hybridization with an oligonucleotide probe obtained from the mouse IRS-2 sequence or with a mouse IRS-2 cDNA fragment. Positive clones obtained from either of these screens can be cloned into a vector described above and sequenced. Recombinant human polypeptide can be expressed from the isolated clones.

The amino acid sequence of IRS-2

Figure 8:
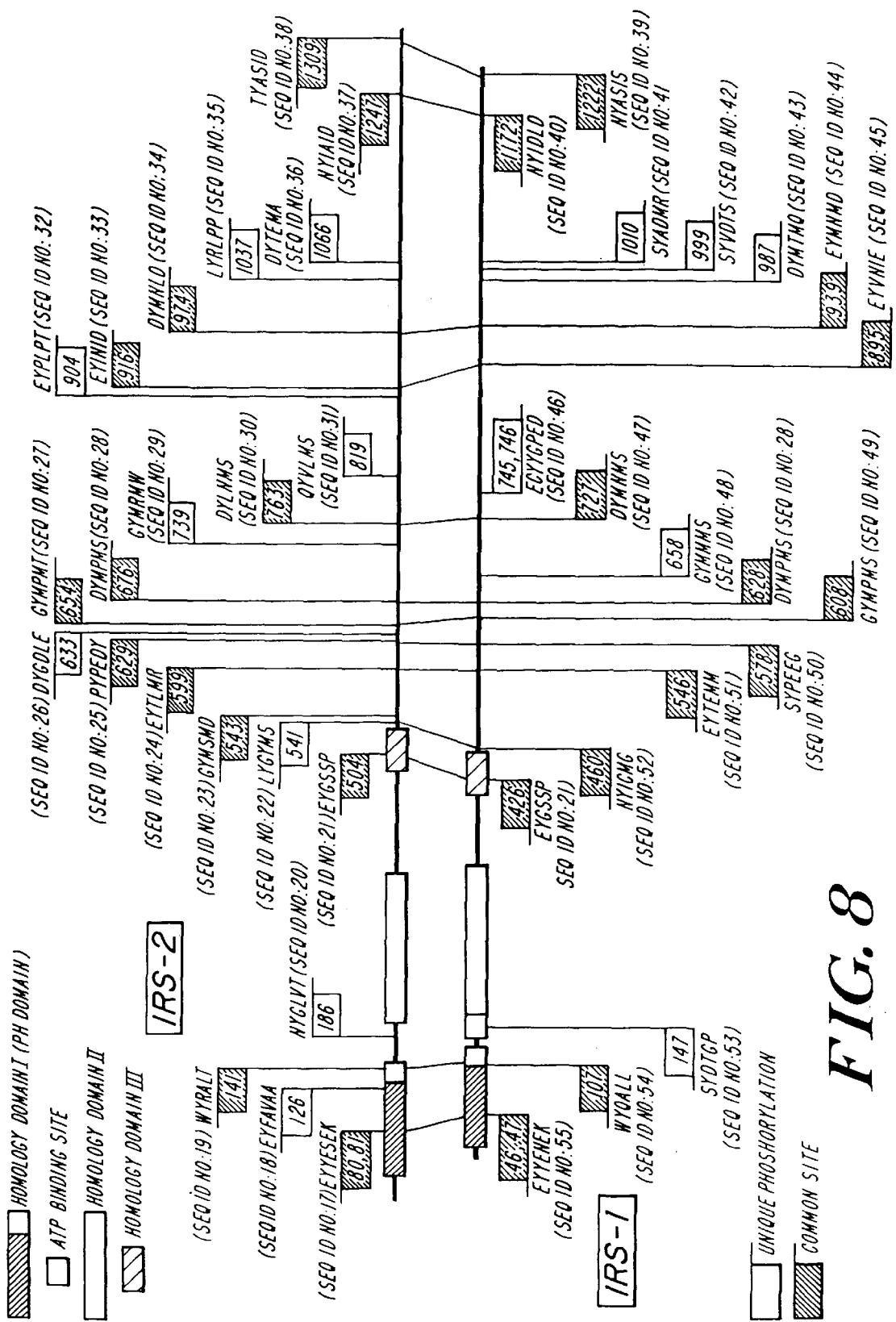
FIG. 8 is a comparison of the deduced IRS-2 amino acid sequence with that of IRS-1.

The deduced amino acid sequence of IRS-2 was compared to that of IRS-1 (FIG. 8). Most of the major phosphorylation sites and potential tyrosine phosphorylation sites in IRS-1 are conserved in IRS-2. The PH domain, which is believed to be important in the interaction with upstream kinase or downstream molecules, is highly conversed between IRS-1 and IRS-2, confirming its functional importance in the IRS-2 structure. There are three regions of similarity other than phosphorylation sites located at N-terminus, IH1, IH2, and IH3 (FIG. 8). Of particular significance, multiple phosphorylation sites are found in IRS-2 in similar position as IRS-1. In some cases the surrounding sequence of IRS-2 is very similar to IRS-1, whereas in other cases the surrounding sequence is unique (FIGS. 7 and 8). These results confirm that IRS-2 is functionally related to IRS-1 and justifies its inclusion as the second member of the IRS-signaling family.

Isolation of Other IRS Family Members

One of ordinary skill in the art can apply routine methods to obtain other IRS family members. For example, degenerate oligonucleotide primers can be synthesized from the regions of homology shared by more than one IRS gene, e.g., the IH1, IH2, or IH3 domains, of previously cloned IRS genes, e.g., IRS-1 and IRS-2. The degree of degeneracy of the primers will depend on the degeneracy of the genetic code for that particular amino acid sequence used. The degenerate primers should also contain restriction endonuclease sites at the 5' end to facilitate subsequent cloning.

Total mRNA can be obtained from a tissue, e.g., a classic insulin sensitive tissue, e.g., muscle, fat or liver tissue, and reverse transcribed using Superscript Reverse Transcriptase Kit. Instead of an oligo(dT) primer supplied with the kit, one can use one of the 3' degenerate oligonucleotide primers to increase the specificity of the reaction. After a first strand synthesis, cDNA obtained can than be subjected to a PCR amplification using above described degenerate oligonucleotides. PCR conditions should be optimized for the annealing temperature, $Mg^{++}$ concentration and cycle duration.

Once the fragment of appropriate size is amplified, it should be Klenow filled, cut with appropriate restriction enzymes and gel purified. Such fragment can than be cloned into a vector, e.g., a Bluescript vector. Clones with inserts of appropriate size can be digested with restriction enzymes to compare generated fragments with those of other IRS family members, e.g., IRS-1 and IRS-2. Those clones with distinct digestion profiles can be sequenced.

Alternatively, antibodies can be made to the conserved regions of the previously cloned IRS genes, e.g., IRS-1 or IRS-2, and used to expression screen different libraries. Yet another method includes synthesizing PCR primers from the conserved phosphorylation sites of the previously cloned IRS genes, e.g., IRS-1 and IRS-2, to make specific probes which can also be used in appropriate library screens.

The interaction of IL-4 and IRS family members

Interleukin-4 (IL-4) is a pluripotent cytokine produced by T cells, mast cells and basophiles during the immune response to pathogens. IL-4 plays an important role in the regulation of protective immune responses. It is implicated as an anti-inflammatory agent and in limiting tissue damage by autoimmunity. IL-4 is also known to play a major role in Ig class switching of B cells from IgM to IgG1 (IgG4 in human) and IgE which is commonly associated with allergic diseases (asthma and hay fever) and may play a role in immunity to helminthic parasites. The observation that IL-4 has striking antitumor activities suggests that it is a potent biologic molecule that enhances immune elimination of certain tumor cells. Thus, IL-4 plays an important role in immune response involved in many medically important processes. Like most cytokines, IL-4 has many potent biological effects on cells of varying lineage: it induces or enhances the expression of MHC Class II molecules and CD23 on B cells, its own receptor on lymphocytes, and VCAM-1 on endothelial cells. Finally, IL-4 is a growth factor for B cells, T cells and mast cells.

The IL-4 receptor complex which mediates the pleotropic effects of IL-4 exists in a wide variety of hematopoietic and nonhematopoietic cell types. The molecular cloning of cDNAs encoding both the murine and human α subunit of the IL-4 receptors (IL-4αR) and their expression in COS7 cells indicated that a single chain of ~130 kDa contains a high-affinity IL-4 binding site. However, the λ common subunit of the IL-2 receptor (IL-2$\gamma_c$ R) physically associates with IL-4αR, and is an essential component of the IL-4 receptor complex for the higher-affinity binding of IL-4 and the IL-4-induced tyrosine phosphorylation and cell growth. Both the IL-4α receptor and the IL-2γ$_c$ receptor belong to the hematopoietic receptor superfamily characterized by pairs of cysteine residues and a WSXWS (SEQ ID NO:56) motif in the extracellular domains. Both cytoplasmic domains are essential for signal transduction. A cytoplasmic domain of the IL-4α receptor contains two acidic regions and five potential tyrosine phosphorylation sites that are conserved among the human, mouse, and rat. Internal deletion studies of the IL-4α receptor have suggested that both acidic regions are required for cell proliferation in response to IL-4 in transfected Ba/F3 cells. Near the N-terminus of the second acidic region, there is an NPXY (SEQ ID NO:57) motif that is also found in the receptors for insulin and insulin-like growth factor-1. Mutations in this motif produce a receptor that fails to induce the phosphorylation of cellular proteins and proliferation in response to IL-4. The cytoplasmic domain of the IL-2γ$_c$ receptor contains an SH2 subdomain. Like other members of the hematopoietic receptor superfamily, neither the IL-4α receptor nor the IL-2γ$_c$ receptor contains any consensus sequences characteristic of tyrosine or serine/threonine kinases.

IL-4 induces the phosphorylation of IRS-2 and IRS-1 in many cell types

Although the IL-4α receptor and IL-2γ$_c$ receptor do not contain tyrosine kinase domains, IL-4 induces rapid and pronounced tyrosine phosphorylation of several proteins, including the receptor itself and IRS-2 (a 170 kDa protein-originally designated as IL-4-induced phosphotyrosine substrate (4PS)). The phosphorylation of IRS-2 is observed in many cell lines and is specific to IL-4, as IL-2, IL-3, IL-7, GM-CSF and erythropoietin do not induce the phosphorylation of IRS-2, although their receptors also belong to the hematopoietin receptor superfamily. IL-4 induces the association of phosphotidylinositol 3'-kinase (PI 3'-kinase) with IRS-2. This effect is similar to the effect of IRS-1 on PI 3'-kinase in response to insulin. Moreover, overexpressing IRS-1 in FDC-P1 and 32D myeloid progenitor cells results in the phosphorylation of IRS-1 in response to IL-4. Thus, IL-4 and insulin seem to have partially overlapping signal transduction pathways, and IRS-2 and IRS-1 possess certain structural and functional similarities.

IRS-1 is a principal insulin receptor substrate that undergoes tyrosine phosphorylation during insulin and IGF-1 stimulation. Molecular cloning of IRS-1 revealed that there is a potential nucleotide-binding site near the amino terminus, which is conserved among the rat, mouse and human. However, no other sequences characteristic of protein kinases are present. IRS-1 contains a pleckstrin homology (PH) domain between amino acid residues 7 and 120 which is the most highly conserved region of IRS-1.

IRS-1 contains over 20 potential tyrosine phosphorylation sites. At least eight tyrosyl residues have been formally identified that undergo phosphorylation by the activated insulin receptor. Tyrosine phosphorylation of IRS-1 may act as a 'molecular switch' to engage proteins with Src homology-2 domains (SH2-proteins) during insulin stimulation. The SH2 domains are composed of approximately 100 amino acids and have been found in many signaling molecules. Each particular SH2 domain is thought to associate with a phosphotyrosine present within a specific amino acid sequence motif. Phosphorylated IRS-1 associates with and activates PI 3'-kinase through the interaction of the SH2 domains present in its 85 kDa regulatory subunit (p85) with phosphotyrosines 608 and 939 within IRS-1. PI 3'-kinase is implicated in the control of cell growth and metabolism in mammals, and protein sorting in yeast. Several other SH2-proteins with distinct signaling potential have also been found to associate with phosphorylated IRS-1 including GRB-2 (p2$^{ras}$ regulation), SH-PTP2 (protein tyrosine phosphatase) and nck (an SH2/SH3 containing adapter protein). These interactions are thought to be critical for mediating insulin pleotropic actions. IRS-2 likely acts in a similar way as IRS-1 to mediate IL-4-induced pleotropic actions.

Phosphorylation of IRS-2 or IRS-2 like-proteins has also been identified in other signaling systems. In primary B cells and Bal-17 cell line, a 170 kDa protein was rapidly phosphorylated on tyrosine during IgM stimulation; a tyrosine phosphorylated protein of similar size has also been observed in a number of B cell lines, such as Daudi, U-266, and MOLT-4 and MOLT-16 cell lines in response to type I interferon see elsewhere herein. Like IRS-2, these molecules are weakly related immunologically to IRS-1 (i.e. some anti-IRS-1 antibodies weakly recognize them, whereas others do not). The identities of some of these molecules remain to be characterized. Thus, IRS-2 and IRS-1 or related molecules may define a unique group of molecules involved in a variety of signal transduction pathways.

Biological importance of IRS-2 and IRS-1

The biological importance of IRS-2 and IRS-1 in IL-4 and insulin signaling pathways has been clearly demonstrated in 32D myeloid progenitor cells which contain low levels of the high affinity IL-4 receptors and no IRS-2 or IRS-1. 32D cells did not proliferate upon exposure to IL-4 or insulin; increased expression of receptors for IL-4 or insulin in the absence of IRS-2 or IRS-1 had little effect on the mitogenic response to these factors. Expression of IRS-1 alone in these cells effectively increased the mitogenic response of cells to IL-4 and less so to insulin. However, expression of IRS-1 in the cells expressing receptors for IL-4 or insulin allowed both growth factors to induce mitogenesis extremely effectively and sustain long-term growth of these cells in the presence of individual ligand. Thus, IRS-1 appears to be an essential element for IL-4- and insulin-induced proliferation. By analogy to IRS-1, IRS-2 is likely to mediate IL-4-induced mitogenesis.

The importance of IRS-2 and IRS-1 in IL-4 signaling has also been demonstrated by the analysis of the human IL-4α receptor mutants. A truncated human IL-4α receptor (lacking the residues 437-CT) failed to phosphorylate IRS-1 when expressed in 32D/IRS-1 cells. These cells failed to proliferate when treated with hIL-4. Mutation of tyrosine 497 to phenylalanine in NPXYXS (SEQ ID NO:58) motif yielded the IL-4a receptors that caused little or no IRS-1 phosphorylation and failed to mediate 32D/IRS-1 cell proliferation during hIL-4 stimulation. Furthermore, the IL-2γ$_c$ receptor is required for IL-4-induced phosphorylation of IRS-1 and mitogenesis. In these studies, the phosphorylation of IRS-1 and IL-4-mediated proliferation is tightly associated, indicating a crucial role of IRS-1/IRS-2 in the IL-4 signaling pathways.

Surprisingly, IRS-1 (-/-) mice produced by targeted gene disruption are born alive and reproduce, although they are 50% smaller in size, indicating that IRS-1 is not essential for mammalian survival. It is reasonable to suspect that there are other IRS family molecules (perhaps IRS-2) that the insulin receptor can use to regulate cell growth and metabolic pathways. Indeed, a protein that was weakly recognized by some of the IRS-1 antibodies appeared to be phosphorylated and associate with PI 3'-kinase in liver and muscles of IRS-1 knockout mice after administration of insulin. Whether this protein is IRS-2 or not remains to be determined.

IL-4 stimulation activates a number of protein tyrosine kinases, induces tyrosine phosphorylation of cellular proteins like IRS-2 and IRS-1, and causes phosphorylation, activation and nuclear translocation of transcription factors, leading to regulating the transcription of genes that are necessary for cell growth or differentiation. However, the linkage between each of these important steps have not been clearly established yet. Since IRS-2 is believed to be crucial for IL-4-induced cell proliferation, IRS-2 likely plays an important role in this IL-4-signaling network. Modulation (e.g., inhibition or promotion) of IRS-2 activity can be used to modulate these effects.

The IRS Family and Type I Interferons

The Type I interferons (IFNα, IFNβ and IFNω) exert a variety of biological effects on normal and neoplastic cells that include antiviral and antiproliferative activities. Immediately after IFNα-stimulation, several signaling proteins in the receptor complex become tyrosine phosphorylated, including the α and β subunits of the Type I IFN receptor, and the Tyk-2 and Jak-1 tyrosine kinases. Both kinases associate with components of the Type I IFN receptor, and their activation early in the IFNα signaling cascade is presumed to regulate tyrosine phosphorylation of various downstream signaling molecules. Expression of Jak-1 and Tyk-2 rescues an IFNα response in certain insensitive cell lines, suggesting that these tyrosine kinases or related members of the Janus family are essential for IFNα action.

Several proteins are substrates for IFNα-dependent tyrosine kinase activity. In response to IFNα treatment of cells, the Stat-113, Stat-91, and Stat-84 components of the transcriptional activator ISGF3α are rapidly phosphorylated on tyrosine and associate with a 48 kD protein (ISGF3γ) to form an active complex. This complex translocates to the nucleus and initiates gene transcription during binding to interferon-stimulated response elements (ISREs). In addition, the vav proto-oncogene product ($p95^{vav}$) is tyrosine phosphorylated during IFNα stimulation; however, its precise role in the signal transduction of IFNα remains to be determined. The involvement of multiple pathways in IFNα-signaling is consistent with its pleiotropic biological effects on cells and tissues.

Many growth factor receptors, including those for epidermal growth factor and platelet-derived growth factor, associate directly through their autophosphorylation sites with a common set of signaling proteins that contain SH2 domains, including the phosphatidylinositol 3-kinase, Grb-2, SH-PTP2, PLCγ, and rasGAP. To date, there is no evidence for a direct interaction between the components of the Type I IFN-receptor and such SH2-proteins. Similarly, the receptors for insulin, IGF-1, and IL-4 do not strongly associate with known SH2-proteins. Instead, they stimulate tyrosine phosphorylation of docking proteins in the IRS-signaling family, notably IRS-1, which directly binds to various SH2-proteins. IRS-1 contains 21 potential tyrosine phosphorylation sites and migrates at approximately 175 kDa during SDS-PAGE. Both IFNα and insulin stimulate tyrosine phosphorylation of a common 170–175 kDa protein in hematopoietic cells, suggesting that IFNα uses an IRS-signaling protein to mediate certain biologic responses. (Patterns of tyrosine phosphorylation induced by IFNα or insulin were studied in U-266 cells as follows: Cells were incubated in the presence of absence of $10^4$ U/ml of IFNα for 5 min at 37° C. as indicated. Cells were either not stimulated or stimulated with 1 μM of insulin for either 5 min or 30 min at 37° C. Equal amounts of protein from total cell lysates (100 μg) were analyzed by SDS-PAGE and immunoblotted with an anti-phosphotyrosine monoclonal antibody (4G-10). Cell lysis and immunoblotting using an enhanced chemiluminesence (ECL) method were performed by standard methods.)

To determine whether IRS-1 is involved in IFNα signaling, cell lysates from control or stimulated U-266 or Daudi cells were immunoprecipitated with a polyclonal antibody against recombinant rat IRS-1 and immunoblotted with an antiphosphotyrosine antibody (4G-10). Basal tyrosine phosphorylation of a 170 kDa protein was reproducibly detected in U-266 but not in Daudi cells. IFNα and insulin strongly stimulated tyrosine phosphorylation of the 170 kDa protein in the αIRS-1 immunoprecipitates from both cell lines. (Tyrosine phosphorylation of a 170 kD IRS-signaling protein in response to IFNα and insulin was determined as follows: U-266 or Daudi cells were incubated in the presence of absence of IFNα ($10^4$ U/ml) or insulin (1 μM) for 3 min at 37° C. Cell lysates were immunoprecipitated with either control normal rabbit immunoglobulin (RIgG) (Sigma) or an antibody against baculovirus-generated rat IRS-1 as indicated. Cells were stimulated with $10^4$ U/ml of IFNα for various time points and cell lysates were immunoprecipitated with either control antibody (RIgG) or an antibody against recombinant rat IRS-1. Immunoprecipitates were analyzed by SDS-PAGE, transferred to polivinidyl-fluoride membranes (Immobilon, Millipore), and immunoblotted with antiphosphotyrosine. The blots were developed using the ECL method. The bands migrating above and below the IRS-signaling protein in the blot, are non-specific.)

Phosphorylation of the 170 kDa protein occurred within one minute of treatment of Daudi or Molt-4 cells with IFNα, and diminished after 90 minutes. This phosphoprotein was also immunoprecipitated by an antibody against the pleckstrin homology (PH) domain of IRS-1 ($\alpha IRS-1^{PH}$). (Association of the IRS-signaling protein with the p85 regulatory subunit of PI 3' -kinase in Daudi cells were studied as follows: Cells ($4 \times 10^7$/lane) were stimulated for 5 min at 37° C. with either IFNα (104 u/ml) as indicated, and cell lysates were immunoprecipitated with either normal RIgG, or a polyclonal antibody against the p85 regulatory subunit of PI 3'-kinase, or a polyclonal antibody against the pleckstrin homology domain of IRS-1 ($\alpha IRS-1^{PH}$) as indicated. Immunoprecipitates were analyzed by SDS-PAGE and immunoblotted with antiphosphotyrosine. In other experiments, cells ($5 \times 10^7$/lane) were incubated in the presence or absence of IFNα or insulin for 7 min at 37° C., and cell lysates were immunoprecipitated with an antibody against the pleckstrin homology domain of IRS-1, or a polyclonal antibody against p85 or normal RIgG. Immunoprecipitates were analyzed by SDS-PAGE and immunoblotted with a monoclonal antibody against p85 α (Upstate Biotechnology). In other experiments cells ($9 \times 10^7$/lane) were stimulated with IFNα or insulin for 5 minutes at 37° C. as indicated, and cell lysates were incubated for 3 hours at 4° C. with either GST alone or a GST fusion protein containing the N-terminal SH2 domain of p85α (amino acid residues 321 to 440), both of which were bound to glutathione-sepharose beads (Pharmacia). The beads were washed, and the bound proteins were separated by SDS-PAGE, transferred to polyvinidyl-fluoride membranes, and immunoblotted with antiphosphotyrosine. The blots were developed using the ECL method. The bands migrating above and below the IRS signaling protein in the blots are non-specific.)

Despite its strong reactivity with the $\alpha IRS-1^{PH}$ antibody, this protein is not identical to IRS-1 as it was not recognized by antibodies against specific sequences present in the C- or N-terminus of IRS-1. It has not yet been determined if this is the same protein as IRS-2.

After tyrosine phosphorylation, IRS-1 binds to several SH2-proteins, including the 85 kDa regulatory subunit (p85)

of the phosphatidylinositol 3'-kinase. To determine whether the 170 kD IRS-related phosphoprotein binds p85 during IFNα stimulation, immunoprecipitates obtained with an anti-p85 antibody from Daudi-cell lysates were immunoblotted with antiphosphotyrosine (4G-10). Following IFNα or insulin treatment of the cells, a 170 kDa tyrosine phosphorylated protein was detected in the anit-p85 immunoprecipitates. This phosphoprotein co-migrated with the 170 kD IRS-related protein immunoprecipitated directly with αIRS-1$^{PH}$. Moreover, immunoprecipitates obtained with the αIRS-1$^{PH}$ antibody contained p85α only after IFNα or insulin stimulation. The IRS-related phosphoprotein from IFNα- or insulin-stimulated cells also bound to a GST fusion protein containing the N-terminal SH2 domain of p85. Similar results were obtained using a GST fusion protein containing the C-terminal SH2 domain of p85. Thus, both IFNα and insulin stimulate the association of an IRS-signaling protein with the PI 3'-kinase, and this interaction most likely requires the SH2 domains in p85.

The phosphatidylinositol 3'-kinase (PI 3'-kinase) appears to play an important role in various biological responses and is activated by many growth factors and cytokines. Its activation by insulin occurs during association with tyrosine phosphorylated IRS-1. To determine whether IFNα stimulates the association of PI 3'-kinase activity with the IRS-signaling protein in Daudi cells, PI 3'-kinase assays were carried out on αIRS-1$^{PH}$ immunoprecipitates. Before stimulation, a basal level of PI 3'-kinase activity was detected in the immunoprecipitates of αIRS-1$^{PH}$, which was equivalent to the nonspecific activity detected in immunoprecipitates with preimmune rabbit serum. (Activation of the PI 3'-kinase by IFNα and insulin in Daudi cells was studied as follows: Cells were treated for 5 minutes in the absence or presence of IFNα (104 U/ml) or insulin (100 nM) as indicated, cell lysates were immunoprecipitated with the αIRS-1$^{PH}$ antibody or preimmune serum, and immunoprecipitates were assayed in triplicates for PI 3'-kinase activity.) IFNα or insulin stimulated the association of PI 3'-kinase activity with the IRS-related protein that was immunocipitated specifically with αIRS-1$^{PH}$. It is likely that the PI 3'-kinase is activated by the IFNα or insulin during its association with the IRS-signaling protein.

Considerable progress has been made in the understanding of IFNα-signaling between the plasma membrane and nucleus. The Jak-Stat pathway provides a plausible mechanism for the regulated assembly of ISGF-3 which regulates expression of genes containing the IFN-stimulated response elements (ISREs). The molecular mechanism used by IFNα to regulate other signaling pathways however is less than fully understood. The finding that IFNα stimulates tyrosine phosphorylation of a 170 kDa IRS-signaling protein suggest the existence of a pathway for the regulated engagement of additional SH2-signaling proteins during IFNα stimulation. Until now, a molecular link between the Type I IFN receptor and the PI 3'-kinase, Grb-2, SH-PTP2, and nck has been absent. Tyrosine phosphorylation of IRS-1 or a related protein provides a direct link to these downstream signaling elements. The 170 kD phosphoprotein in Daudi, U-266, and Molt-4 cells is related but not identical to IRS-1 as determined by its reactivity pattern with antibodies against different regions of IRS-1. It is, however, functionally similar to IRS-1 as it is tyrosine phosphorylated during insulin stimulation and binds to the PI 3'-kinase. It will be important to identify other SH2-proteins engaged by this IRS-related protein in response to IFNα, as well as in response to IFNβ and IFNω, which also induce tyrosine phosphorylation of the same protein.

Studies in hematopoietic cells suggested the existence of a 170 kDa IRS-related protein that was tyrosine phosphorylated during IL-4 or insulin stimulation. This protein, originally called 4PS (now termed IRS-2), binds PI 3'-kinase after tyrosine phosphorylation and reacts strongly with αIRS-1$^{PH}$ but not with C- and N-terminal specific αIRS-1 antibodies. The characteristics of IRS-2 appear identical to those of the 170 kDa IRS-signaling protein detected in Daudi, U-266, and Molt-4 cells during IFNα or insulin stimulation. IRS-2 was purified from insulin-stimulation FCD-P2 cells and optimized cDNA probes prepared from partial amino acid sequence used to isolate its cDNA. The deduced amino acid sequence predicts a protein that is approximately 48% identical to IRS-1, but contains a well-conserved PH-domain which explains its strong reactivity with the αIRS-1$^{PH}$ antibody. Provisionally called IRS-2, this new member of the IRS-signaling family may be identical to the 170 kDa phosphoprotein detected during IFNα stimulation; however, additional isoforms may exist and so definitive demonstration awaits the preparation of specific antibodies against IRS-2.

IRS-signaling proteins contain many potential tyrosine phosphorylation sites in various hydrophobic contexts. These tyrosine residues play a dual role as substrates for upstream tyrosine kinases and as specific docking sites for downstream SH2-proteins. At least eight tyrosines residues in IRS-1 undergo phosphorylation by the activated insulin receptor, including residues 460, 608, 628, 939, and 987, which are in YXXM (SEQ ID NO:59)/YMXM (SEQ ID NO:2) motifs and bind to p85 which activates the PI 3'-kinase. Three other motifs are also phosphorylated by the insulin receptor, including Y$^{895}$VNI (SEQ ID NO:60) which binds Grb-2, and Y$^{1721}$IDL (SEQ ID NO:61) and Y$^{1222}$ASI (SEQ ID NO:62) which bind SH-PTP2 (23). Many, but not all these sites are conserved in IRS-2, suggesting that differential expression of IRS-1 and IRS-2, together with unique phosphorylation patterns achieved during insulin, IL-4, or IFNα stimulation may play an important role in signaling specificity.

The insulin receptor tyrosine kinase appears to regulate the insulin-dependent phosphorylation of IRS-signaling proteins, whereas the receptors for IL-4 and IFNα use Janus family tyrosine kinases to accomplish such phosphorylation; however, direct evidence for the involvement of Janus kinases during IFNα and IL-4 stimulation remains to be obtained. Many receptors activate the Janus family of tyrosine kinases, but most of them do not phosphorylate IRS-signaling proteins. The identity of the elements responsible for this selectivity are unknown. Interestingly, the receptors for insulin, IGF-1, and IL-4 contain a common amino acid sequence motif, LxxxxNPxYxss, (SEQ ID NO:63) which appears to contribute to the interaction of these receptors with IRS-1; however this sequence motif is not found in the cloned components of the Type I IFN receptor, suggesting that a different motif may be involved or another subunit remains to be found.

The shared use of the IRS-signaling pathway establishes a common link between apparently distinct signaling systems for insulin, IGF-1, IL-4, and IFNα. IL-4 may attenuate the transcriptional activation of IFN-induced cellular gene expression in monocytes and related cell lines. The results suggest an antagonism between IFNα and IL-4 occurring through the common use of proteins in the IRS-signaling system. If it is correct, then insulin and IGF-1 may also influence IFNα-signaling.

Gene Therapy

The gene constructs of the invention can also be used as a part of a gene therapy protocol to deliver nucleic acids encoding either an agonistic or antagonistic form of an IRS polypeptide (preferably other than IRS-1), e.g., an IRS-2 polypeptide. In the case of IRS-2, the invention features expression vectors for in vivo transfection and expression of an IRS-2 polypeptide in particular cell types so as to reconstitute the function of, or alternatively, abrogate the function of IRS-2 polypeptide in a cell in which that IRS-2 is misexpressed. Expression constructs of the subject IRS-2 polypeptide, and mutants thereof, may be administered in any biologically effective carrier, e.g. any formulation or composition capable of effectively delivering the IRS-2 gene to cells in vivo. Approaches include insertion of the subject gene in viral vectors including recombinant retroviruses, adenovirus, adeno-associated virus, and herpes simplex virus-1, or recombinant bacterial or eukaryotic plasmids. Viral vectors transfect cells directly; plasmid DNA can be delivered with the help of, for example, cationic liposomes (lipofectin) or derivatized (e.g. antibody conjugated), polylysine conjugates, gramacidin S, artificial viral envelopes or other such intracellular carriers, as well as direct injection of the gene construct or $CaPO_4$ precipitation carried out in vivo. It will be appreciated that because transduction of appropriate target cells represents the critical first step in gene therapy, choice of the particular gene delivery system will depend on such factors as the phenotype of the intended target and the route of administration, e.g. locally or systemically. Furthermore, it will be recognized that the particular gene construct provided for in vivo transduction of IRS-2 expression are also useful for in vitro transduction of cells, such as for use in the diagnostic assays described above.

A preferred approach for in vivo introduction of nucleic acid into a cell is by use of a viral vector containing nucleic acid, e.g. a cDNA, encoding the IRS-2 polypeptide. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells which have taken up viral vector nucleic acid.

Retrovirus vectors and adeno-associated virus vectors can be used as a recombinant gene delivery system for the transfer of exogenous genes in vivo, particularly into humans. These vectors provide efficient delivery of genes into cells, and the transferred nucleic acids are stably integrated into the chromosomal DNA of the host. A major prerequisite for the use of retroviruses is to ensure the safety of their use, particularly with regard to the possibility of the spread of wild-type virus in the cell population. The development of specialized cell lines (termed "packaging cells") which produce only replication-defective retroviruses has increased the utility of retroviruses for gene therapy, and defective retroviruses are well characterized for use in gene transfer for gene therapy purposes (for a review see Miller, A.D. (1990) *Blood* 76:271). Thus, recombinant retrovirus can be constructed in which part of the retroviral coding sequence (gag, pol, env) has been replaced by nucleic acid encoding one of the subject receptors rendering the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses can be found in *Current Protocols in Molecular Biology*, Ausubel, F. M. et al. (eds.) Greene Publishing Associates, (1989), Sections 9.10–9.14 and other standard laboratory manuals. Examples of suitable retroviruses include pLJ, pZIP, pWE and pEM which are well known to those skilled in the art. Examples of suitable packaging virus lines for preparing both ecotropic and amphotropic retroviral systems include ψCrip, ψCre, ψ2 and ψAm. Retroviruses have been used to introduce a variety of genes into many different cell types, including epithelial cells, in vitro and/or in vivo (see for example Eglitis, et al. (1985) *Science* 230:1395–1398; Danos and Mulligan (1988) *Proc. Natl. Acad. Sci. USA* 85:6460–6464; Wilson et al. (1988) *Proc. Natl. Acad. Sci. USA* 85:3014–3018; Armentano et al. (1990) *Proc. Natl. Acad. Sci. USA* 87:6141–6145; Huber et al. (1991) *Proc. Natl. Acad. Sci. USA* 88:8039–8043; Ferry et al. (1991) *Proc. Natl. Acad. Sci. USA* 88:8377–8381; Chowdhury et al. (1991) *Science* 254:1802–1805; van Beusechem et al. (1992) *Proc. Natl. Acad. Sci. USA* 89:7640–7644; Kay et al. (1992) *Human Gene Therapy* 3:641–647; Dai et al. (1992) *Proc. Natl. Acad. Sci. USA* 89:10892–10895; Hwu et al. (1993) *J. Immunol.* 150:4104–4115; U.S. Pat. No. 4,868,116; U.S. Pat. No. 4,980,286; PCT Application WO 89/07136; PCT Application WO 89/02468; PCT Application WO 89/05345; and PCT Application WO 92/07573).

In choosing retroviral vectors as a gene delivery system for the subject IRS-2 gene, it is important to note that a prerequisite for the successful infection of target cells by most retroviruses, and therefore of stable introduction of the recombinant IRS-2 gene, is that the target cells must be dividing. With certain exceptions, such as lymphatic cancers, such a requirement will not be a hindrance to use of retroviral vectors.

Furthermore, it has been shown that it is possible to limit the infection spectrum of retroviruses and consequently of retroviral-based vectors, by modifying the viral packaging proteins on the surface of the viral particle (see, for example PCT publications W093/25234 and W094/06920). For instance, strategies for the modification of the infection spectrum of retroviral vectors include: coupling antibodies specific for cell surface antigens to the viral env protein (Roux et al. (1989) *PNAS* 86:9079–9083; Julan et al. (1992) *J. Gen Virol* 73:3251–3255; and Goud et al. (1983) *Virology* 163:251–254); or coupling cell surface receptor ligands to the viral env proteins (Neda et al. (1991) *J Biol Chem* 266:14143–14146). Coupling can be in the form of the chemical cross-linking with a protein or other variety (e.g. lactose to convert the env protein to an asialoglycoprotein), as well as by generating fusion proteins (e.g. single-chain antibody/env fusion proteins). This technique, while useful to limit or otherwise direct the infection to certain tissue types, can also be used to convert an ecotropic vector in to an amphotropic vector.

Moreover, use of retroviral gene delivery can be further enhanced by the use of tissue- or cell-specific transcriptional regulatory sequences which control expression of the IRS-2 gene of the retroviral vector.

Another viral gene delivery system useful in the present invention utilizes adenovirus-derived vectors. The genome of an adenovirus can be manipulated such that it encodes and expresses a gene product of interest but is inactivated in terms of its ability to replicate in a normal lytic viral life cycle. See, for example, Berkner et al. (1988) *BioTechniques* 6:616; Rosenfeld et al. (1991) *Science* 252:431–434; and Rosenfeld et al. (1992) *Cell* 68:143–155. Suitable adenoviral vectors derived from the adenovirus strain Ad type 5 dl324 or other strains of adenovirus (e.g., Ad2, Ad3, Ad7 etc.) are well known to those skilled in the art. Recombinant adenoviruses can be advantageous in certain circumstances in that they are not capable of infecting nondividing cells and can be used to infect a wide variety of cell types, including epithelial cells (Rosenfeld et al. (1992) cited supra). Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al. cited supra; Haj-Ahmand and Graham (1986) *J. Virol.* 57:267). Most replication-defective adenoviral vectors currently in use and therefore favored by the present invention are deleted for all or parts of the viral E1 and E3 genes but retain as much as 80% of the adenoviral genetic material (see, e.g., Jones et al. (1979) *Cell* 16:683; Berkner et al., supra; and Graham et al. in *Methods in Molecular Biology*, E. J. Murray, Ed. (Humana, Clifton, N.J., 1991) vol. 7. pp. 109–127). Expression of the inserted IRS-2 gene can be under control of, for example, the E1A promoter, the major late promoter (MLP) and associated leader sequences, the E3 promoter, or exogenously added promoter sequences.

Yet another viral vector system useful for delivery of the subject IRS-2 gene is the adeno-associated virus (AAV). Adeno-associated virus is a naturally occurring defective virus that requires another virus, such as an adenovirus or a herpes virus, as a helper virus for efficient replication and a productive life cycle. (For a review see Muzyczka et al. *Curr. Topics in Micro. and Immunol.* (1992) 158:97–129). It is also one of the few viruses that may integrate its DNA into non-dividing cells, and exhibits a high frequency of stable integration (see for example Flotte et al. (1992) *Am. J. Respir. Cell. Mol. Biol.* 7:349–356; Samulski et al. (1989) *J. Virol.* 63:3822–3828; and McLaughlin et al. (1989) *J. Virol.* 62:1963–1973). Vectors containing as little as 300 base pairs of AAV can be packaged and can integrate. Space for exogenous DNA is limited to about 4.5 kb. An AAV vector such as that described in Tratschin et al. (1985) *Mol. Cell. Biol.* 5:3251–3260 can be used to introduce DNA into cells. A variety of nucleic acids have been introduced into different cell types using AAV vectors (see for example Hermonat et al. (1984) *Proc. Natl. Acad. Sci. USA* 81:6466–6470; Tratschin et al. (1985) *Mol. Cell. Biol.* 4:2072–2081; Wondisford et al. (1988) *Mol. Endocrinol.* 2:32–39; Tratschin et al. (1984) *J. Virol.* 51:611–619; and Flotte et al. (1993) *J. Biol. Chem.* 268:3781–3790).

In addition to viral transfer methods, such as those illustrated above, non-viral methods can also be employed to cause expression of an IRS-2 polypeptide in the tissue of an animal. Most nonviral methods of gene transfer rely on normal mechanisms used by mammalian cells for the uptake and intracellular transport of macromolecules. In preferred embodiments, non-viral gene delivery systems of the present invention rely on endocytic pathways for the uptake of the subject IRS-2 gene by the targeted cell. Exemplary gene delivery systems of this type include liposomal derived systems, poly-lysine conjugates, and artificial viral envelopes.

In a representative embodiment, a gene encoding IRS-2 polypeptide can be entrapped in liposomes bearing positive charges on their surface (e.g., lipofectins) and (optionally) which are tagged with antibodies against cell surface antigens of the target tissue (Mizuno et al. (1992) *No Shinkei Geka* 20:547–551; PCT publication W091/06309; Japanese patent application 1047381; and European patent publication EP-A-43075).

In clinical settings, the gene delivery systems for the therapeutic IRS-2 gene can be introduced into a patient by any of a number of methods, each of which is familiar in the art. For instance, a pharmaceutical preparation of the gene delivery system can be introduced systemically, e.g. by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by Stereotactic injection (e.g. Chen et al. (1994) *PNAS* 91: 3054–3057).

The pharmaceutical preparation of the gene therapy construct can consist essentially of the gene delivery system in an acceptable diluent, or can comprise a slow release matrix in which the gene delivery vehicle is imbedded. Alternatively, where the complete gene delivery system can be produced in tact from recombinant cells, e.g. retroviral vectors, the pharmaceutical preparation can comprise one or more cells which produce the gene delivery system.

Peptide Mimetics

The invention also provides for reduction of the protein binding domains of the subject IRS polypeptides (preferably other than IRS-1), e.g., an IRS-2 polypeptide, to generate mimetics, e.g. peptide or non-peptide agents, which are able to disrupt binding, in this case, of an IRS-2 of the present invention with an IRS-2 binding protein, e.g., naturally occurring ligand, e.g., an insulin receptor. Thus, such mutagenic techniques are particularly useful to map the determinants of the IRS-2 which participate in protein-protein interactions involved in, for example, binding of the subject IRS-2 polypeptide to an IRS-2 binding protein. To illustrate, the critical residues of a subject IRS-2 polypeptide which are involved in molecular recognition of an IRS-2 binding protein can be determined and used to generate IRS-2-derived peptidomimetics which competitively inhibit binding of the IRS-2 with an IRS-2 binding protein (see, for example, "Peptide inhibitors of human papillomavirus protein binding to retinoblastoma gene protein" European patent applications EP-412,762A and EP-B31,080A). By employing, for example, scanning mutagenesis to map the amino acid residues of a particular IRS-2 polypeptide involved in binding an IRS-2 binding protein, peptidomimetic compounds (e.g. diazepine or isoquinoline derivatives) can be generated which mimic those residues in binding to an IRS-2 binding protein, and which therefore can inhibit binding of the IRS-2 to an IRS-2 binding protein and thereby interfere with the function of IRS-2. For instance, non-hydrolyzable peptide analogs of such residues can be generated using benzodiazepine (e.g., see Freidinger et al. in *Peptides: Chemistry and Biology*, G. R. Marshall ed., ESCOM Publisher: Leiden, Netherlands, 1988), azepine (e.g., see Huffman et al. in *Peptides: Chemistry and Biology*, G. R. Marshall ed., ESCOM Publisher: Leiden, Netherlands, 1988), substituted gama lactam rings (Garvey et al. in *Peptides: Chemistry and Biology*, G. R. Marshall ed., ESCOM Publisher: Leiden, Netherlands, 1988), keto-methylene pseudopeptides (Ewenson et al. (1986) *J Med Chem* 29:295; and Ewenson et al. in *Peptides: Structure and Function* (Proceedings of the 9th American Peptide Symposium) Pierce Chemical Co. Rockland, Ill., 1985), β-turn dipeptide cores (Nagai et al. (1985) *Tetrahedron Lett* 26:647; and Sato et al. (1986) *J Chem Soc Perkin Trans* 1:1231), and β-aminoalcohols (Gordon et al. (1985) *Biochem Biophys Res Commun* 126:419; and Dann et al. (1986) *Biochem Biophys Res Commun* 134:71).

Drug Screening Assays

By making available purified and recombinant IRS polypeptides (preferably other than IRS-1), e.g., IRS-2 polypeptide, the present invention provides assays which can be used to screen for drugs which are either agonists or antagonists of the normal cellular function, in this case, of the subject IRS-2 polypeptides, or of their role in insulin related disorders. In one embodiment, the assay evaluates the ability of a compound to modulate binding between an IRS-2 polypeptide and an IRS-2 binding protein, e.g. naturally occurring ligand, e.g., an insulin receptor. A variety of assay formats will suffice and, in light of the present inventions, will be comprehended by skilled artisan.

In many drug screening programs which test libraries of compounds and natural extracts, high throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test compound. Moreover, the effects of cellular toxicity and/or bioavailability of the test compound can be generally ignored in the in vitro system, the assay instead being focused primarily on the effect of the drug on the molecular target as may be manifest in an alteration of binding affinity with other proteins or change in enzymatic properties of the molecular target. Accordingly, in an exemplary screening assay of the present invention, the compound of interest is contacted with an isolated and purified IRS-2 polypeptide. The mixture of the compound and IRS-2 polypeptide is then added to a composition containing an IRS-2 binding protein but which does not contain IRS-2. Detection and quantification of IRS-2/IRS-2 binding protein complexes provides a means for determining the compound's efficacy at inhibiting (or potentiating) complex formation between the IRS-2 polypeptide and the IRS-2 binding protein. The efficacy of the compound can be assessed by generating dose response curves from data obtained using various concentrations of the test compound. Moreover, a control assay can also be performed to provide a baseline for comparison. In the control assay, isolated and purified IRS-2 is added to a composition containing the IRS-2 polypeptide, and the formation of IRS-2/IRS-2 binding protein complex is quantitated in the absence of the test compound.

Other Embodiments

The embodiments below are described with IRS-2, but they can be applied to other members of the IRS family (preferably other than IRS- 1).

Included in the invention are: allelic variations; natural mutants; induced mutants; proteins encoded by DNA that hybridizes under high or low stringency conditions to a nucleic acid which encodes the polypeptide of SEQ ID NO:1 (for definitions of high and low stringency see Current Protocols in Molecular Biology, John Wiley & Sons, New York, 1989, 6.3.1–6.3.6, hereby incorporated by reference); and, polypeptides specifically bound by antisera to IRS-2, especially by antisera to an active site or binding domain of IRS-2.

The invention also includes biologically active fragments or analogs of IRS-2. A biologically active fragment or analog is one having any in vivo or in vitro activity which is characteristic of the IRS-2 shown in SEQ ID NO:1, e.g., one or more of the biological activities described above. Because peptides such as IRS-2 often exhibit a range of physiological properties and because such properties may be attributable to different portions of the molecule, a useful IRS-2 fragment or IRS-2 analog is one which exhibits a biological activity in any biological assay for IRS-2 activity. Most preferably the fragment or analog possesses 10%, preferably 40%, or at least 90% of the activity of IRS-2 (SEQ ID NO:1), in any in vivo or in vitro IRS-2 assay.

Analogs can differ from naturally occurring IRS-2 in amino acid sequence or in ways that do not involve sequence, or both. Analogs of the invention will generally exhibit at least 90%, preferably 95% or even 99%, homology with a segment of 20 amino acid residues, preferably more than 40 amino acid residues, or more preferably the entire sequence of a naturally occurring IRS-2 sequence. Non-sequence modifications include in vivo or in vitro chemical derivatization of IRS-2's. Non-sequence modifications include changes in acetylation, methylation, phosphorylation, carboxylation, or glycosylation. Glycosylation can be modified, e.g., by modifying the glycosylation patterns of an IRS-2 during its synthesis and processing or in further processing steps, e.g., by exposing the IRS-2 to glycosylation affecting enzymes derived from cells that normally provide such processing, e.g., mammalian glycosylation enzymes; phosphorylation can be modified by exposing the IRS-2 to phosphorylation-altering enzymes, e.g., kinases or phosphatases.

Preferred analogs include IRS-2 (or biologically active fragments thereof) whose sequences differ from the wild-type sequence by one or more conservative amino acid substitutions or by one or more non-conservative amino acid substitutions, deletions, or insertions which do not abolish the IRS-2's biological activity. Conservative substitutions typically include the substitution of one amino acid for another with similar characteristics, e.g., substitutions within the following groups: valine, glycine; glycine, alanine; valine, isoleucine, leucine; aspartic acid, glutamic acid; asparagine, glutamine; serine, threonine; lysine, arginine; and phenylalanine, tyrosine. Other conservative substitutions can be taken from the table below.

TABLE 3

CONSERVATIVE AMINO ACID REPLACEMENTS

| For Amino Acid | Code | Replace with any of |
|---|---|---|
| Alanine | A | D-Ala, Gly, beta-Ala, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me—Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, β-Ala Acp |
| Isoleucine | I | D-Ile, Val, D-Val, Leu, D-Leu, Met, D-Met |

TABLE 3-continued

CONSERVATIVE AMINO ACID REPLACEMENTS

| For Amino Acid | Code | Replace with any of |
|---|---|---|
| Leucine | L | D-Leu, Val, D-Val, Leu, D-Leu, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me—Cys, Ile, D-Ile, Leu, D-Leu, Val, D-Val |
| Phenylalanine | F | D-Phe, Tyr, D-Thr, L-Dopa, His, D-His, Trp, D-Trp, Trans-3,4, or 5-phenylproline, cis-3,4, or 5-phenylproline |
| Proline | P | D-Pro, L-I-thioazolidine-4-carboxylic acid, D-or L-1-oxazolidine-4-carboxylic acid |
| Serine | S | D-Ser, Thr, D-Thr, allo-Thr, Met, D-Met, Met(O), D-Met(O), L-Cys, D-Cys |
| Threonine | T | D-Thr, Ser, D-Ser, allo-Thr, Met, D-Met, Met(O), D-Met(O), Val, D-Val |
| Tyrosine | Y | D-Tyr, Phe, D-Phe, L-Dopa, His, D-His |
| Valine | V | D-Val, Leu, D-I,eu, Ile, D-Ile, Met, D-Met |

Other analogs within the invention are those with modifications which increase peptide stability; such analogs may contain, for example, one or more non-peptide bonds (which replace the peptide bonds) in the peptide sequence. Also included are: analogs that include residues other than naturally occurring L-amino acids, e.g., D-amino acids or non-naturally occurring or synthetic amino acids, e.g., β or γ amino acids; and cyclic analogs.

As used herein, the term "fragment", as applied to an IRS-2, will ordinarily be at least about 20 residues, more typically at least about 40 residues, preferably at least about 60 residues in length. Fragments of IRS-2 can be generated by methods known to those skilled in the art. The ability of a candidate fragment to exhibit a biological activity of IRS-2 can be assessed by methods known to those skilled in the art as described herein. Also included are IRS-2's containing residues that are not required for biological activity of the peptide or that result from alternative mRNA splicing or alternative protein processing events.

Nucleic acid encoding all or part of the IRS-2 gene can be used to transform cells. For example, the IRS-2 gene, e.g., a misexpressing or mutant form of it e.g., a deletion, or other DNA encoding an IRS-2 protein or peptide can be used to transform a cell and to produce a cell in which the cell's genomic IRS-2 gene has been replaced by the transformed gene, producing, e.g., a cell deleted for the IRS-2 gene. This approach can be used with cells capable of being grown in culture, e.g., cultured stem cells, to investigate the function of the gene.

Analogously, nucleic acid encoding all or part of the IRS-2 gene, e.g., a misexpressing or mutant form of the gene, e.g., a deletion, can be used to transform a cell which subsequently gives rise to a transgenic animal, e.g. a transgenic mouse. This approach can be used to create, e.g., a transgenic animal in which the IRS-2 gene is, e.g., inactivated, e.g., by a deletion. Homozygous transgenic animals can be made by crosses between the offspring of a founder transgenic animal. Cell or tissue cultures can be derived from a transgenic animal.

In order to obtain an IRS-2 polypeptide, IRS-2-encoding DNA is introduced into an expression vector, the vector introduced into a cell suitable for expression of the desired protein, and the peptide recovered and purified, by prior art methods. Antibodies to the peptides an proteins can be made by immunizing an animal, e.g., a rabbit or mouse, and recovering anti-IRS-2 antibodies by prior art methods.

Fragments of IRS-2 can be made by expressing IRS-2 DNA which has been manipulated in vitro to encode the desired fragment; e.g., by restriction digestion of the DNA sequence of SEQ ID NO:1. Analogs can be made, e.g., by in vitro DNA sequence modifications of the sequence of SEQ ID NO:1. For example, in vitro mutagenesis can be used to convert the DNA sequence of SEQ ID NO:1 into a sequence which encodes an analog in which one or more amino acid residues has undergone a replacement, e.g., a conservative replacement as described in Table 3. Fragments or analogs can be tested by methods known to those skilled in the art for the presence of IRS-2 activity.

The invention also provides for the generation of IRS-2 mimetics, e.g. peptides or non-peptide agents, which are able to modulate, e.g., inhibit, binding of an IRS-2 to another protein. Various forms of mutagenesis are generally applicable for mapping the determinants of the IRS-2 which participate in protein-protein interactions involved in binding to a second protein. For example, homologs of IRS-2 (both agonist and antagonist forms) can be generated and screened using, for example, alanine scanning mutagenesis and the like (Ruf et al. (1994) Biochemistry 33:1565–1572; Wang et al. (1994) J Biol Chem 269:3095–3099; Balint et al. (1993) Gene 137:109–118; Grodberg et al. (1993) Eur J Biochem 218:597–601; Nagashima et al. (1993) J Biol Chem 268:2888–2892; Lowman et al. (1991) Biochemistry 30:10832–10838; and Cunningham et al. (1989) Science 244:1081–1085), by linker scanning mutagenesis (Gustin et al. (1993) Virology 193:653–660; Brown et al. (1992) Mol Cell Biol 12:2644–2652; McKnight et al. (1982) Science 232:316); or by saturation mutagenesis (Meyers et al. (1986) Science 232:613).

The critical residues of peptides of the invention which are involved in molecular recognition of, can be determined and used to generate peptidomimetics which competitively inhibit binding of IRS-2 with other proteins (see, for example, "Peptide inhibitors of human papillomavirus protein binding to retinoblastoma gene protein" European patent applications EP-412,7624 and EP-531,080A). By using, for example, scanning mutagenesis to map the residues of IRS-2 involved in its binding to the another protein, peptidomimetic compounds can be generated which mimic those residues of IRS-2 ascertained to be involved in binding to the other protein, and which therefore can be used to inhibit binding of the authentic IRS-2 protein to the protein. For instance, non-hydrolyzable peptide analogs of such residues can be generated using benzodiazepine (e.g., see Freidinger et al. in Peptides: Chemistry and Biology, G. R. Marshall ed., ESCOM Publisher: Leiden, Netherlands, 1988), azepine (e.g., see Huffman et al. in Peptides: Chemistry and Biology, G. R. Marshall ed., ESCOM Publisher: Leiden, Netherlands, 1988), substituted gama lactam rings (Garvey et al. in Peptides: Chemistry and Biology, G. R. Marshall ed., ESCOM Publisher: Leiden, Netherlands, 1988), keto-methylene pseudopeptides (Ewenson et al. (1986) J Med Chem 29:295; and Ewenson et al. in Peptides: Structure and Function (Proceedings of the 9th American Peptide Symposium) Pierce Chemical Co. Rockland, Ill., 1985), β-turn dipeptide cores (Nagai et al. (1985) Tetrahedron Lett 26:647; and Sato et al. (1986) J Chem Soc Perkin Trans 1:1231), and β-aminoalcohols (Gordon et al. (1985) Biochem Biophys Res Commun 126:419; and Dann et al. (1986) Biochem Biophys Res Commun 134:71).

Other embodiments are within the following claims.

What is claimed is:

1. A substantially pure nucleic acid which encodes an Insulin Receptor Substrate-2 (IRS-2) polypeptide, wherein said polypeptide has the sequence of SEQ ID NO:64.

2. The substantially pure nucleic acid of claim 1, wherein said polypeptide has one or more of the following activities:
   (1) it is capable of binding to the insulin receptor;
   (2) it is capable of binding to the IL-4 receptor complex;
   (3) it is capable of binding to the IL-13 receptor complex;
   (4) it is capable of binding to the IL-15 receptor complex;
   (5) it is capable of association with SH2 domains of Grb-2, SH-PTP-2, nck, or c-fyn;
   (6) it is capable of association with PI 3'-kinase; and
   (7) it is capable of being phosphorylated by the insulin receptor.

3. A substantially pure nucleic acid which encodes an Insulin Receptor Substrate-2 (IRS-2) polypeptide, comprising the sequence of SEQ ID NO:1.

4. A vector comprising a nucleic acid which encodes an IRS-2 polypeptide of claim 1, 2, or 3.

5. A host cell transfected with a vector comprising a nucleic acid which encodes an IRS-2 polypeptide of claim 1, 2, or 3.

6. A method of producing a recombinant IRS-2 polypeptide comprising culturing a host cell transfected with a vector comprising a nucleic acid which encodes an IRS-2 polypeptide of claim 1, 2, or 3 in a cell culture medium and isolating said IRS-2 polypeptide from said cell or said cell culture medium.

\* \* \* \* \*

UNITED STATES PATENT AND TRADEMARK OFFICE
CERTIFICATE OF CORRECTION

PATENT NO. : 5,858,701
DATED : January 12, 1999
INVENTOR(S) : Jacalyn H. Pierce and Xiao Jian Sun It is certified that error appears in the above-identified patent and that said Letters Patent is hereby corrected as shown below:

Column 1,
Line 4, replace with the following rewritten paragraph:

-- STATEMENT REGARDING FEDERALLY SPONSORED RESEARCH
This invention was made with support from the U.S. government under grant number DK 33201 awarded by the National Institutes of Health. The government has certain rights in the invention. --.

Signed and Sealed this

Eighteenth Day of February, 2003

JAMES E. ROGAN
*Director of the United States Patent and Trademark Office*

SEQUENCE LISTING ( 1 ) GENERAL INFORMATION:

( i i i ) NUMBER OF SEQUENCES: 64

( 2 ) INFORMATION FOR SEQ ID NO:1:

( i ) SEQUENCE CHARACTERISTICS:
( A ) LENGTH: 4088 base pairs
( B ) TYPE: nucleic acid
( C ) STRANDEDNESS: single
( D ) TOPOLOGY: linear ( i i ) MOLECULE TYPE: cDNA ( i x ) FEATURE:
( A ) NAME/KEY: CDS
( B ) LOCATION: 60..4022

( x i ) SEQUENCE DESCRIPTION: SEQ ID NO:1:

```
CCCCTCGGCC   CTCGCCATCC   CCTGTTCGCA   GCCGGGCAGA   GAGACCTGAA   GCGGCGGCG                              59

ATG   GCT   AGC   GCG   CCC   CTG   CCT   GGG   CCC   CCC   GCG   TCG   GGG   GGC   GGG   GAG         107
Met   Ala   Ser   Ala   Pro   Leu   Pro   Gly   Pro   Pro   Ala   Ser   Gly   Gly   Gly   Glu
 1                      5                       10                      15

GGC   CCG   AAC   CTC   AAT   AAC   AAC   AAC   AAC   AAC   AAC   CAC   AGC   GTG   CGC               155
Gly   Pro   Asn   Leu   Asn   Asn   Asn   Asn   Asn   Asn   Asn   His   Ser   Val   Arg
                  20                            25                      30

AAG   TGC   GGC   TAC   CTG   CGC   AAG   CAG   AAG   CAC   GGC   CAC   AAG   CGC   TTT   TTC         203
Lys   Cys   Gly   Tyr   Leu   Arg   Lys   Gln   Lys   His   Gly   His   Lys   Arg   Phe   Phe
            35                            40                            45

GTG   TTG   CGC   GGG   CCC   GGC   ACG   GGC   GGC   GAC   GAG   GCA   TCC   GCG   GCT   GGG         251
Val   Leu   Arg   Gly   Pro   Gly   Thr   Gly   Gly   Asp   Glu   Ala   Ser   Ala   Ala   Gly
      50                            55                            60

GGG   TCG   CCG   CCG   CAG   CCT   CCG   CGG   CTG   GAG   TAC   TAC   GAG   AGC   GAG   AAG         299
Gly   Ser   Pro   Pro   Gln   Pro   Pro   Arg   Leu   Glu   Tyr   Tyr   Glu   Ser   Glu   Lys
65                      70                            75                            80

AAG   TGG   AGG   AGC   AAG   GCG   GGC   GCG   CCG   AAG   CGA   GTG   ATC   GCG   CTC   GAC         347
Lys   Trp   Arg   Ser   Lys   Ala   Gly   Ala   Pro   Lys   Arg   Val   Ile   Ala   Leu   Asp
                  85                            90                            95

TGC   TGT   CTG   AAC   ATC   AAC   AAG   CGC   GCG   GAC   GCC   AAG   CAC   AAG   TAC   CTG         395
Cys   Cys   Leu   Asn   Ile   Asn   Lys   Arg   Ala   Asp   Ala   Lys   His   Lys   Tyr   Leu
                  100                           105                           110

ATC   GCC   CTC   TAC   ACC   AAG   GAC   GAG   TAC   TTC   GCT   GTA   GCG   GCG   GAG   AAC         443
Ile   Ala   Leu   Tyr   Thr   Lys   Asp   Glu   Tyr   Phe   Ala   Val   Ala   Ala   Glu   Asn
            115                           120                           125

GAG   CAG   GAG   CAG   GAG   GGC   TGG   TAC   CGC   GCA   CTC   ACC   GAC   TTG   GTC   AGC         491
Glu   Gln   Glu   Gln   Glu   Gly   Trp   Tyr   Arg   Ala   Leu   Thr   Asp   Leu   Val   Ser
      130                           135                           140

GAA   GGC   CGC   TCT   GGC   GAG   GGG   GGC   TCG   GGC   ACC   ACC   GGA   GGC   TCT   TGC         539
Glu   Gly   Arg   Ser   Gly   Glu   Gly   Gly   Ser   Gly   Thr   Thr   Gly   Gly   Ser   Cys
145                     150                           155                           160

AGC   GCC   TCT   CTC   CCG   GGC   GTC   CTG   GGC   GGC   TCA   GCG   GGC   GCC   GCT   GGC         587
Ser   Ala   Ser   Leu   Pro   Gly   Val   Leu   Gly   Gly   Ser   Ala   Gly   Ala   Ala   Gly
                  165                           170                           175

TGC   GAT   GAC   AAC   TAC   GGG   CTC   GTG   ACA   CCC   GCC   ACG   GCC   GTC   TAC   CGC         635
Cys   Asp   Asp   Asn   Tyr   Gly   Leu   Val   Thr   Pro   Ala   Thr   Ala   Val   Tyr   Arg
                  180                           185                           190

GAG   GTG   TGG   CAG   GTG   AAC   CTG   AAA   CCT   AAG   GGA   CTG   GGC   CAG   AGC   AAG         683
Glu   Val   Trp   Gln   Val   Asn   Leu   Lys   Pro   Lys   Gly   Leu   Gly   Gln   Ser   Lys
            195                           200                           205

AAC   CTG   ACT   GGT   GTA   TAC   CGC   CTA   TGC   CTG   TCT   GCG   CGC   ACC   ATC   GGC         731
Asn   Leu   Thr   Gly   Val   Tyr   Arg   Leu   Cys   Leu   Ser   Ala   Arg   Thr   Ile   Gly
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     | 210 |     |     |     | 215 |     |     |     |     |     | 220 |     |     |     |     |      |
| TTC | GTG | AAG | CTC | AAT | TGC | GAA | CAG | CCG | TCG | GTG | ACG | CTG | CAG | CTT | ATG | 779  |
| Phe | Val | Lys | Leu | Asn | Cys | Glu | Gln | Pro | Ser | Val | Thr | Leu | Gln | Leu | Met |      |
| 225 |     |     |     | 230 |     |     |     |     | 235 |     |     |     |     |     | 240 |      |
| AAC | ATT | CGC | CGC | TGC | GGC | CAC | TCG | GAC | AGC | TTC | TTC | TTC | ATC | GAG | GTG | 827  |
| Asn | Ile | Arg | Arg | Cys | Gly | His | Ser | Asp | Ser | Phe | Phe | Phe | Ile | Glu | Val |      |
|     |     |     |     | 245 |     |     |     |     | 250 |     |     |     |     | 255 |     |      |
| GGC | CGT | TCG | GCG | GTC | ACC | GGT | CCC | GGG | GAG | CTG | TGG | ATG | CAA | GCC | GAC | 875  |
| Gly | Arg | Ser | Ala | Val | Thr | Gly | Pro | Gly | Glu | Leu | Trp | Met | Gln | Ala | Asp |      |
|     |     |     | 260 |     |     |     |     | 265 |     |     |     |     | 270 |     |     |      |
| GAC | TCG | GTG | GTG | GCG | CAG | AAC | ATC | CAT | GAG | ACC | ATC | CTA | GAA | GCT | ATG | 923  |
| Asp | Ser | Val | Val | Ala | Gln | Asn | Ile | His | Glu | Thr | Ile | Leu | Glu | Ala | Met |      |
|     |     | 275 |     |     |     |     | 280 |     |     |     |     | 285 |     |     |     |      |
| AAG | GCA | CTC | AAA | GAG | CTC | TTC | GAG | TTC | CGG | CCT | CGC | AGC | AAG | AGT | CAG | 971  |
| Lys | Ala | Leu | Lys | Glu | Leu | Phe | Glu | Phe | Arg | Pro | Arg | Ser | Lys | Ser | Gln |      |
|     | 290 |     |     |     |     | 295 |     |     |     |     | 300 |     |     |     |     |      |
| TCG | TCC | GGG | TCG | TCA | GCC | ACG | CAT | CCC | ATC | AGC | GTG | CCG | GGC | GCG | CGC | 1019 |
| Ser | Ser | Gly | Ser | Ser | Ala | Thr | His | Pro | Ile | Ser | Val | Pro | Gly | Ala | Arg |      |
| 305 |     |     |     |     | 310 |     |     |     |     | 315 |     |     |     |     | 320 |      |
| CGC | CAC | CAC | CAC | CTA | GTC | AAC | CTA | CCC | CCT | AGC | CAG | ACC | GGC | CTG | GTG | 1067 |
| Arg | His | His | His | Leu | Val | Asn | Leu | Pro | Pro | Ser | Gln | Thr | Gly | Leu | Val |      |
|     |     |     |     | 325 |     |     |     |     | 330 |     |     |     |     | 335 |     |      |
| CGC | CGC | TCG | CGC | ACT | GAC | AGC | CTG | GCG | GCC | ACC | CCC | CCA | GCA | GCC | AAG | 1115 |
| Arg | Arg | Ser | Arg | Thr | Asp | Ser | Leu | Ala | Ala | Thr | Pro | Pro | Ala | Ala | Lys |      |
|     |     |     | 340 |     |     |     |     | 345 |     |     |     |     | 350 |     |     |      |
| TGC | ACT | TCG | TGC | CGG | GTT | CGT | ACG | GCC | AGC | GAG | GGC | GAC | GGC | GGC | GCG | 1163 |
| Cys | Thr | Ser | Cys | Arg | Val | Arg | Thr | Ala | Ser | Glu | Gly | Asp | Gly | Gly | Ala |      |
|     |     | 355 |     |     |     |     | 360 |     |     |     |     | 365 |     |     |     |      |
| GCA | GGC | GGG | GCC | GGG | ACG | GCA | GGA | GGC | AGG | CCG | ATG | TCG | GTG | GCA | GGG | 1211 |
| Ala | Gly | Gly | Ala | Gly | Thr | Ala | Gly | Gly | Arg | Pro | Met | Ser | Val | Ala | Gly |      |
|     | 370 |     |     |     |     | 375 |     |     |     |     | 380 |     |     |     |     |      |
| AGC | CCC | CTG | AGT | CCC | GGG | CCG | GTG | CGC | GCG | CCC | CTT | AGC | CGC | TCG | CAC | 1259 |
| Ser | Pro | Leu | Ser | Pro | Gly | Pro | Val | Arg | Ala | Pro | Leu | Ser | Arg | Ser | His |      |
| 385 |     |     |     |     | 390 |     |     |     |     | 395 |     |     |     |     | 400 |      |
| ACC | CTG | AGC | GCC | GGC | TGC | GGA | GGC | CGC | CCG | AGC | AAA | GTG | ACT | CTG | GCG | 1307 |
| Thr | Leu | Ser | Ala | Gly | Cys | Gly | Gly | Arg | Pro | Ser | Lys | Val | Thr | Leu | Ala |      |
|     |     |     |     | 405 |     |     |     |     | 410 |     |     |     |     | 415 |     |      |
| CCG | GCA | GGG | GGA | GCC | CTG | CAA | CAC | AGC | CGC | TCC | ATG | TCC | ATG | CCC | GTG | 1355 |
| Pro | Ala | Gly | Gly | Ala | Leu | Gln | His | Ser | Arg | Ser | Met | Ser | Met | Pro | Val |      |
|     |     |     | 420 |     |     |     |     | 425 |     |     |     |     | 430 |     |     |      |
| GCG | CAC | TCA | CCT | CCT | GCA | GCC | ACC | AGC | CCA | GGC | AGC | CTG | TCC | TCC | AGC | 1403 |
| Ala | His | Ser | Pro | Pro | Ala | Ala | Thr | Ser | Pro | Gly | Ser | Leu | Ser | Ser | Ser |      |
|     |     | 435 |     |     |     |     | 440 |     |     |     |     | 445 |     |     |     |      |
| AGT | GGG | CAC | GGC | TCG | GGC | TCC | TAC | CCG | CTG | CCA | CCT | GGC | TCC | CAC | CCG | 1451 |
| Ser | Gly | His | Gly | Ser | Gly | Ser | Tyr | Pro | Leu | Pro | Pro | Gly | Ser | His | Pro |      |
|     | 450 |     |     |     |     | 455 |     |     |     |     | 460 |     |     |     |     |      |
| CAC | CTG | CCT | CAT | CCA | CTG | CAT | CAC | CCC | CAA | GGC | CAG | CGT | CCG | TCC | AGC | 1499 |
| His | Leu | Pro | His | Pro | Leu | His | His | Pro | Gln | Gly | Gln | Arg | Pro | Ser | Ser |      |
| 465 |     |     |     |     | 470 |     |     |     |     | 475 |     |     |     |     | 480 |      |
| GGT | AGT | GCC | TCC | GCC | TCG | GGC | TCC | CCC | AGC | GAC | CCG | GGT | TTC | ATG | TCC | 1547 |
| Gly | Ser | Ala | Ser | Ala | Ser | Gly | Ser | Pro | Ser | Asp | Pro | Gly | Phe | Met | Ser |      |
|     |     |     |     | 485 |     |     |     |     | 490 |     |     |     |     | 495 |     |      |
| CTT | GAC | GAG | TAT | GGC | TCC | AGC | CCT | GGC | GAC | CTG | AGA | GCC | TTC | AGT | AGC | 1595 |
| Leu | Asp | Glu | Tyr | Gly | Ser | Ser | Pro | Gly | Asp | Leu | Arg | Ala | Phe | Ser | Ser |      |
|     |     |     | 500 |     |     |     |     | 505 |     |     |     |     | 510 |     |     |      |
| CAC | AGG | AGC | AAC | ACA | CCC | GAG | TCA | ATA | GCG | GAG | ACC | CCG | CCA | GCC | AGA | 1643 |
| His | Arg | Ser | Asn | Thr | Pro | Glu | Ser | Ile | Ala | Glu | Thr | Pro | Pro | Ala | Arg |      |
|     |     | 515 |     |     |     |     | 520 |     |     |     |     | 525 |     |     |     |      |
| GAT | GGC | AGT | GGG | GGC | GAA | CTC | TAT | GGG | TAC | ATG | AGC | ATG | GAT | AGA | CCC | 1691 |
| Asp | Gly | Ser | Gly | Gly | Glu | Leu | Tyr | Gly | Tyr | Met | Ser | Met | Asp | Arg | Pro |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     | 530 |     |     |     |     | 535 |     |     |     |     | 540 |     |     |     |      |
| CTG | AGC | CAC | TGT | GGC | CGC | CCT | TAC | CGT | AGG | GTC | TCA | GGG | GAT | GGG | GCC | 1739 |
| Leu | Ser | His | Cys | Gly | Arg | Pro | Tyr | Arg | Arg | Val | Ser | Gly | Asp | Gly | Ala |      |
| 545 |     |     |     | 550 |     |     |     |     | 555 |     |     |     |     | 560 |     |      |
| CAG | GAC | CTG | GAT | AGA | GGA | CTG | AGG | AAG | AGG | ACT | TAT | TCC | CTA | ACC | ACG | 1787 |
| Gln | Asp | Leu | Asp | Arg | Gly | Leu | Arg | Lys | Arg | Thr | Tyr | Ser | Leu | Thr | Thr |      |
|     |     |     |     | 565 |     |     |     |     | 570 |     |     |     |     | 575 |     |      |
| CCT | GCC | AGG | CAG | CGG | CAG | GTA | CCT | CAG | CCT | TCC | TCT | GCC | TCT | CTA | GAT | 1835 |
| Pro | Ala | Arg | Gln | Arg | Gln | Val | Pro | Gln | Pro | Ser | Ser | Ala | Ser | Leu | Asp |      |
|     |     |     | 580 |     |     |     |     | 585 |     |     |     |     | 590 |     |     |      |
| GAA | TAC | ACT | CTC | ATG | AGG | GCC | ACC | TTC | TCT | GGT | AGT | TCA | GGT | CGC | CTC | 1883 |
| Glu | Tyr | Thr | Leu | Met | Arg | Ala | Thr | Phe | Ser | Gly | Ser | Ser | Gly | Arg | Leu |      |
|     |     | 595 |     |     |     |     | 600 |     |     |     |     | 605 |     |     |     |      |
| TGC | CCA | TCC | TTC | CCT | GCG | TCC | TCT | CCC | AAA | GTG | GCC | TAC | AAC | CCT | TAC | 1931 |
| Cys | Pro | Ser | Phe | Pro | Ala | Ser | Ser | Pro | Lys | Val | Ala | Tyr | Asn | Pro | Tyr |      |
|     | 610 |     |     |     |     | 615 |     |     |     |     | 620 |     |     |     |     |      |
| CCA | GAG | GAC | TAT | GGA | GAC | ATT | GAG | ATT | GGT | TCT | CAC | AAG | AGT | TCC | AGC | 1979 |
| Pro | Glu | Asp | Tyr | Gly | Asp | Ile | Glu | Ile | Gly | Ser | His | Lys | Ser | Ser | Ser |      |
| 625 |     |     |     | 630 |     |     |     |     | 635 |     |     |     |     | 640 |     |      |
| AGT | AAC | CTG | GGG | GCA | GAT | GAT | GGC | TAC | ATG | CCC | ATG | ACC | CCT | GGG | GCA | 2027 |
| Ser | Asn | Leu | Gly | Ala | Asp | Asp | Gly | Tyr | Met | Pro | Met | Thr | Pro | Gly | Ala |      |
|     |     |     |     | 645 |     |     |     |     | 650 |     |     |     |     | 655 |     |      |
| GCC | CTT | AGG | AGT | GGT | GGT | CCC | AAT | AGC | TGC | AAG | AGC | GAT | GAC | TAC | ATG | 2075 |
| Ala | Leu | Arg | Ser | Gly | Gly | Pro | Asn | Ser | Cys | Lys | Ser | Asp | Asp | Tyr | Met |      |
|     |     |     | 660 |     |     |     |     | 665 |     |     |     |     | 670 |     |     |      |
| CCC | ATG | AGC | CCC | ACA | AGC | GTG | TCT | GCT | CCC | AAG | CAG | ATC | CTG | CAG | CCA | 2123 |
| Pro | Met | Ser | Pro | Thr | Ser | Val | Ser | Ala | Pro | Lys | Gln | Ile | Leu | Gln | Pro |      |
|     |     | 675 |     |     |     |     | 680 |     |     |     |     | 685 |     |     |     |      |
| CGC | TTG | GCA | GCG | GCC | TTG | CCC | CCT | TCC | GGA | GCA | GCC | GTG | CCA | GCA | CCC | 2171 |
| Arg | Leu | Ala | Ala | Ala | Leu | Pro | Pro | Ser | Gly | Ala | Ala | Val | Pro | Ala | Pro |      |
|     | 690 |     |     |     |     | 695 |     |     |     |     | 700 |     |     |     |     |      |
| CCT | TCA | GGG | GTG | GGC | AGG | ACC | TTC | CCA | GTA | AAC | GGA | GGT | GGC | TAC | AAA | 2219 |
| Pro | Ser | Gly | Val | Gly | Arg | Thr | Phe | Pro | Val | Asn | Gly | Gly | Gly | Tyr | Lys |      |
| 705 |     |     |     | 710 |     |     |     |     | 715 |     |     |     |     | 720 |     |      |
| GCC | AGC | TCC | CCA | GCG | GAG | AGC | TCC | CCA | GAA | GAC | AGT | GGG | TAC | ATG | CGA | 2267 |
| Ala | Ser | Ser | Pro | Ala | Glu | Ser | Ser | Pro | Glu | Asp | Ser | Gly | Tyr | Met | Arg |      |
|     |     |     |     | 725 |     |     |     |     | 730 |     |     |     |     | 735 |     |      |
| ATG | TGG | TGT | GGC | TCC | AAG | CTG | TCT | ATG | GAG | AAC | CCA | GAC | CCT | AAG | CTA | 2315 |
| Met | Trp | Cys | Gly | Ser | Lys | Leu | Ser | Met | Glu | Asn | Pro | Asp | Pro | Lys | Leu |      |
|     |     |     | 740 |     |     |     |     | 745 |     |     |     |     | 750 |     |     |      |
| CTC | CCC | AAC | GGG | GAC | TAC | CTC | AAC | ATG | TCC | CCC | AGC | GAG | GCA | GGC | ACT | 2363 |
| Leu | Pro | Asn | Gly | Asp | Tyr | Leu | Asn | Met | Ser | Pro | Ser | Glu | Ala | Gly | Thr |      |
|     |     | 755 |     |     |     |     | 760 |     |     |     |     | 765 |     |     |     |      |
| GCA | GGG | ACC | CCA | CCT | GAC | TTC | TCA | GCA | GCT | TTG | CGT | GGA | GGC | AGT | GAA | 2411 |
| Ala | Gly | Thr | Pro | Pro | Asp | Phe | Ser | Ala | Ala | Leu | Arg | Gly | Gly | Ser | Glu |      |
|     | 770 |     |     |     |     | 775 |     |     |     |     | 780 |     |     |     |     |      |
| GGC | CTC | AAA | GGC | ATC | CCG | GGC | CAC | TGC | TAC | AGC | TCT | TTG | CCC | CGC | TCT | 2459 |
| Gly | Leu | Lys | Gly | Ile | Pro | Gly | His | Cys | Tyr | Ser | Ser | Leu | Pro | Arg | Ser |      |
| 785 |     |     |     | 790 |     |     |     |     | 795 |     |     |     |     | 800 |     |      |
| TAT | AAG | GCT | CCC | TGT | TCC | TGC | AGC | GGA | GAC | AAT | GAC | CAG | TAT | GTG | CTC | 2507 |
| Tyr | Lys | Ala | Pro | Cys | Ser | Cys | Ser | Gly | Asp | Asn | Asp | Gln | Tyr | Val | Leu |      |
|     |     |     |     | 805 |     |     |     |     | 810 |     |     |     |     | 815 |     |      |
| ATG | AGC | TCC | CCT | GTG | GGC | CGG | ATC | TTG | GAA | GAG | GAG | AGA | CTG | GAG | CCC | 2555 |
| Met | Ser | Ser | Pro | Val | Gly | Arg | Ile | Leu | Glu | Glu | Glu | Arg | Leu | Glu | Pro |      |
|     |     |     | 820 |     |     |     |     | 825 |     |     |     |     | 830 |     |     |      |
| CAG | GCC | ACC | CCA | GGG | GCT | GGC | ACC | TTT | GGG | GCA | GCT | GGT | GGT | AGT | CAT | 2603 |
| Gln | Ala | Thr | Pro | Gly | Ala | Gly | Thr | Phe | Gly | Ala | Ala | Gly | Gly | Ser | His |      |
|     |     | 835 |     |     |     |     | 840 |     |     |     |     | 845 |     |     |     |      |
| ACC | CAG | CCT | CAT | CAC | TCA | GCA | GTG | CCT | TCC | TCC | ATG | AGG | CCG | AGT | GCC | 2651 |
| Thr | Gln | Pro | His | His | Ser | Ala | Val | Pro | Ser | Ser | Met | Arg | Pro | Ser | Ala |      |

|     |     |     |     |     | 850 |     |     |     |     | 855 |     |     |     |     | 860 |      |
|-----|-----|-----|-----|-----|-----|-----|-----|-----|-----|-----|-----|-----|-----|-----|-----|------|
| ATC | GGT | GGC | CGC | CCT | GAG | GGC | TTC | CTG | GGC | CAG | CGA | TGT | CGG | GCA | GTG | 2699 |
| Ile | Gly | Gly | Arg | Pro | Glu | Gly | Phe | Leu | Gly | Gln | Arg | Cys | Arg | Ala | Val |      |
| 865 |     |     |     |     | 870 |     |     |     |     | 875 |     |     |     |     | 880 |      |
| CGG | CCT | ACA | CGC | CTA | TCG | CTA | GAG | GGA | CTG | CAG | ACC | CTT | CCC | AGC | ATG | 2747 |
| Arg | Pro | Thr | Arg | Leu | Ser | Leu | Glu | Gly | Leu | Gln | Thr | Leu | Pro | Ser | Met |      |
|     |     |     |     |     | 885 |     |     |     |     | 890 |     |     |     |     | 895 |      |
| CAA | GAG | TAC | CCT | CTA | CCC | ACA | GAG | CCC | AAG | AGC | CCT | GGC | GAG | TAC | ATC | 2795 |
| Gln | Glu | Tyr | Pro | Leu | Pro | Thr | Glu | Pro | Lys | Ser | Pro | Gly | Glu | Tyr | Ile |      |
|     |     |     |     | 900 |     |     |     |     | 905 |     |     |     |     | 910 |     |      |
| AAC | ATT | GAC | TTT | GGT | GAG | GCA | GGT | ACC | CGT | CTG | TCT | CCG | CCT | GCC | CCC | 2843 |
| Asn | Ile | Asp | Phe | Gly | Glu | Ala | Gly | Thr | Arg | Leu | Ser | Pro | Pro | Ala | Pro |      |
|     |     |     |     | 915 |     |     |     |     | 920 |     |     |     |     | 925 |     |      |
| CCA | CTA | CTG | GCA | TCC | GCG | GCC | TCA | TCT | TCT | TCA | CTG | CTC | TCA | GCT | AGT | 2891 |
| Pro | Leu | Leu | Ala | Ser | Ala | Ala | Ser | Ser | Ser | Ser | Leu | Leu | Ser | Ala | Ser |      |
|     |     | 930 |     |     |     |     | 935 |     |     |     |     | 940 |     |     |     |      |
| AGT | CCT | GCT | TCA | TCC | CTG | GGT | TCA | GGA | ACC | CCA | GGC | ACC | AGC | AGC | GAC | 2939 |
| Ser | Pro | Ala | Ser | Ser | Leu | Gly | Ser | Gly | Thr | Pro | Gly | Thr | Ser | Ser | Asp |      |
| 945 |     |     |     |     | 950 |     |     |     |     | 955 |     |     |     |     | 960 |      |
| AGC | CGG | CAG | CGC | TCT | CCA | CTC | TCT | GAC | TAT | ATG | AAC | CTG | GAC | TTC | AGT | 2987 |
| Ser | Arg | Gln | Arg | Ser | Pro | Leu | Ser | Asp | Tyr | Met | Asn | Leu | Asp | Phe | Ser |      |
|     |     |     |     | 965 |     |     |     |     | 970 |     |     |     |     | 975 |     |      |
| TCT | CCC | AAG | TCC | CCC | AAG | CCT | AGC | ACC | CGC | AGT | GGG | GAC | ACA | GTA | GGC | 3035 |
| Ser | Pro | Lys | Ser | Pro | Lys | Pro | Ser | Thr | Arg | Ser | Gly | Asp | Thr | Val | Gly |      |
|     |     |     | 980 |     |     |     |     | 985 |     |     |     |     | 990 |     |     |      |
| TCC | ATG | GAT | GGC | CTT | CTC | TCT | CCA | GAG | GCT | TCA | TCC | CCA | TAC | CCA | CCA | 3083 |
| Ser | Met | Asp | Gly | Leu | Leu | Ser | Pro | Glu | Ala | Ser | Ser | Pro | Tyr | Pro | Pro |      |
|     |     |     | 995 |     |     |     |     | 1000|     |     |     |     | 1005|     |     |      |
| CTG | CCC | CCA | CGT | CCT | TCC | ACT | TCC | CCT | TCC | TCC | TTA | CAG | CAG | CCT | CTG | 3131 |
| Leu | Pro | Pro | Arg | Pro | Ser | Thr | Ser | Pro | Ser | Ser | Leu | Gln | Gln | Pro | Leu |      |
|     |     | 1010|     |     |     |     | 1015|     |     |     |     | 1020|     |     |     |      |
| CCA | CCT | GCC | CCG | GGA | GAC | CTA | TAC | CGC | CTG | CCT | CCA | GCA | TCA | GCT | GCC | 3179 |
| Pro | Pro | Ala | Pro | Gly | Asp | Leu | Tyr | Arg | Leu | Pro | Pro | Ala | Ser | Ala | Ala |      |
| 1025|     |     |     |     | 1030|     |     |     |     | 1035|     |     |     |     | 1040|      |
| ACT | TCC | CAG | GGT | CCC | ACT | GCT | GGC | TCC | TCA | ATG | TCC | TCC | GAG | CCT | GGG | 3227 |
| Thr | Ser | Gln | Gly | Pro | Thr | Ala | Gly | Ser | Ser | Met | Ser | Ser | Glu | Pro | Gly |      |
|     |     |     |     | 1045|     |     |     |     | 1050|     |     |     |     | 1055|     |      |
| GAT | AAT | GGT | GAC | TAT | ACC | GAG | ATG | GCC | TTT | GGT | GTG | GCT | GCA | ACC | CCG | 3275 |
| Asp | Asn | Gly | Asp | Tyr | Thr | Glu | Met | Ala | Phe | Gly | Val | Ala | Ala | Thr | Pro |      |
|     |     |     | 1060|     |     |     |     | 1065|     |     |     |     | 1070|     |     |      |
| CCA | CAA | CCT | ATC | GTG | GCA | CCT | CCA | AAG | CCA | GAA | GGT | GCC | CGA | GTG | GCC | 3323 |
| Pro | Gln | Pro | Ile | Val | Ala | Pro | Pro | Lys | Pro | Glu | Gly | Ala | Arg | Val | Ala |      |
|     |     |     | 1075|     |     |     |     | 1080|     |     |     |     | 1085|     |     |      |
| AGT | CCC | ACA | TCG | GGC | TTG | AAG | CGG | CTA | AGT | CTC | ATG | GAT | CAG | GTA | TCT | 3371 |
| Ser | Pro | Thr | Ser | Gly | Leu | Lys | Arg | Leu | Ser | Leu | Met | Asp | Gln | Val | Ser |      |
|     |     | 1090|     |     |     |     | 1095|     |     |     |     | 1100|     |     |     |      |
| GGG | GTG | GAG | GCT | TTC | CTT | CAA | GTC | AGC | CAG | CCC | CCT | GAC | CCC | CAC | CGG | 3419 |
| Gly | Val | Glu | Ala | Phe | Leu | Gln | Val | Ser | Gln | Pro | Pro | Asp | Pro | His | Arg |      |
| 1105|     |     |     |     | 1110|     |     |     |     | 1115|     |     |     |     | 1120|      |
| GGT | GCT | AAG | GTC | ATC | CGT | GCA | GAC | CCA | CAG | GGG | GGA | CGT | CGT | CGC | CAC | 3467 |
| Gly | Ala | Lys | Val | Ile | Arg | Ala | Asp | Pro | Gln | Gly | Gly | Arg | Arg | Arg | His |      |
|     |     |     |     | 1125|     |     |     |     | 1130|     |     |     |     | 1135|     |      |
| AGT | TCA | GAG | ACC | TTT | TCC | TCT | ACC | ACC | ACC | GTC | ACC | CCA | GTG | TCC | CCA | 3515 |
| Ser | Ser | Glu | Thr | Phe | Ser | Ser | Thr | Thr | Thr | Val | Thr | Pro | Val | Ser | Pro |      |
|     |     |     |     | 1140|     |     |     |     | 1145|     |     |     |     | 1150|     |      |
| TCC | TTT | GCC | CAC | AAT | TCC | AAG | CGC | CAC | AAT | TCG | GCC | TCT | GTG | GAA | AAT | 3563 |
| Ser | Phe | Ala | His | Asn | Ser | Lys | Arg | His | Asn | Ser | Ala | Ser | Val | Glu | Asn |      |
|     |     |     |     | 1155|     |     |     |     | 1160|     |     |     |     | 1165|     |      |
| GTC | TCA | CTC | AGG | AAA | AGC | AGT | GAA | GGC | AGC | AGT | ACC | CTG | GGA | GGA | GGT | 3611 |
| Val | Ser | Leu | Arg | Lys | Ser | Ser | Glu | Gly | Ser | Ser | Thr | Leu | Gly | Gly | Gly |      |

```
                  1 1 7 0                              1 1 7 5                                    1 1 8 0

GAT  GAG  CCG  CCC  ACA  TCC  CCA  GGA  CAG  GCA  CAG  CCC  TTG  GTG  GCT  GTG         3 6 5 9
Asp  Glu  Pro  Pro  Thr  Ser  Pro  Gly  Gln  Ala  Gln  Pro  Leu  Val  Ala  Val
1 1 8 5                      1 1 9 0                   1 1 9 5                      1 2 0 0

CCC  CCA  GTG  CCA  CAG  GCT  AGG  CCG  TGG  AAC  CCC  GGT  CAG  CCC  GGA  GCT         3 7 0 7
Pro  Pro  Val  Pro  Gln  Ala  Arg  Pro  Trp  Asn  Pro  Gly  Gln  Pro  Gly  Ala
                         1 2 0 5                   1 2 1 0                         1 2 1 5

TTG  ATT  GGC  TGT  CCT  GGA  GGC  AGC  AGT  TCT  CCC  ATG  CGC  AGA  GAG  ACC         3 7 5 5
Leu  Ile  Gly  Cys  Pro  Gly  Gly  Ser  Ser  Ser  Pro  Met  Arg  Arg  Glu  Thr
               1 2 2 0                        1 2 2 5                      1 2 3 0

TCC  GTG  GGT  TTC  CAG  AAC  GGC  CTC  AAC  TAT  ATC  GCC  ATC  GAT  GTG  AGA         3 8 0 3
Ser  Val  Gly  Phe  Gln  Asn  Gly  Leu  Asn  Tyr  Ile  Ala  Ile  Asp  Val  Arg
          1 2 3 5                        1 2 4 0                    1 2 4 5

GGC  GAG  CAG  GGG  TCC  TTG  GCG  CAG  TCT  CAG  CCG  CAG  CCA  GGA  GAC  AAG         3 8 5 1
Gly  Glu  Gln  Gly  Ser  Leu  Ala  Gln  Ser  Gln  Pro  Gln  Pro  Gly  Asp  Lys
     1 2 5 0                             1 2 5 5                    1 2 6 0

AAC  TCC  TGG  AGC  CGG  ACC  CGT  AGC  CTT  GGG  GGG  CTC  CTC  GGC  ACC  GTC         3 8 9 9
Asn  Ser  Trp  Ser  Arg  Thr  Arg  Ser  Leu  Gly  Gly  Leu  Leu  Gly  Thr  Val
1 2 6 5                        1 2 7 0                   1 2 7 5                      1 2 8 0

GGA  GGC  TCT  GGC  GCC  AGC  GGA  GTG  TGT  GGG  GGT  CCA  GGC  ACT  GGA  GCT         3 9 4 7
Gly  Gly  Ser  Gly  Ala  Ser  Gly  Val  Cys  Gly  Gly  Pro  Gly  Thr  Gly  Ala
                         1 2 8 5                   1 2 9 0                         1 2 9 5

TTG  CCC  TCT  GCC  AGC  ACC  TAT  GCA  AGC  ATC  GAC  TTC  CTG  TCC  CAT  CAC         3 9 9 5
Leu  Pro  Ser  Ala  Ser  Thr  Tyr  Ala  Ser  Ile  Asp  Phe  Leu  Ser  His  His
                    1 3 0 0                        1 3 0 5                    1 3 1 0

TTG  AAG  GAA  GCC  ACA  GTC  GTG  AAA  GAG  TGAAGCGCTA  CCAGCCCCAT                    4 0 4 2
Leu  Lys  Glu  Ala  Thr  Val  Val  Lys  Glu
          1 3 1 5                         1 3 2 0

CGCCGCCATG  TTGAAAAAAA  CAAAAACAAA  AACAAAAAAA  AAAAA                                  4 0 8 8
```

( 2 ) INFORMATION FOR SEQ ID NO:2:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:2:

Tyr  Met  Xaa  Met
     1

( 2 ) INFORMATION FOR SEQ ID NO:3:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:3:

Tyr  Phe  Ile  Asn
     1

( 2 ) INFORMATION FOR SEQ ID NO:4:

( i ) SEQUENCE CHARACTERISTICS:
        ( A ) LENGTH: 19 amino acids
        ( B ) TYPE: amino acid (D) TOPOLOGY: linear (ii) MOLECULE TYPE: peptide (v) FRAGMENT TYPE: internal (xi) SEQUENCE DESCRIPTION: SEQ ID NO:4:

Val Ala Tyr Asn Pro Tyr Pro Glu Asp Tyr Gly Asp Ile Glu Ile Gly
1               5                   10                  15
Ser His Lys (2) INFORMATION FOR SEQ ID NO:5:

(i) SEQUENCE CHARACTERISTICS:
    (A) LENGTH: 16 amino acids
    (B) TYPE: amino acid
    (D) TOPOLOGY: linear (ii) MOLECULE TYPE: peptide (v) FRAGMENT TYPE: internal (xi) SEQUENCE DESCRIPTION: SEQ ID NO:5:

Leu Ser Glu Gly Leu Gln Thr Leu Pro Ser Met Ser Tyr Pro Leu Asn
1               5                   10                  15

(2) INFORMATION FOR SEQ ID NO:6:

(i) SEQUENCE CHARACTERISTICS:
    (A) LENGTH: 19 amino acids
    (B) TYPE: amino acid
    (D) TOPOLOGY: linear (ii) MOLECULE TYPE: peptide (v) FRAGMENT TYPE: internal (xi) SEQUENCE DESCRIPTION: SEQ ID NO:6:

Tyr Gly Phe Ser Asp Pro Leu Thr Phe Asn Ser Val Val Glu Leu Ile
1               5                   10                  15
Asn Tyr Arg (2) INFORMATION FOR SEQ ID NO:7:

(i) SEQUENCE CHARACTERISTICS:
    (A) LENGTH: 17 amino acids
    (B) TYPE: amino acid
    (D) TOPOLOGY: linear (ii) MOLECULE TYPE: peptide (v) FRAGMENT TYPE: internal (xi) SEQUENCE DESCRIPTION: SEQ ID NO:7:

Leu Leu Leu Glu Tyr Leu Glu Glu Lys Tyr Glu Glu His Leu Tyr Glu
1               5                   10                  15
Arg (2) INFORMATION FOR SEQ ID NO:8:

(i) SEQUENCE CHARACTERISTICS:
    (A) LENGTH: 14 amino acids
    (B) TYPE: amino acid
    (D) TOPOLOGY: linear (ii) MOLECULE TYPE: peptide (v) FRAGMENT TYPE: internal ( x i ) SEQUENCE DESCRIPTION: SEQ ID NO:8:

Gly Phe Gln Gln Ile Ser Phe Val Asn Ser Ala Thr Ser Lys
 1               5                  10

( 2 ) INFORMATION FOR SEQ ID NO:9:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:9:

Glu Leu Asp Met Asn Asn Ala Met Gln Ala Glu Ala
 1               5                  10

( 2 ) INFORMATION FOR SEQ ID NO:10:

( i ) SEQUENCE CHARACTERISTICS:
        ( A ) LENGTH: 17 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:10:

Glu Thr Ser Val Gly Phe Gln Asn Gly Leu Asn Tyr Ile Ala Ile Asp
 1               5                  10                      15

Val ( 2 ) INFORMATION FOR SEQ ID NO:11:

( i ) SEQUENCE CHARACTERISTICS:
        ( A ) LENGTH: 13 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:11:

Leu Pro Pro Ala Ser Ala Ala Thr Ser Gln Gly Pro Ala
 1               5                  10

( 2 ) INFORMATION FOR SEQ ID NO:12:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:12:

Ala Leu Thr Asp Leu Val Ser Glu Gly Arg
 1               5                  10

( 2 ) INFORMATION FOR SEQ ID NO:13:

( i ) SEQUENCE CHARACTERISTICS:
        ( A ) LENGTH: 27 base pairs (B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:13:

GTGGCCTACA ACCCARACCC TGAGGAC 27

(2) INFORMATION FOR SEQ ID NO:14:

(i) SEQUENCE CHARACTERISTICS:
(A) LENGTH: 28 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:14:

AATCTCAATG TCGCCATAGT CCTCAGGG 28

(2) INFORMATION FOR SEQ ID NO:15:

(i) SEQUENCE CHARACTERISTICS:
(A) LENGTH: 1234 amino acids
(B) TYPE: amino acid
(D) TOPOLOGY: linear (ii) MOLECULE TYPE: peptide (v) FRAGMENT TYPE: internal (xi) SEQUENCE DESCRIPTION: SEQ ID NO:15:

```
Met Ala Ser Pro Pro Asp Thr Asp Gly Phe Ser Asp Val Arg Lys Val
 1               5                   10                  15
Gly Tyr Leu Arg Lys Pro Lys Ser Met His Lys Arg Phe Phe Val Leu
            20                  25                  30
Arg Ala Ala Ser Glu Ala Gly Gly Pro Ala Arg Leu Glu Tyr Tyr Glu
        35                  40                  45
Asn Glu Lys Lys Trp Arg His Lys Ser Ser Ala Pro Lys Arg Ser Ile
    50                  55                  60
Pro Leu Glu Ser Cys Phe Asn Ile Asn Lys Arg Ala Asp Ser Lys Asn
65                  70                  75                  80
Lys His Leu Val Ala Leu Tyr Thr Arg Asp Glu His Phe Ala Ile Ala
                85                  90                  95
Ala Asp Ser Glu Ala Glu Gln Asp Ser Trp Tyr Gln Ala Leu Leu Gln
            100                 105                 110
Leu His Asn Arg Ala Lys Ala His His Asp Gly Ala Gly Gly Gly Cys
        115                 120                 125
Gly Gly Ser Cys Ser Gly Ser Ser Gly Val Gly Glu Ala Gly Glu Asp
    130                 135                 140
Leu Ser Tyr Asp Thr Gly Pro Gly Pro Ala Phe Lys Glu Val Trp Gln
145                 150                 155                 160
Val Ile Leu Lys Pro Lys Gly Leu Gly Gln Thr Lys Asn Leu Ile Gly
                165                 170                 175
Ile Tyr Arg Leu Cys Leu Thr Ser Lys Thr Ile Ser Phe Val Lys Leu
            180                 185                 190
Asn Ser Glu Ala Ala Ala Val Val Leu Gln Leu Met Asn Ile Arg Arg
        195                 200                 205
Cys Gly His Ser Glu Asn Phe Phe Phe Ile Glu Val Gly Arg Ser Ala
    210                 215                 220
```

```
Val  Thr  Gly  Pro  Gly  Glu  Phe  Trp  Met  Gln  Val  Asp  Asp  Ser  Val  Val
225                 230                      235                           240

Ala  Gln  Asn  Met  His  Glu  Thr  Ile  Leu  Glu  Ala  Met  Arg  Ala  Met  Ser
                    245                      250                      255

Asp  Glu  Phe  Arg  Pro  Arg  Ser  Lys  Ser  Gln  Ser  Ser  Ser  Ser  Cys  Ser
               260                 265                      270

Asn  Pro  Ile  Ser  Val  Pro  Leu  Arg  Arg  His  His  Leu  Asn  Asn  Pro  Pro
          275                      280                      285

Pro  Ser  Gln  Val  Gly  Leu  Thr  Arg  Arg  Ser  Arg  Thr  Glu  Ser  Ile  Thr
     290                      295                      300

Ala  Thr  Ser  Pro  Ala  Ser  Met  Val  Gly  Gly  Lys  Pro  Gly  Ser  Phe  Arg
305                      310                      315                      320

Val  Arg  Ala  Ser  Ser  Asp  Gly  Glu  Gly  Thr  Met  Ser  Arg  Pro  Ala  Ser
               325                      330                      335

Val  Asp  Gly  Ser  Pro  Val  Ser  Pro  Ser  Thr  Asn  Arg  Thr  His  Ala  His
               340                      345                      350

Arg  His  Arg  Gly  Ser  Ser  Arg  Leu  His  Pro  Pro  Leu  Asn  His  Ser  Arg
          355                      360                      365

Ser  Ile  Pro  Met  Pro  Ser  Ser  Arg  Cys  Ser  Pro  Ser  Ala  Thr  Ser  Pro
370                      375                      380

Val  Ser  Leu  Ser  Ser  Ser  Thr  Ser  Gly  His  Gly  Ser  Thr  Ser  Asp
385                      390                      395                      400

Cys  Leu  Phe  Pro  Arg  Arg  Ser  Ser  Ala  Ser  Val  Ser  Gly  Ser  Pro  Ser
               405                      410                      415

Asp  Gly  Gly  Phe  Ile  Ser  Ser  Asp  Glu  Tyr  Gly  Ser  Ser  Pro  Cys  Asp
               420                      425                      430

Phe  Arg  Ser  Ser  Phe  Arg  Ser  Val  Thr  Pro  Asp  Ser  Leu  Gly  His  Thr
          435                      440                      445

Pro  Pro  Ala  Arg  Gly  Glu  Glu  Glu  Leu  Ser  Asn  Tyr  Ile  Cys  Met  Gly
     450                      455                      460

Gly  Lys  Gly  Ala  Ser  Thr  Leu  Ala  Ala  Pro  Asn  Gly  His  Tyr  Ile  Leu
465                      470                      475                      480

Ser  Arg  Gly  Gly  Asn  Gly  His  Arg  Tyr  Ile  Pro  Gly  Ala  Asn  Leu  Gly
                    485                      490                      495

Thr  Ser  Pro  Ala  Leu  Pro  Gly  Asp  Glu  Ala  Ala  Gly  Ala  Ala  Asp  Leu
               500                      505                      510

Asp  Asn  Arg  Phe  Arg  Lys  Arg  Thr  His  Ser  Ala  Gly  Thr  Ser  Pro  Thr
          515                      520                      525

Ile  Ser  His  Gln  Lys  Thr  Pro  Ser  Gln  Ser  Ser  Val  Ala  Ser  Ile  Glu
     530                      535                      540

Glu  Tyr  Thr  Glu  Met  Met  Pro  Ala  Ala  Tyr  Pro  Pro  Gly  Gly  Gly  Ser
545                      550                      555                      560

Gly  Gly  Arg  Leu  Pro  Gly  Tyr  Arg  His  Ser  Ala  Phe  Val  Pro  Thr  His
                    565                      570                      575

Ser  Tyr  Pro  Glu  Glu  Gly  Leu  Glu  Met  His  His  Leu  Glu  Arg  Arg  Gly
               580                      585                      590

Gly  His  His  Arg  Pro  Asp  Thr  Ser  Asn  Leu  His  Thr  Asp  Asp  Gly  Tyr
          595                      600                      605

Met  Pro  Met  Ser  Pro  Gly  Val  Ala  Pro  Val  Pro  Ser  Asn  Arg  Lys  Gly
     610                      615                      620

Asn  Gly  Asp  Tyr  Met  Pro  Met  Ser  Pro  Lys  Ser  Val  Ser  Ala  Pro  Gln
625                      630                      635                      640

Gln  Ile  Ile  Asn  Pro  Ile  Arg  Arg  His  Pro  Gln  Arg  Val  Asp  Pro  Asn
```

-continued

|     |     |     |     | 645 |     |     |     | 650 |     |     |     | 655 |     |     |
|-----|-----|-----|-----|-----|-----|-----|-----|-----|-----|-----|-----|-----|-----|-----|
| Gly | Tyr | Met | Met | Met | Ser | Pro | Ser | Gly | Ser | Cys | Ser | Pro | Asp | Ile | Gly |
|     |     |     | 660 |     |     |     |     | 665 |     |     |     | 670 |     |     |
| Gly | Gly | Ser | Ser | Ser | Ser | Ser | Ile | Ser | Ala | Ala | Pro | Ser | Gly | Ser |
|     |     | 675 |     |     |     |     | 680 |     |     |     | 685 |     |     |
| Ser | Tyr | Gly | Lys | Pro | Trp | Thr | Asn | Gly | Val | Gly | His | His | Thr | His |
| 690 |     |     |     |     | 695 |     |     |     | 700 |     |     |     |
| Ala | Leu | Pro | His | Ala | Lys | Pro | Pro | Val | Glu | Ser | Gly | Gly | Gly | Lys | Leu |
| 705 |     |     |     | 710 |     |     |     | 715 |     |     |     | 720 |
| Leu | Pro | Cys | Thr | Gly | Asp | Tyr | Met | Asn | Met | Ser | Pro | Val | Gly | Asp | Ser |
|     |     |     | 725 |     |     |     | 730 |     |     |     | 735 |
| Asn | Thr | Ser | Ser | Pro | Ser | Glu | Cys | Tyr | Tyr | Gly | Pro | Glu | Asp | Pro | Gln |
|     |     | 740 |     |     |     | 745 |     |     |     | 750 |
| His | Lys | Pro | Val | Leu | Ser | Tyr | Tyr | Ser | Leu | Pro | Arg | Ser | Phe | Lys | His |
|     |     | 755 |     |     |     | 760 |     |     |     | 765 |
| Thr | Gln | Arg | Pro | Gly | Glu | Pro | Glu | Glu | Gly | Ala | Arg | His | Gln | His | Leu |
| 770 |     |     |     |     | 775 |     |     |     | 780 |
| Arg | Leu | Ser | Ser | Ser | Ser | Gly | Arg | Leu | Arg | Tyr | Thr | Ala | Thr | Ala | Glu |
| 785 |     |     |     | 790 |     |     |     | 795 |     |     |     | 800 |
| Asp | Ser | Ser | Ser | Ser | Thr | Ser | Ser | Asp | Ser | Leu | Gly | Gly | Gly | Tyr | Cys |
|     |     |     | 805 |     |     |     | 810 |     |     |     | 815 |
| Gly | Ala | Arg | Pro | Glu | Ser | Ser | Leu | Thr | His | Pro | His | His | His | Val | Leu |
|     |     |     | 820 |     |     |     | 825 |     |     |     | 830 |
| Gln | Pro | His | Leu | Pro | Arg | Lys | Val | Asp | Thr | Ala | Ala | Gln | Thr | Asn | Ser |
|     |     | 835 |     |     |     | 840 |     |     |     | 845 |
| Arg | Leu | Ala | Arg | Pro | Thr | Arg | Leu | Ser | Leu | Gly | Asp | Pro | Lys | Ala | Ser |
| 850 |     |     |     | 855 |     |     |     | 860 |
| Thr | Leu | Pro | Arg | Val | Arg | Glu | Gln | Gln | Gln | Gln | Gln | Gln | Ser | Ser | Leu |
| 865 |     |     |     | 870 |     |     |     | 875 |     |     |     | 880 |
| His | Pro | Pro | Glu | Pro | Lys | Ser | Pro | Gly | Glu | Tyr | Val | Asn | Ile | Glu | Phe |
|     |     |     | 885 |     |     |     | 890 |     |     |     | 895 |
| Gly | Ser | Gly | Gln | Pro | Gly | Tyr | Leu | Ala | Gly | Pro | Ala | Thr | Ser | Arg | Ser |
|     |     |     | 900 |     |     |     | 905 |     |     |     | 910 |
| Ser | Pro | Ser | Val | Arg | Cys | Pro | Pro | Gln | Leu | His | Pro | Ala | Pro | Arg | Glu |
|     |     | 915 |     |     |     | 920 |     |     |     | 925 |
| Glu | Thr | Gly | Ser | Glu | Glu | Tyr | Met | Asn | Met | Asp | Leu | Gly | Pro | Gly | Arg |
|     | 930 |     |     |     | 935 |     |     |     | 940 |
| Arg | Ala | Thr | Trp | Gln | Glu | Ser | Gly | Gly | Val | Glu | Leu | Gly | Arg | Ile | Gly |
| 945 |     |     |     |     | 950 |     |     |     | 955 |     |     |     | 960 |
| Pro | Ala | Pro | Pro | Gly | Ser | Ala | Thr | Val | Cys | Arg | Pro | Thr | Arg | Ser | Val |
|     |     |     | 965 |     |     |     | 970 |     |     |     | 975 |
| Pro | Asn | Ser | Arg | Gly | Asp | Tyr | Met | Thr | Met | Gln | Ile | Gly | Cys | Pro | Arg |
|     |     |     | 980 |     |     |     | 985 |     |     |     | 990 |
| Gln | Ser | Tyr | Val | Asp | Thr | Ser | Pro | Val | Ala | Pro | Val | Ser | Tyr | Ala | Asp |
|     |     | 995 |     |     |     | 1000|     |     |     | 1005|
| Met | Arg | Thr | Gly | Ile | Ala | Ala | Glu | Lys | Ala | Ser | Leu | Pro | Arg | Pro | Thr |
|     |     | 1010|     |     |     | 1015|     |     |     | 1020|
| Gly | Ala | Ala | Pro | Pro | Pro | Ser | Ser | Thr | Ala | Ser | Ser | Ser | Ala | Ser | Val |
| 1025|     |     |     | 1030|     |     |     | 1035|     |     |     | 1040|
| Thr | Pro | Gln | Gly | Ala | Thr | Ala | Glu | Gln | Ala | Thr | His | Ser | Ser | Leu | Leu |
|     |     |     | 1045|     |     |     | 1050|     |     |     | 1055|
| Gly | Gly | Pro | Gln | Gly | Pro | Gly | Gly | Met | Ser | Ala | Phe | Thr | Arg | Val | Asn |
|     |     |     | 1060|     |     |     | 1065|     |     |     | 1070|

Leu Ser Pro Asn His Asn Gln Ser Ala Lys Val Ile Arg Ala Asp Thr
        1075                1080                1085

Gln Gly Cys Arg Arg Arg His Ser Ser Glu Thr Phe Ser Ala Pro Thr
        1090                1095                1100

Arg Ala Gly Asn Thr Val Pro Phe Gly Ala Gly Ala Ala Val Gly Gly
1105                1110                1115                1120

Ser Gly Gly Gly Gly Gly Gly Gly Ser Glu Asp Val Lys Arg His Ser
                1125                1130                1135

Ser Ala Ser Phe Glu Asn Val Trp Leu Arg Pro Gly Asp Leu Gly Gly
            1140                1145                1150

Val Ser Lys Glu Ser Ala Pro Val Cys Gly Ala Ala Gly Gly Leu Glu
        1155                1160                1165

Lys Ser Leu Asn Tyr Ile Asp Leu Asp Leu Ala Lys Glu His Ser Gln
        1170                1175                1180

Asp Cys Pro Ser Gln Gln Gln Ser Leu Pro Pro Pro Pro His Gln
1185                1190                1195                1200

Pro Leu Gly Ser Asn Glu Gly Asn Ser Pro Arg Arg Ser Ser Glu Asp
                1205                1210                1215

Leu Ser Asn Tyr Ala Ser Ile Ser Phe Gln Lys Gln Pro Glu Asp Arg
            1220                1225                1230

Gln Xaa ( 2 ) INFORMATION FOR SEQ ID NO:16:

( i ) SEQUENCE CHARACTERISTICS:
       ( A ) LENGTH: 1321 amino acids
       ( B ) TYPE: amino acid
       ( D ) TOPOLOGY: linear ( i i ) MOLECULE TYPE: protein ( x i ) SEQUENCE DESCRIPTION: SEQ ID NO:16:

Xaa Xaa Xaa Xaa Xaa Xaa Xaa Xaa Pro Pro Xaa Xaa Xaa Gly Xaa Xaa
1               5                   10                  15

Xaa Xaa Xaa Xaa Xaa Xaa Xaa Xaa Xaa Xaa Xaa Xaa Xaa Xaa Val Arg
            20                  25                  30

Lys Xaa Gly Tyr Leu Arg Lys Xaa Lys Xaa Xaa His Lys Arg Phe Phe
        35                  40                  45

Val Leu Arg Xaa Xaa Xaa Xaa Xaa Xaa Xaa Xaa Ala Ser Xaa Ala Gly
    50                  55                  60

Gly Xaa Xaa Xaa Xaa Pro Xaa Arg Leu Glu Tyr Glu Xaa Glu Lys
65                  70                  75                  80

Lys Trp Arg Xaa Lys Xaa Xaa Ala Pro Lys Arg Xaa Ile Xaa Leu Xaa
            85                  90                  95

Xaa Cys Xaa Asn Ile Asn Lys Arg Ala Asp Xaa Lys Xaa Lys Xaa Leu
        100                 105                 110

Xaa Ala Leu Tyr Thr Xaa Asp Glu Xaa Phe Ala Xaa Ala Ala Xaa Xaa
        115                 120                 125

Glu Xaa Glu Gln Xaa Xaa Trp Tyr Xaa Ala Leu Xaa Xaa Leu Xaa Xaa
    130                 135                 140

Xaa Xaa Xaa Xaa Xaa Xaa Xaa Gly Xaa Xaa Gly Xaa Gly Gly Ser Cys
145                 150                 155                 160

Ser Xaa Xaa Xaa Xaa Xaa Xaa Xaa Xaa Gly Ser Xaa Gly Xaa Xaa Xaa
            165                 170                 175

Xaa Xaa Xaa Xaa Xaa Xaa Xaa Xaa Thr Xaa Xaa Xaa Xaa Xaa Xaa Xaa
            180                 185                 190

| | | | | | | | | | | | | | |
|---|---|---|---|---|---|---|---|---|---|---|---|---|---|
| Glu | Val | Trp | Gln | Val | Xaa | Leu | Lys | Pro | Lys | Gly | Leu | Gly | Gln | Xaa | Lys |
| | | 195 | | | | | 200 | | | | | 205 | | | |
| Asn | Leu | Xaa | Gly | Xaa | Tyr | Arg | Leu | Cys | Leu | Xaa | Xaa | Xaa | Thr | Ile | Xaa |
| | | 210 | | | | 215 | | | | | 220 | | | | |
| Phe | Val | Lys | Leu | Asn | Xaa | Glu | Xaa | Xaa | Xaa | Xaa | Leu | Gln | Leu | Met |
| 225 | | | | | 230 | | | | | 235 | | | | 240 |
| Asn | Ile | Arg | Arg | Cys | Gly | His | Ser | Xaa | Xaa | Phe | Phe | Phe | Ile | Glu | Val |
| | | | | 245 | | | | | 250 | | | | | 255 | |
| Gly | Arg | Ser | Ala | Val | Thr | Gly | Pro | Gly | Glu | Xaa | Trp | Met | Gln | Xaa | Asp |
| | | | 260 | | | | | 265 | | | | | 270 | | |
| Asp | Ser | Val | Val | Ala | Gln | Asn | Xaa | His | Glu | Thr | Ile | Leu | Glu | Ala | Met |
| | | 275 | | | | | 280 | | | | | 285 | | | |
| Xaa | Ala | Xaa | Xaa | Xaa | Xaa | Xaa | Glu | Phe | Arg | Pro | Arg | Ser | Lys | Ser | Gln |
| | 290 | | | | | 295 | | | | | 300 | | | | |
| Ser | Ser | Xaa | Ser | Ser | Xaa | Xaa | Xaa | Pro | Ile | Ser | Val | Pro | Xaa | Xaa | Xaa |
| 305 | | | | | 310 | | | | | 315 | | | | | 320 |
| Arg | Xaa | His | His | Leu | Xaa | Asn | Xaa | Pro | Pro | Ser | Gln | Xaa | Gly | Leu | Xaa |
| | | | | 325 | | | | | 330 | | | | | 335 | |
| Arg | Arg | Ser | Arg | Thr | Xaa | Ser | Xaa | Xaa | Ala | Thr | Xaa | Pro | Ala | Lys | Xaa |
| | | | 340 | | | | | 345 | | | | | 350 | | |
| Xaa | Xaa | Ser | Xaa | Arg | Val | Arg | Xaa | Xaa | Ser | Xaa | Gly | Xaa | Gly | Xaa | Xaa |
| | | 355 | | | | | 360 | | | | | 365 | | | |
| Xaa | Xaa | Xaa | Xaa | Xaa | Xaa | Xaa | Xaa | Arg | Pro | Xaa | Ser | Val | Xaa | Gly |
| | 370 | | | | | 375 | | | | | 380 | | | | |
| Ser | Pro | Xaa | Ser | Pro | Xaa | Xaa | Xaa | Arg | Xaa | Xaa | Xaa | Xaa | Arg | Xaa | Xaa |
| 385 | | | | | 390 | | | | | 395 | | | | | 400 |
| Xaa | Xaa | Ser | Xaa | Xaa | Xaa | Xaa | Xaa | Xaa | Xaa | Xaa | Xaa | Xaa | Xaa | Xaa |
| | | | | 405 | | | | | 410 | | | | | 415 |
| Xaa | Xaa | Xaa | Xaa | Xaa | Leu | Xaa | His | Ser | Arg | Ser | Xaa | Xaa | Met | Pro | Xaa |
| | | | | 420 | | | | | 425 | | | | | 430 | |
| Xaa | Xaa | Xaa | Xaa | Pro | Xaa | Ala | Thr | Ser | Pro | Xaa | Ser | Leu | Ser | Ser | Ser |
| | | | 435 | | | | | 440 | | | | | 445 | | |
| Ser | Xaa | Xaa | Gly | Xaa | Gly | Ser | Xaa | Xaa | Xaa | Xaa | Xaa | Xaa | Ser | Xaa | Xaa |
| | 450 | | | | | 455 | | | | | 460 | | | | |
| Xaa | Xaa | Pro | Xaa | Xaa | Xaa | Xaa | Xaa | Xaa | Xaa | Xaa | Xaa | Xaa | Xaa | Xaa |
| 465 | | | | | 470 | | | | | 475 | | | | | 480 |
| Xaa | Ser | Ala | Ser | Xaa | Ser | Gly | Ser | Pro | Ser | Asp | Xaa | Gly | Phe | Xaa | Ser |
| | | | | 485 | | | | | 490 | | | | | 495 | |
| Xaa | Asp | Glu | Tyr | Gly | Ser | Ser | Pro | Xaa | Asp | Xaa | Arg | Xaa | Xaa | Ser | Ser |
| | | | 500 | | | | | 505 | | | | | 510 | | |
| Xaa | Arg | Ser | Xaa | Thr | Pro | Xaa | Ser | Xaa | Xaa | Xaa | Thr | Pro | Pro | Ala | Arg |
| | | 515 | | | | | 520 | | | | | 525 | | | |
| Xaa | Xaa | Xaa | Xaa | Xaa | Glu | Leu | Xaa | Xaa | Tyr | Xaa | Xaa | Met | Xaa | Xaa | Xaa |
| | | 530 | | | | | 535 | | | | | 540 | | | |
| Leu | Ser | Xaa | Xaa | Gly | Xaa | Xaa | Arg | Xaa | Xaa | Xaa | Xaa | Xaa | Gly | Ala |
| 545 | | | | | 550 | | | | | 555 | | | | | 560 |
| Xaa | Asp | Leu | Asp | Xaa | Xaa | Xaa | Arg | Lys | Arg | Thr | Xaa | Ser | Xaa | Xaa | Thr |
| | | | | 565 | | | | | 570 | | | | | 575 | |
| Xaa | Xaa | Xaa | Xaa | Xaa | Gln | Xaa | Xaa | Gln | Xaa | Ser | Xaa | Ala | Ser | Xaa | Xaa |
| | | | | 580 | | | | | 585 | | | | | 590 | |
| Glu | Tyr | Thr | Xaa | Met | Xaa | Ala | Xaa | Xaa | Xaa | Gly | Ser | Xaa | Gly | Arg | Leu |
| | | | 595 | | | | | 600 | | | | | 605 | | |
| Xaa | Pro | Xaa | Xaa | Xaa | Xaa | Xaa | Ser | Xaa | Xaa | Val | Xaa | Xaa | Xaa | Xaa | Tyr |
| | | 610 | | | | | 615 | | | | | 620 | | | |

| | | | | | | | | | | | | | |
|---|---|---|---|---|---|---|---|---|---|---|---|---|---|
| Pro | Glu | Xaa | Xaa | Xaa | Xaa | Xaa | Xaa | Gly | Xaa | His | Xaa | Xaa | Xaa | Xaa |
| 625 | | | | 630 | | | | 635 | | | | | 640 |
| Ser | Asn | Leu | Xaa | Xaa | Asp | Asp | Gly | Tyr | Met | Pro | Met | Xaa | Pro | Gly | Ala |
| | | | 645 | | | | | 650 | | | | | 655 |
| Ala | Xaa | Xaa | Xaa | Xaa | Xaa | Asn | Xaa | Xaa | Xaa | Xaa | Xaa | Asp | Tyr | Met |
| | | | 660 | | | | 665 | | | | | 670 | | |
| Pro | Met | Ser | Pro | Xaa | Ser | Val | Ser | Ala | Pro | Xaa | Gln | Ile | Xaa | Xaa | Pro |
| | | 675 | | | | 680 | | | | | 685 | | | |
| Arg | Xaa | Xaa | Xaa | Xaa | Xaa | Xaa | Pro | Xaa | Gly | Xaa | Xaa | Xaa | Xaa | Pro |
| | 690 | | | | | 695 | | | | 700 | | | | |
| Xaa | Xaa | Xaa | Xaa | Xaa | Xaa | Xaa | Xaa | Xaa | Xaa | Gly | Gly | Gly | Xaa | Xaa |
| 705 | | | | | 710 | | | | 715 | | | | | 720 |
| Xaa | Ser | Ser | Xaa | Xaa | Xaa | Xaa | Xaa | Pro | Xaa | Xaa | Ser | Xaa | Tyr | Xaa | Xaa |
| | | | | 725 | | | | 730 | | | | | 735 | | |
| Xaa | Trp | Xaa | Xaa | Xaa | Lys | Xaa | Xaa | Xaa | Glu | Xaa | Xaa | Xaa | Xaa | Lys | Leu |
| | | | 740 | | | | | 745 | | | | | 750 | | |
| Leu | Pro | Xaa | Gly | Asp | Tyr | Xaa | Asn | Met | Ser | Pro | Xaa | Xaa | Xaa | Xaa | Xaa |
| | | 755 | | | | 760 | | | | | 765 | | | | |
| Xaa | Xaa | Xaa | Xaa | Pro | Xaa | Xaa | Xaa | Xaa | Xaa | Xaa | Xaa | Gly | Xaa | Glu |
| | 770 | | | | 775 | | | | | 780 | | | | |
| Xaa | Xaa | Xaa | Xaa | Xaa | Pro | Xaa | Xaa | Xaa | Tyr | Xaa | Ser | Leu | Pro | Arg | Ser |
| 785 | | | | | 790 | | | | 795 | | | | | 800 |
| Xaa | Lys | Xaa | Xaa | Xaa | Xaa | Xaa | Xaa | Gly | Xaa | Xaa | Xaa | Gln | Xaa | Xaa | Xaa |
| | | | | 805 | | | | 810 | | | | | 815 | | |
| Xaa | Ser | Ser | Xaa | Xaa | Gly | Arg | Xaa | Xaa | Xaa | Xaa | Xaa | Xaa | Xaa | Glu | Xaa |
| | | | 820 | | | | | 825 | | | | | 830 | | |
| Xaa | Xaa | Xaa | Xaa | Xaa | Gly | Xaa | Xaa | Xaa | Xaa | Ala | Xaa | Xaa | Ser | Xaa |
| | | 835 | | | | 840 | | | | | 845 | | | |
| Thr | Xaa | Pro | His | His | Xaa | Xaa | Xaa | Xaa | Xaa | Xaa | Xaa | Xaa | Xaa | Xaa |
| | 850 | | | | | 855 | | | | 860 | | | | |
| Xaa | Xaa | Xaa | Xaa | Xaa | Xaa | Xaa | Xaa | Xaa | Xaa | Xaa | Xaa | Arg | Xaa | Xaa |
| 865 | | | | | 870 | | | | | 875 | | | | 880 |
| Arg | Pro | Thr | Arg | Leu | Ser | Leu | Xaa | Xaa | Xaa | Xaa | Thr | Leu | Pro | Xaa | Xaa |
| | | | | 885 | | | | | 890 | | | | | 895 | |
| Xaa | Glu | Xaa | Xaa | Xaa | Pro | Xaa | Glu | Pro | Lys | Ser | Pro | Gly | Glu | Tyr | Xaa |
| | | | 900 | | | | 905 | | | | | 910 | | | |
| Asn | Ile | Xaa | Phe | Gly | Xaa | Xaa | Xaa | Xaa | Xaa | Xaa | Xaa | Xaa | Xaa | Pro |
| | | 915 | | | | 920 | | | | | 925 | | | |
| Xaa | Xaa | Leu | Ala | Xaa | Xaa | Ala | Xaa | Ser | Xaa | Ser | Xaa | Xaa | Ser | Xaa | Xaa |
| 930 | | | | | 935 | | | | | 940 | | | | | |
| Xaa | Pro | Xaa | Xaa | Xaa | Xaa | Xaa | Xaa | Xaa | Xaa | Xaa | Thr | Xaa | Ser | Xaa |
| 945 | | | | | 950 | | | | | 955 | | | | 960 |
| Xaa | Xaa | Xaa | Xaa | Xaa | Xaa | Xaa | Xaa | Tyr | Met | Asn | Xaa | Asp | Xaa | Xaa |
| | | | | 965 | | | | 970 | | | | | 975 | |
| Xaa | Xaa | Xaa | Xaa | Xaa | Xaa | Xaa | Xaa | Xaa | Xaa | Gly | Xaa | Xaa | Xaa | Gly |
| | | | 980 | | | | | 985 | | | | | 990 | |
| Xaa | Xaa | Xaa | Xaa | Xaa | Xaa | Xaa | Xaa | Xaa | Xaa | Xaa | Xaa | Xaa | Xaa |
| | | | 995 | | | | | 1000 | | | | | 1005 |
| Xaa | Xaa | Pro | Xaa | Xaa | Ser | Xaa | Xaa | Xaa | Xaa | Xaa | Xaa | Xaa | Xaa |
| | 1010 | | | | | 1015 | | | | | 1020 | | | |
| Pro | Xaa | Xaa | Xaa | Gly | Asp | Xaa | Xaa | Xaa | Xaa | Xaa | Xaa | Xaa | Xaa |
| 1025 | | | | | 1030 | | | | | 1035 | | | | 1040 |
| Xaa | Ser | Xaa | Xaa | Xaa | Thr | Xaa | Xaa | Xaa | Xaa | Xaa | Xaa | Ser | Xaa | Xaa | Gly |

-continued

```
                        1045                    1050                    1055
Xaa  Xaa  Xaa  Xaa  Xaa  Xaa  Xaa  Xaa  Xaa  Xaa  Xaa  Xaa  Ala  Xaa  Pro
                    1060                    1065                    1070
Pro  Xaa  Xaa  Xaa  Xaa  Ala  Xaa  Xaa  Xaa  Xaa  Xaa  Xaa  Xaa  Xaa  Xaa
                1075                    1080                    1085
Xaa  Xaa  Xaa  Xaa  Xaa  Xaa  Xaa  Xaa  Xaa  Ser  Leu  Xaa  Xaa  Xaa  Xaa
            1090                    1095                    1100
Gly  Xaa  Xaa  Ala  Phe  Xaa  Xaa  Val  Xaa  Xaa  Xaa  Pro  Xaa  Xaa  Xaa
1105                    1110                    1115                    1120
Xaa  Ala  Lys  Val  Ile  Arg  Ala  Asp  Xaa  Gln  Gly  Xaa  Arg  Arg  His
                    1125                    1130                    1135
Ser  Ser  Glu  Thr  Phe  Ser  Xaa  Xaa  Thr  Xaa  Xaa  Xaa  Xaa  Xaa  Pro
                1140                    1145                    1150
Xaa  Xaa  Ala  Xaa  Xaa  Xaa  Lys  Arg  His  Xaa  Ser  Ala  Ser  Xaa  Glu  Asn
            1155                    1160                    1165
Val  Xaa  Leu  Arg  Xaa  Xaa  Xaa  Xaa  Gly  Xaa  Xaa  Xaa  Xaa  Gly  Xaa  Xaa
        1170                    1175                    1180
Xaa  Glu  Xaa  Xaa  Xaa  Xaa  Xaa  Gly  Xaa  Ala  Xaa  Xaa  Xaa  Xaa  Xaa  Xaa
1185                    1190                    1195                    1200
Xaa  Xaa  Xaa  Xaa  Xaa  Xaa  Xaa  Xaa  Xaa  Xaa  Xaa  Xaa  Xaa  Xaa
                    1205                    1210                    1215
Xaa  Xaa  Xaa  Xaa  Xaa  Xaa  Xaa  Xaa  Xaa  Xaa  Xaa  Xaa  Xaa  Xaa  Xaa
                1220                    1225                    1230
Xaa  Xaa  Gly  Xaa  Xaa  Xaa  Xaa  Leu  Asn  Tyr  Ile  Xaa  Xaa  Asp  Xaa  Xaa
            1235                    1240                    1245
Xaa  Glu  Xaa  Xaa  Xaa  Xaa  Xaa  Xaa  Ser  Gln  Xaa  Xaa  Pro  Xaa  Xaa  Xaa
1250                    1255                    1260
Xaa  Ser  Xaa  Xaa  Xaa  Xaa  Xaa  Xaa  Xaa  Xaa  Leu  Xaa  Xaa  Xaa  Xaa
1265                    1270                    1275                    1280
Gly  Xaa  Ser  Xaa  Xaa  Xaa  Xaa  Xaa  Xaa  Xaa  Xaa  Xaa  Xaa  Xaa  Xaa
                    1285                    1290                    1295
Xaa  Xaa  Xaa  Ser  Xaa  Tyr  Ala  Ser  Ile  Xaa  Phe  Xaa  Xaa  Xaa  Xaa  Xaa
                1300                    1305                    1310
Xaa  Xaa  Xaa  Xaa  Xaa  Xaa  Xaa  Xaa  Xaa
            1315                    1320
```

( 2 ) INFORMATION FOR SEQ ID NO:17:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:17:

```
Glu  Tyr  Tyr  Glu  Ser  Glu  Lys
 1                    5
```

( 2 ) INFORMATION FOR SEQ ID NO:18:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide (v) FRAGMENT TYPE: internal (xi) SEQUENCE DESCRIPTION: SEQ ID NO:18:

Glu  Tyr  Phe  Ala  Val  Ala  Ala
             1                   5

(2) INFORMATION FOR SEQ ID NO:19:

(i) SEQUENCE CHARACTERISTICS:
                (A) LENGTH: 6 amino acids
                (B) TYPE: amino acid
                (D) TOPOLOGY: linear (ii) MOLECULE TYPE: peptide (v) FRAGMENT TYPE: internal (xi) SEQUENCE DESCRIPTION: SEQ ID NO:19:

Trp  Tyr  Arg  Ala  Leu  Thr
             1                   5

(2) INFORMATION FOR SEQ ID NO:20:

(i) SEQUENCE CHARACTERISTICS:
                (A) LENGTH: 6 amino acids
                (B) TYPE: amino acid
                (D) TOPOLOGY: linear (ii) MOLECULE TYPE: peptide (v) FRAGMENT TYPE: internal (xi) SEQUENCE DESCRIPTION: SEQ ID NO:20:

Asn  Tyr  Gly  Leu  Val  Thr
             1                   5

(2) INFORMATION FOR SEQ ID NO:21:

(i) SEQUENCE CHARACTERISTICS:
                (A) LENGTH: 6 amino acids
                (B) TYPE: amino acid
                (D) TOPOLOGY: linear (ii) MOLECULE TYPE: peptide (v) FRAGMENT TYPE: internal (xi) SEQUENCE DESCRIPTION: SEQ ID NO:21:

Glu  Tyr  Gly  Ser  Ser  Pro
             1                   5

(2) INFORMATION FOR SEQ ID NO:22:

(i) SEQUENCE CHARACTERISTICS:
                (A) LENGTH: 6 amino acids
                (B) TYPE: amino acid
                (D) TOPOLOGY: linear (ii) MOLECULE TYPE: peptide (v) FRAGMENT TYPE: internal (xi) SEQUENCE DESCRIPTION: SEQ ID NO:22:

Leu  Tyr  Gly  Tyr  Met  Ser
             1                   5

(2) INFORMATION FOR SEQ ID NO:23:

(i) SEQUENCE CHARACTERISTICS:
                (A) LENGTH: 6 amino acids (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:23:

Gly Tyr Met Ser Met Asp
    1               5

(2) INFORMATION FOR SEQ ID NO:24:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:24:

Glu Tyr Thr Leu Met Arg
    1               5

(2) INFORMATION FOR SEQ ID NO:25:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:25:

Pro Tyr Pro Glu Asp Tyr
    1               5

(2) INFORMATION FOR SEQ ID NO:26:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:26:

Asp Tyr Gly Asp Leu Glu
    1               5

(2) INFORMATION FOR SEQ ID NO:27:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:27:

Gly Tyr Met Pro Met Thr
    1               5

( 2 ) INFORMATION FOR SEQ ID NO:28:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:28:

Asp Tyr Met Pro Met Ser
1                   5

( 2 ) INFORMATION FOR SEQ ID NO:29:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:29:

Gly Tyr Met Arg Met Trp
1                   5

( 2 ) INFORMATION FOR SEQ ID NO:30:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:30:

Asp Tyr Leu Asn Met Ser
1                   5

( 2 ) INFORMATION FOR SEQ ID NO:31:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:31:

Gln Tyr Val Leu Met Ser
1                   5

( 2 ) INFORMATION FOR SEQ ID NO:32:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:32:

Glu Tyr Pro Leu Pro Thr
1               5

( 2 ) INFORMATION FOR SEQ ID NO:33:

( i ) SEQUENCE CHARACTERISTICS:
      ( A ) LENGTH: 6 amino acids
      ( B ) TYPE: amino acid
      ( D ) TOPOLOGY: linear ( i i ) MOLECULE TYPE: peptide ( v ) FRAGMENT TYPE: internal ( x i ) SEQUENCE DESCRIPTION: SEQ ID NO:33:

Glu Tyr Ile Asn Ile Asp
1               5

( 2 ) INFORMATION FOR SEQ ID NO:34:

( i ) SEQUENCE CHARACTERISTICS:
      ( A ) LENGTH: 6 amino acids
      ( B ) TYPE: amino acid
      ( D ) TOPOLOGY: linear ( i i ) MOLECULE TYPE: peptide ( v ) FRAGMENT TYPE: internal ( x i ) SEQUENCE DESCRIPTION: SEQ ID NO:34:

Asp Tyr Met Asn Leu Asp
1               5

( 2 ) INFORMATION FOR SEQ ID NO:35:

( i ) SEQUENCE CHARACTERISTICS:
      ( A ) LENGTH: 6 amino acids
      ( B ) TYPE: amino acid
      ( D ) TOPOLOGY: linear ( i i ) MOLECULE TYPE: peptide ( v ) FRAGMENT TYPE: internal ( x i ) SEQUENCE DESCRIPTION: SEQ ID NO:35:

Leu Tyr Arg Leu Pro Pro
1               5

( 2 ) INFORMATION FOR SEQ ID NO:36:

( i ) SEQUENCE CHARACTERISTICS:
      ( A ) LENGTH: 6 amino acids
      ( B ) TYPE: amino acid
      ( D ) TOPOLOGY: linear ( i i ) MOLECULE TYPE: peptide ( v ) FRAGMENT TYPE: internal ( x i ) SEQUENCE DESCRIPTION: SEQ ID NO:36:

Pro Tyr Thr Glu Met Ala
1               5

( 2 ) INFORMATION FOR SEQ ID NO:37:

( i ) SEQUENCE CHARACTERISTICS:
      ( A ) LENGTH: 6 amino acids
      ( B ) TYPE: amino acid
      ( D ) TOPOLOGY: linear ( i i ) MOLECULE TYPE: peptide ( v ) FRAGMENT TYPE: internal ( x i ) SEQUENCE DESCRIPTION: SEQ ID NO:37:

Asn Tyr Ile Ala Ile Asp
1               5

( 2 ) INFORMATION FOR SEQ ID NO:38:

( i ) SEQUENCE CHARACTERISTICS:
( A ) LENGTH: 6 amino acids
( B ) TYPE: amino acid
( D ) TOPOLOGY: linear ( i i ) MOLECULE TYPE: peptide ( v ) FRAGMENT TYPE: internal ( x i ) SEQUENCE DESCRIPTION: SEQ ID NO:38:

Thr Tyr Ala Ser Ile Asp
1               5

( 2 ) INFORMATION FOR SEQ ID NO:39:

( i ) SEQUENCE CHARACTERISTICS:
( A ) LENGTH: 6 amino acids
( B ) TYPE: amino acid
( D ) TOPOLOGY: linear ( i i ) MOLECULE TYPE: peptide ( v ) FRAGMENT TYPE: internal ( x i ) SEQUENCE DESCRIPTION: SEQ ID NO:39:

Asn Tyr Ala Ser Ile Ser
1               5

( 2 ) INFORMATION FOR SEQ ID NO:40:

( i ) SEQUENCE CHARACTERISTICS:
( A ) LENGTH: 6 amino acids
( B ) TYPE: amino acid
( D ) TOPOLOGY: linear ( i i ) MOLECULE TYPE: peptide ( v ) FRAGMENT TYPE: internal ( x i ) SEQUENCE DESCRIPTION: SEQ ID NO:40:

Asn Tyr Ile Asp Leu Asp
1               5

( 2 ) INFORMATION FOR SEQ ID NO:41:

( i ) SEQUENCE CHARACTERISTICS:
( A ) LENGTH: 6 amino acids
( B ) TYPE: amino acid
( D ) TOPOLOGY: linear ( i i ) MOLECULE TYPE: peptide ( v ) FRAGMENT TYPE: internal ( x i ) SEQUENCE DESCRIPTION: SEQ ID NO:41:

Ser Tyr Ala Asp Met Arg
1               5

( 2 ) INFORMATION FOR SEQ ID NO:42:

( i ) SEQUENCE CHARACTERISTICS:
  ( A ) LENGTH: 6 amino acids
  ( B ) TYPE: amino acid
  ( D ) TOPOLOGY: linear ( i i ) MOLECULE TYPE: peptide ( v ) FRAGMENT TYPE: internal ( x i ) SEQUENCE DESCRIPTION: SEQ ID NO:42:

Ser Tyr Val Asp Thr Ser
 1               5

( 2 ) INFORMATION FOR SEQ ID NO:43:

( i ) SEQUENCE CHARACTERISTICS:
    ( A ) LENGTH: 6 amino acids
    ( B ) TYPE: amino acid
    ( D ) TOPOLOGY: linear ( i i ) MOLECULE TYPE: peptide ( v ) FRAGMENT TYPE: internal ( x i ) SEQUENCE DESCRIPTION: SEQ ID NO:43:

Asp Tyr Met Thr Met Gln
 1               5

( 2 ) INFORMATION FOR SEQ ID NO:44:

( i ) SEQUENCE CHARACTERISTICS:
    ( A ) LENGTH: 6 amino acids
    ( B ) TYPE: amino acid
    ( D ) TOPOLOGY: linear ( i i ) MOLECULE TYPE: peptide ( v ) FRAGMENT TYPE: internal ( x i ) SEQUENCE DESCRIPTION: SEQ ID NO:44:

Glu Tyr Met Asn Met Asp
 1               5

( 2 ) INFORMATION FOR SEQ ID NO:45:

( i ) SEQUENCE CHARACTERISTICS:
    ( A ) LENGTH: 6 amino acids
    ( B ) TYPE: amino acid
    ( D ) TOPOLOGY: linear ( i i ) MOLECULE TYPE: peptide ( v ) FRAGMENT TYPE: internal ( x i ) SEQUENCE DESCRIPTION: SEQ ID NO:45:

Glu Tyr Val Asn Ile Glu
 1               5

( 2 ) INFORMATION FOR SEQ ID NO:46:

( i ) SEQUENCE CHARACTERISTICS:
    ( A ) LENGTH: 8 amino acids
    ( B ) TYPE: amino acid
    ( D ) TOPOLOGY: linear ( i i ) MOLECULE TYPE: peptide ( v ) FRAGMENT TYPE: internal ( x i ) SEQUENCE DESCRIPTION: SEQ ID NO:46:

```
      Glu  Cys  Tyr  Tyr  Gly  Pro  Glu  Asp
      1                 5
```

( 2 ) INFORMATION FOR SEQ ID NO:47:

( i ) SEQUENCE CHARACTERISTICS:
      ( A ) LENGTH: 6 amino acids
      ( B ) TYPE: amino acid
      ( D ) TOPOLOGY: linear ( i i ) MOLECULE TYPE: peptide ( v ) FRAGMENT TYPE: internal ( x i ) SEQUENCE DESCRIPTION: SEQ ID NO:47:

```
      Asp  Tyr  Met  Asn  Met  Ser
      1                 5
```

( 2 ) INFORMATION FOR SEQ ID NO:48:

( i ) SEQUENCE CHARACTERISTICS:
      ( A ) LENGTH: 6 amino acids
      ( B ) TYPE: amino acid
      ( D ) TOPOLOGY: linear ( i i ) MOLECULE TYPE: peptide ( v ) FRAGMENT TYPE: internal ( x i ) SEQUENCE DESCRIPTION: SEQ ID NO:48:

```
      Gly  Tyr  Met  Met  Met  Ser
      1                 5
```

( 2 ) INFORMATION FOR SEQ ID NO:49:

( i ) SEQUENCE CHARACTERISTICS:
      ( A ) LENGTH: 6 amino acids
      ( B ) TYPE: amino acid
      ( D ) TOPOLOGY: linear ( i i ) MOLECULE TYPE: peptide ( v ) FRAGMENT TYPE: internal ( x i ) SEQUENCE DESCRIPTION: SEQ ID NO:49:

```
      Gly  Tyr  Met  Pro  Met  Ser
      1                 5
```

( 2 ) INFORMATION FOR SEQ ID NO:50:

( i ) SEQUENCE CHARACTERISTICS:
      ( A ) LENGTH: 6 amino acids
      ( B ) TYPE: amino acid
      ( D ) TOPOLOGY: linear ( i i ) MOLECULE TYPE: peptide ( v ) FRAGMENT TYPE: internal ( x i ) SEQUENCE DESCRIPTION: SEQ ID NO:50:

```
      Ser  Tyr  Pro  Glu  Glu  Gly
      1                 5
```

( 2 ) INFORMATION FOR SEQ ID NO:51:

( i ) SEQUENCE CHARACTERISTICS:
      ( A ) LENGTH: 6 amino acids
      ( B ) TYPE: amino acid
      ( D ) TOPOLOGY: linear ( i i ) MOLECULE TYPE: peptide ( v ) FRAGMENT TYPE: internal ( x i ) SEQUENCE DESCRIPTION: SEQ ID NO:51:

Glu Tyr Thr Glu Met Met
1               5

( 2 ) INFORMATION FOR SEQ ID NO:52:

( i ) SEQUENCE CHARACTERISTICS:
( A ) LENGTH: 6 amino acids
( B ) TYPE: amino acid
( D ) TOPOLOGY: linear ( i i ) MOLECULE TYPE: peptide ( v ) FRAGMENT TYPE: internal ( x i ) SEQUENCE DESCRIPTION: SEQ ID NO:52:

Asn Tyr Ile Cys Met Gly
1               5

( 2 ) INFORMATION FOR SEQ ID NO:53:

( i ) SEQUENCE CHARACTERISTICS:
( A ) LENGTH: 6 amino acids
( B ) TYPE: amino acid
( D ) TOPOLOGY: linear ( i i ) MOLECULE TYPE: peptide ( v ) FRAGMENT TYPE: internal ( x i ) SEQUENCE DESCRIPTION: SEQ ID NO:53:

Ser Tyr Asp Thr Gly Pro
1               5

( 2 ) INFORMATION FOR SEQ ID NO:54:

( i ) SEQUENCE CHARACTERISTICS:
( A ) LENGTH: 6 amino acids
( B ) TYPE: amino acid
( D ) TOPOLOGY: linear ( i i ) MOLECULE TYPE: peptide ( v ) FRAGMENT TYPE: internal ( x i ) SEQUENCE DESCRIPTION: SEQ ID NO:54:

Trp Tyr Gln Ala Leu Leu
1               5

( 2 ) INFORMATION FOR SEQ ID NO:55:

( i ) SEQUENCE CHARACTERISTICS:
( A ) LENGTH: 7 amino acids
( B ) TYPE: amino acid
( D ) TOPOLOGY: linear ( i i ) MOLECULE TYPE: peptide ( v ) FRAGMENT TYPE: internal ( x i ) SEQUENCE DESCRIPTION: SEQ ID NO:55:

Glu Tyr Tyr Glu Asn Glu Lys
1               5

( 2 ) INFORMATION FOR SEQ ID NO:56:

( i ) SEQUENCE CHARACTERISTICS:

(A) LENGTH: 5 amino acids
(B) TYPE: amino acid
(D) TOPOLOGY: linear (ii) MOLECULE TYPE: peptide (v) FRAGMENT TYPE: internal (ix) FEATURE:
(A) NAME/KEY: Modified-site
(B) LOCATION: 3
(D) OTHER INFORMATION: /note= "Xaa, is an unknown amino acid"

(xi) SEQUENCE DESCRIPTION: SEQ ID NO:56:

Trp Ser Xaa Trp Ser
1               5

(2) INFORMATION FOR SEQ ID NO:57:

(i) SEQUENCE CHARACTERISTICS:
(A) LENGTH: 4 amino acids
(B) TYPE: amino acid
(D) TOPOLOGY: linear (ii) MOLECULE TYPE: peptide (v) FRAGMENT TYPE: internal (ix) FEATURE:
(A) NAME/KEY: Modified-site
(B) LOCATION: 3
(D) OTHER INFORMATION: /note= "Xaa, is an unknown amino acid"

(xi) SEQUENCE DESCRIPTION: SEQ ID NO:57:

Asn Pro Xaa Tyr
1

(2) INFORMATION FOR SEQ ID NO:58:

(i) SEQUENCE CHARACTERISTICS:
(A) LENGTH: 6 amino acids
(B) TYPE: amino acid
(D) TOPOLOGY: linear (ii) MOLECULE TYPE: peptide (v) FRAGMENT TYPE: internal (ix) FEATURE:
(A) NAME/KEY: Modified-site
(B) LOCATION: 3,5
(D) OTHER INFORMATION: /note= "Xaa, are unknown amino acids"

(xi) SEQUENCE DESCRIPTION: SEQ ID NO:58:

Asn Pro Xaa Tyr Xaa Ser
1               5

(2) INFORMATION FOR SEQ ID NO:59:

(i) SEQUENCE CHARACTERISTICS:
(A) LENGTH: 4 amino acids
(B) TYPE: amino acid
(D) TOPOLOGY: linear (ii) MOLECULE TYPE: peptide (v) FRAGMENT TYPE: internal (ix) FEATURE:
(A) NAME/KEY: Modified-site
(B) LOCATION: 2-3
(D) OTHER INFORMATION: /note= "Xaa, is an unknown amino acid"

(xi) SEQUENCE DESCRIPTION: SEQ ID NO:59:

Tyr  Xaa  Xaa  Met
          1

( 2 ) INFORMATION FOR SEQ ID NO:60:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:60:

Tyr  Val  Asn  Ile
          1

( 2 ) INFORMATION FOR SEQ ID NO:61:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:61:

Tyr  Ile  Asp  Leu
          1

( 2 ) INFORMATION FOR SEQ ID NO:62:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:62:

Tyr  Ala  Ser  Ile
          1

( 2 ) INFORMATION FOR SEQ ID NO:63:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( v ) FRAGMENT TYPE: internal ( i x ) FEATURE:
        ( A ) NAME/KEY: Modified-site
        ( B ) LOCATION: 2-5,8,10
        ( D ) OTHER INFORMATION: /note= "Xaa, if present, are unknown am
            acids"

( x i ) SEQUENCE DESCRIPTION: SEQ ID NO:63:

Leu  Xaa  Xaa  Xaa  Xaa  Asn  Pro  Xaa  Tyr  Xaa  Ser  Ser
          1                    5                         1 0

( 2 ) INFORMATION FOR SEQ ID NO:64:

(i) SEQUENCE CHARACTERISTICS:
   (A) LENGTH: 1321 amino acids
   (B) TYPE: amino acid
   (D) TOPOLOGY: linear (ii) MOLECULE TYPE: protein (xi) SEQUENCE DESCRIPTION: SEQ ID NO:64:

```
Met  Ala  Ser  Ala  Pro  Leu  Pro  Gly  Pro  Pro  Ala  Ser  Gly  Gly  Gly  Glu
 1                  5                   10                            15

Gly  Pro  Asn  Leu  Asn  Asn  Asn  Asn  Asn  Asn  Asn  His  Ser  Val  Arg
            20                   25                       30

Lys  Cys  Gly  Tyr  Leu  Arg  Lys  Gln  Lys  His  Gly  His  Lys  Arg  Phe  Phe
                 35                  40                      45

Val  Leu  Arg  Gly  Pro  Gly  Thr  Gly  Gly  Asp  Glu  Ala  Ser  Ala  Ala  Gly
      50                       55                       60

Gly  Ser  Pro  Pro  Gln  Pro  Pro  Arg  Leu  Glu  Tyr  Tyr  Glu  Ser  Glu  Lys
 65                      70                      75                          80

Lys  Trp  Arg  Ser  Lys  Ala  Gly  Ala  Pro  Lys  Arg  Val  Ile  Ala  Leu  Asp
                      85                       90                      95

Cys  Cys  Leu  Asn  Ile  Asn  Lys  Arg  Ala  Asp  Ala  Lys  His  Lys  Tyr  Leu
                100                     105                     110

Ile  Ala  Leu  Tyr  Thr  Lys  Asp  Glu  Tyr  Phe  Ala  Val  Ala  Ala  Glu  Asn
           115                     120                     125

Glu  Gln  Glu  Gln  Glu  Gly  Trp  Tyr  Arg  Ala  Leu  Thr  Asp  Leu  Val  Ser
      130                     135                     140

Glu  Gly  Arg  Ser  Gly  Glu  Gly  Gly  Ser  Gly  Thr  Thr  Gly  Gly  Ser  Cys
145                       150                     155                     160

Ser  Ala  Ser  Leu  Pro  Gly  Val  Leu  Gly  Gly  Ser  Ala  Gly  Ala  Ala  Gly
                 165                     170                          175

Cys  Asp  Asp  Asn  Tyr  Gly  Leu  Val  Thr  Pro  Ala  Thr  Ala  Val  Tyr  Arg
                180                     185                     190

Glu  Val  Trp  Gln  Val  Asn  Leu  Lys  Pro  Lys  Gly  Leu  Gly  Gln  Ser  Lys
           195                     200                     205

Asn  Leu  Thr  Gly  Val  Tyr  Arg  Leu  Cys  Leu  Ser  Ala  Arg  Thr  Ile  Gly
      210                     215                     220

Phe  Val  Lys  Leu  Asn  Cys  Glu  Gln  Pro  Ser  Val  Thr  Leu  Gln  Leu  Met
225                       230                     235                     240

Asn  Ile  Arg  Arg  Cys  Gly  His  Ser  Asp  Ser  Phe  Phe  Phe  Ile  Glu  Val
                      245                     250                     255

Gly  Arg  Ser  Ala  Val  Thr  Gly  Pro  Gly  Glu  Leu  Trp  Met  Gln  Ala  Asp
                 260                     265                     270

Asp  Ser  Val  Val  Ala  Gln  Asn  Ile  His  Glu  Thr  Ile  Leu  Glu  Ala  Met
           275                     280                     285

Lys  Ala  Leu  Lys  Glu  Leu  Phe  Glu  Phe  Arg  Pro  Arg  Ser  Lys  Ser  Gln
      290                     295                     300

Ser  Ser  Gly  Ser  Ser  Ala  Thr  His  Pro  Ile  Ser  Val  Pro  Gly  Ala  Arg
305                       310                     315                     320

Arg  His  His  His  Leu  Val  Asn  Leu  Pro  Pro  Ser  Gln  Thr  Gly  Leu  Val
                      325                     330                     335

Arg  Arg  Ser  Arg  Thr  Asp  Ser  Leu  Ala  Ala  Thr  Pro  Pro  Ala  Ala  Lys
                 340                     345                     350

Cys  Thr  Ser  Cys  Arg  Val  Arg  Thr  Ala  Ser  Glu  Gly  Asp  Gly  Gly  Ala
           355                     360                     365

Ala  Gly  Gly  Ala  Gly  Thr  Ala  Gly  Gly  Arg  Pro  Met  Ser  Val  Ala  Gly
```

-continued

|   |   |   | 370 |   |   |   | 375 |   |   |   | 380 |   |   |   |
|---|---|---|---|---|---|---|---|---|---|---|---|---|---|---|
| Ser 385 | Pro | Leu | Ser | Pro 390 | Gly | Pro | Val | Arg | Ala 395 | Pro | Leu | Ser | Arg | Ser His 400 |
| Thr | Leu | Ser | Ala | Gly 405 | Cys | Gly | Gly | Arg | Pro 410 | Ser | Lys | Val | Thr | Leu Ala 415 |
| Pro | Ala | Gly | Gly 420 | Ala | Leu | Gln | His | Ser 425 | Arg | Ser | Met | Ser | Met 430 | Pro Val |
| Ala | His | Ser 435 | Pro | Pro | Ala | Ala | Thr 440 | Ser | Pro | Gly | Ser | Leu 445 | Ser | Ser Ser |
| Ser | Gly 450 | His | Gly | Ser | Gly | Ser 455 | Tyr | Pro | Leu | Pro | Gly 460 | Ser | His | Pro |
| His 465 | Leu | Pro | His | Pro 470 | Leu | His | His | Pro | Gln 475 | Gly | Gln | Arg | Pro | Ser Ser 480 |
| Gly | Ser | Ala | Ser | Ala 485 | Ser | Gly | Ser | Pro | Ser 490 | Asp | Pro | Gly | Phe | Met Ser 495 |
| Leu | Asp | Glu | Tyr 500 | Gly | Ser | Ser | Pro | Gly 505 | Asp | Leu | Arg | Ala | Phe 510 | Ser Ser |
| His | Arg | Ser 515 | Asn | Thr | Pro | Glu | Ser 520 | Ile | Ala | Glu | Thr | Pro 525 | Pro | Ala Arg |
| Asp | Gly 530 | Ser | Gly | Gly | Glu | Leu 535 | Tyr | Gly | Tyr | Met | Ser 540 | Met | Asp | Arg Pro |
| Leu 545 | Ser | His | Cys | Gly | Arg 550 | Pro | Tyr | Arg | Arg | Val 555 | Ser | Gly | Asp | Gly Ala 560 |
| Gln | Asp | Leu | Asp | Arg 565 | Gly | Leu | Arg | Lys | Arg 570 | Thr | Tyr | Ser | Leu | Thr Thr 575 |
| Pro | Ala | Arg | Gln 580 | Arg | Gln | Val | Pro | Gln 585 | Pro | Ser | Ser | Ala | Ser 590 | Leu Asp |
| Glu | Tyr | Thr 595 | Leu | Met | Arg | Ala | Thr 600 | Phe | Ser | Gly | Ser | Ser 605 | Gly | Arg Leu |
| Cys | Pro 610 | Ser | Phe | Pro | Ala | Ser 615 | Ser | Pro | Lys | Val | Ala 620 | Tyr | Asn | Pro Tyr |
| Pro 625 | Glu | Asp | Tyr | Gly | Asp 630 | Ile | Glu | Ile | Gly | Ser 635 | His | Lys | Ser | Ser Ser 640 |
| Ser | Asn | Leu | Gly | Ala 645 | Asp | Asp | Gly | Tyr | Met 650 | Pro | Met | Thr | Pro | Gly Ala 655 |
| Ala | Leu | Arg | Ser 660 | Gly | Gly | Pro | Asn | Ser 665 | Cys | Lys | Ser | Asp | Asp 670 | Tyr Met |
| Pro | Met | Ser 675 | Pro | Thr | Ser | Val | Ser 680 | Ala | Pro | Lys | Gln | Ile 685 | Leu | Gln Pro |
| Arg | Leu 690 | Ala | Ala | Ala | Leu | Pro 695 | Pro | Ser | Gly | Ala | Ala 700 | Val | Pro | Ala Pro |
| Pro 705 | Ser | Gly | Val | Gly | Arg 710 | Thr | Phe | Pro | Val | Asn 715 | Gly | Gly | Gly | Tyr Lys 720 |
| Ala | Ser | Ser | Pro | Ala 725 | Glu | Ser | Ser | Pro | Glu 730 | Asp | Ser | Gly | Tyr | Met Arg 735 |
| Met | Trp | Cys | Gly 740 | Ser | Lys | Leu | Ser | Met 745 | Glu | Asn | Pro | Asp | Pro 750 | Lys Leu |
| Leu | Pro | Asn 755 | Gly | Asp | Tyr | Leu | Asn 760 | Met | Ser | Pro | Ser | Glu 765 | Ala | Gly Thr |
| Ala | Gly 770 | Thr | Pro | Pro | Asp | Phe 775 | Ser | Ala | Ala | Leu | Arg 780 | Gly | Gly | Ser Glu |
| Gly 785 | Leu | Lys | Gly | Ile | Pro 790 | Gly | His | Cys | Tyr | Ser 795 | Ser | Leu | Pro | Arg Ser 800 |

-continued

```
Tyr Lys Ala Pro Cys Ser Cys Ser Gly Asp Asn Asp Gln Tyr Val Leu
                805             810                 815
Met Ser Ser Pro Val Gly Arg Ile Leu Glu Glu Glu Arg Leu Glu Pro
            820             825             830
Gln Ala Thr Pro Gly Ala Gly Thr Phe Gly Ala Ala Gly Ser His
            835             840             845
Thr Gln Pro His His Ser Ala Val Pro Ser Ser Met Arg Pro Ser Ala
    850             855             860
Ile Gly Gly Arg Pro Glu Gly Phe Leu Gly Gln Arg Cys Arg Ala Val
865             870             875                 880
Arg Pro Thr Arg Leu Ser Leu Glu Gly Leu Gln Thr Leu Pro Ser Met
                885             890             895
Gln Glu Tyr Pro Leu Pro Thr Glu Pro Lys Ser Pro Gly Glu Tyr Ile
            900             905             910
Asn Ile Asp Phe Gly Glu Ala Gly Thr Arg Leu Ser Pro Ala Pro
            915             920             925
Pro Leu Leu Ala Ser Ala Ala Ser Ser Ser Leu Leu Ser Ala Ser
    930             935             940
Ser Pro Ala Ser Ser Leu Gly Ser Gly Thr Pro Gly Thr Ser Ser Asp
945             950             955                 960
Ser Arg Gln Arg Ser Pro Leu Ser Asp Tyr Met Asn Leu Asp Phe Ser
                965             970             975
Ser Pro Lys Ser Pro Lys Pro Ser Thr Arg Ser Gly Asp Thr Val Gly
            980             985             990
Ser Met Asp Gly Leu Leu Ser Pro Glu Ala Ser Ser Pro Tyr Pro Pro
        995             1000            1005
Leu Pro Pro Arg Pro Ser Thr Ser Pro Ser Ser Leu Gln Gln Pro Leu
    1010            1015            1020
Pro Pro Ala Pro Gly Asp Leu Tyr Arg Leu Pro Pro Ala Ser Ala Ala
1025            1030            1035                1040
Thr Ser Gln Gly Pro Thr Ala Gly Ser Ser Met Ser Ser Glu Pro Gly
                1045            1050            1055
Asp Asn Gly Asp Tyr Thr Glu Met Ala Phe Gly Val Ala Ala Thr Pro
            1060            1065            1070
Pro Gln Pro Ile Val Ala Pro Pro Lys Pro Glu Gly Ala Arg Val Ala
            1075            1080            1085
Ser Pro Thr Ser Gly Leu Lys Arg Leu Ser Leu Met Asp Gln Val Ser
    1090            1095            1100
Gly Val Glu Ala Phe Leu Gln Val Ser Gln Pro Pro Asp Pro His Arg
1105            1110            1115                1120
Gly Ala Lys Val Ile Arg Ala Asp Pro Gln Gly Gly Arg Arg Arg His
                1125            1130            1135
Ser Ser Glu Thr Phe Ser Ser Thr Thr Thr Val Thr Pro Val Ser Pro
            1140            1145            1150
Ser Phe Ala His Asn Ser Lys Arg His Asn Ser Ala Ser Val Glu Asn
    1155            1160            1165
Val Ser Leu Arg Lys Ser Ser Glu Gly Ser Ser Ser Thr Leu Gly Gly Gly
        1170            1175            1180
Asp Glu Pro Pro Thr Ser Pro Gly Gln Ala Gln Pro Leu Val Ala Val
1185            1190            1195                1200
Pro Pro Val Pro Gln Ala Arg Pro Trp Asn Pro Gly Gln Pro Gly Ala
                1205            1210            1215
Leu Ile Gly Cys Pro Gly Gly Ser Ser Ser Pro Met Arg Arg Glu Thr
            1220            1225            1230
```

-continued

| Ser | Val | Gly | Phe | Gln | Asn | Gly | Leu | Asn | Tyr | Ile | Ala | Ile | Asp | Val | Arg |
|     |     | 1235 |    |     |     |     | 1240 |    |     |     |     | 1245 |    |     |     |

| Gly | Glu | Gln | Gly | Ser | Leu | Ala | Gln | Ser | Gln | Pro | Gln | Pro | Gly | Asp | Lys |
|     | 1250 |    |     |     |     | 1255 |    |     |     |     | 1260 |    |     |     |     |

| Asn | Ser | Trp | Ser | Arg | Thr | Arg | Ser | Leu | Gly | Gly | Leu | Leu | Gly | Thr | Val |
| 1265 |    |     |     |     | 1270 |    |     |     |     | 1275 |    |     |     |     | 1280 |

| Gly | Gly | Ser | Gly | Ala | Ser | Gly | Val | Cys | Gly | Gly | Pro | Gly | Thr | Gly | Ala |
|     |     |     |     | 1285 |    |     |     |     | 1290 |    |     |     |     |     | 1295 |

| Leu | Pro | Ser | Ala | Ser | Thr | Tyr | Ala | Ser | Ile | Asp | Phe | Leu | Ser | His | His |
|     |     |     | 1300 |    |     |     |     | 1305 |    |     |     |     | 1310 |    |     |

| Leu | Lys | Glu | Ala | Thr | Val | Val | Lys | Glu |
|     | 1315 |    |     |     |     |     | 1320 |    |